(12) United States Patent
Cai et al.

(10) Patent No.: US 10,617,708 B2
(45) Date of Patent: Apr. 14, 2020

(54) PREECLAMPSIA

(71) Applicant: ASTON UNIVERSITY, Birmingham (GB)

(72) Inventors: Meng Cai, Birmingham (GB); Keqing Wang, Birmingham (GB); Asif Ahmed, Birmingham (GB)

(73) Assignee: ASTON UNIVERSITY, Birmingham (GB)

( * ) Notice: Subject to any disclaimer, the term of this patent is extended or adjusted under 35 U.S.C. 154(b) by 0 days.

(21) Appl. No.: 15/559,815

(22) PCT Filed: Mar. 16, 2016

(86) PCT No.: PCT/GB2016/050710
§ 371 (c)(1),
(2) Date: Sep. 19, 2017

(87) PCT Pub. No.: WO2016/151287
PCT Pub. Date: Sep. 29, 2016

(65) Prior Publication Data
US 2018/0050060 A1  Feb. 22, 2018

(30) Foreign Application Priority Data
Mar. 20, 2015  (GB) .................................. 1504772.3

(51) Int. Cl.
C12N 15/113  (2010.01)
A61K 31/713  (2006.01)
C12N 15/11  (2006.01)
C12Q 1/6883  (2018.01)
G01N 33/50  (2006.01)

(52) U.S. Cl.
CPC .......... *A61K 31/713* (2013.01); *C12N 15/111* (2013.01); *C12Q 1/6883* (2013.01); *G01N 33/50* (2013.01); *C12N 2310/113* (2013.01); *C12N 2310/141* (2013.01); *C12N 2320/30* (2013.01); *C12Q 2600/118* (2013.01); *C12Q 2600/178* (2013.01)

(58) Field of Classification Search
None
See application file for complete search history.

(56) References Cited

U.S. PATENT DOCUMENTS

| | | | | |
|---|---|---|---|---|
| 8,273,383 | B2 * | 9/2012 | Folkman | ................ A61K 31/56 424/682 |
| 8,513,209 | B2 * | 8/2013 | Olson | ................ A01K 67/0275 514/44 A |
| 9,198,981 | B2 * | 12/2015 | Ambati | ................ A61K 38/177 |
| 2003/0220262 | A1 | 11/2003 | Schreiner et al. | |
| 2006/0185027 | A1 | 8/2006 | Bartel et al. | |
| 2014/0348908 | A1 | 11/2014 | Brown et al. | |

FOREIGN PATENT DOCUMENTS

| | | |
|---|---|---|
| CN | 102286625 A * | 12/2011 |
| WO | 2004008946 A2 | 1/2004 |
| WO | 2009093254 A2 | 7/2009 |
| WO | 2013079701 A2 | 6/2013 |
| WO | 2014089029 A1 | 6/2014 |
| WO | 2014132083 A2 | 9/2014 |

OTHER PUBLICATIONS

Machine translation of CN102286625A bibliographic data, description, and claims, downloaded from the web on May 8, 2019. (Year: 2011).*
Wang, X et al., "miR-195 inhibits the growth and metastasis of NSCLC cells by targeting IGF1R", Tumor Biol., 2014; 35:8765-8770.
Wang, XY et al., "Differential miRNA expression and their target genes between NGX6-positive and negative colon cancer cells", Mol Cell Biochem., 2010; 345:283-290.
Williams, AE, "Functional aspects of animal microRNAs", Cell Mol Life Sci., 2008; 65:545-562.
Williams, Z et al., "Comprehensive profiling of circulating microRNA via small RNA sequencing of cDNA libraries reveals biomarker potential and limitations", Proc Natl Acad Aci USA, 2013; 110:4255-4260.
Wu, FT et al., "A systems biology perspective on sVEGFR1: its biological function, pathogenic role and therapeutic use", J Cell Mol Med., 2010; 14:528-552.
Wu, L et al, "Circulating microRNAs are elevated in plasma from sever preeclamptic pregnancies", Reproduction, 2012; 143:389-397.
Xiang, Y et al., "MiR-152 and miR-185 co-contribute to ovarian cancer cells cisplatin sensitivity by targeting DNMT1 directly: a novel epigenetic therapy independent of decitabine", Oncogene, 2013; doi:10.1038/onc.2012.575.
Xu, P et al., "Variations of microRNAs in human placentas and plasma from preeclamptic pregnancy", Hypertension, 2014; 63:1276-1284.
Xu, Q et al., "A regulatory circuit of miR-1448a/152 and DNMT1 in modulating cell transformation and tumor angiogenesis through IGF-IR and IRS1", J Mol Cell Biol., 2013; 5:3-13.

(Continued)

*Primary Examiner* — Richard A Schnizer
(74) *Attorney, Agent, or Firm* — Gorman IP Law, APC

(57) ABSTRACT

The invention provides a method of treating preeclampsia, fetal growth restriction (FGR or IUGR), obesity in pregnancy, post-partum cardiomyopathy (heart failure in mothers), cancer and diabetic retinopathy, cardiomyopathy, myocardial infarction, wet microdegeneration and other disorders where angiogenesis is aberrant either diminished or exacerbated, comprising modulating the activity of micro RNA (miRNA). Also provided are an MiRNA modulator or a combination thereof or functional fragments or homologues thereof for use in the treatment of preeclampsia, fetal growth restriction, obesity in pregnancy, cancer, and diabetic retinopathy, cardiomyocyte infarction, wet microdegeneration as well as other disorder where angiogenesis is aberrant either diminished or exacerbated. Methods of modulating angiogenesis and pharmaceutical compositions using miR-122, miR-374b or inhibitors of miR-152 or miR195 are also provided together with methods of diagnosis using the miRNAs.

15 Claims, 32 Drawing Sheets

Figures 1A, 1B, 1C:
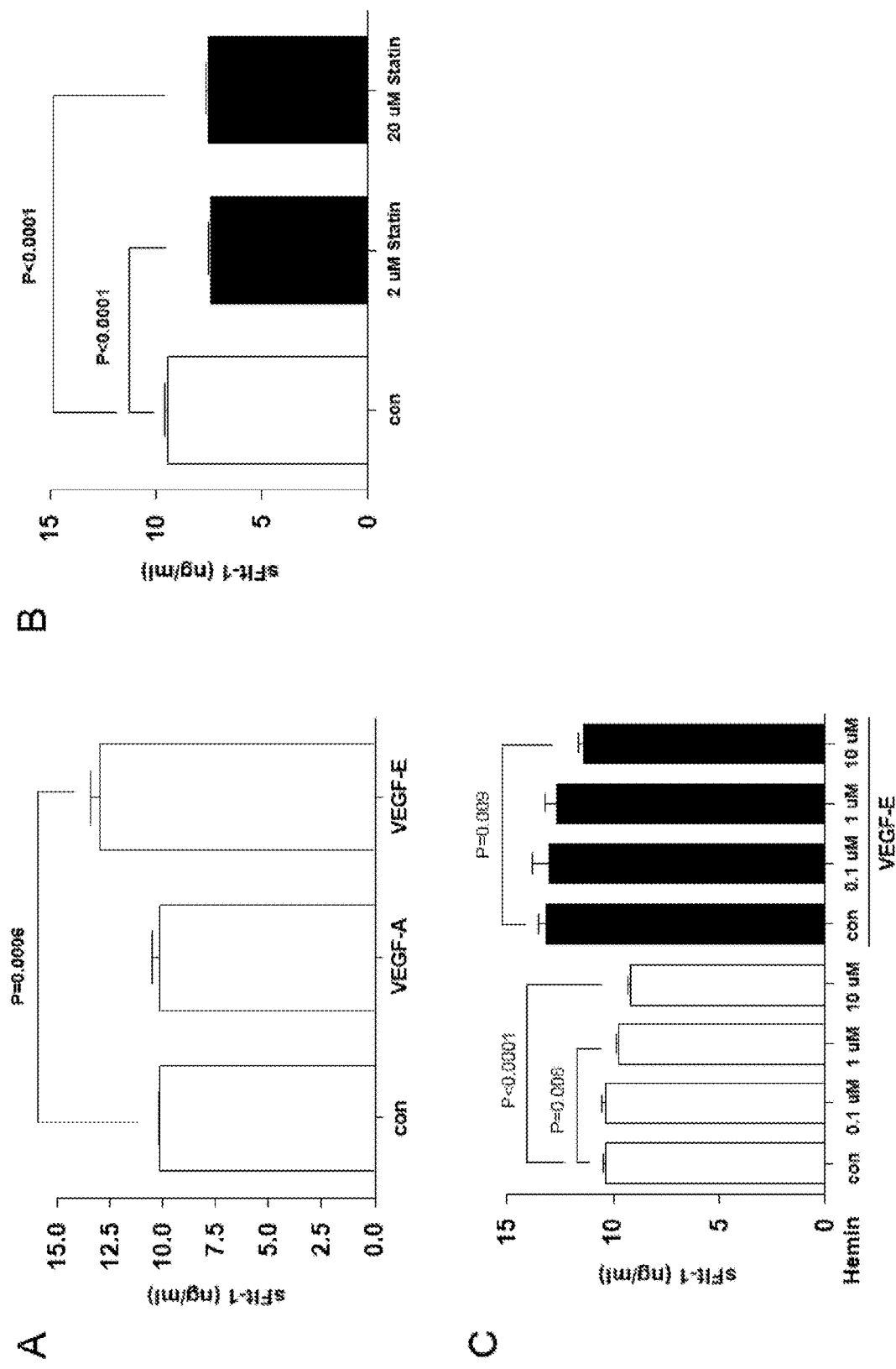

Specification includes a Sequence Listing.

(56) References Cited

OTHER PUBLICATIONS

Yang, Q et al., "Application of next-generation sequencing technology to profile the circulating microRNAs in the serum of preeclampsia versus normal pregnant women", Clin Chim Acta., 2011; 412:2167-2173.

Yang, WM et al., "Saturated fatty acid-induced miR-195 impairs insulin signaling and glycogen metabolism in HepG2 cells", FEBS Lett., 2014; 5793:00681-00684.

Yang, Y et al., "MicroRNA-195 acts as a tumor suppressor by directly targeting Wnt3a in HepG2 hepatocellular carcinoma cells", Mol Med Rep., 2014; 10:2643-2648.

You, XY et al., "HMGA1 is a New Target of miR-195 Involving Isoprenaline-Induced Cardiomyocyte Hypertrophy", Biochemistry (Mosc), 2014; 79:538-544.

Zampetaki, A et al., "Role of miR-195 in Aortic Aneurysmal Disease", Circulation Research., 2014; 115:857-866.

Zhang, Y et al., "MicroRNA-155 contributes to preeclampsia by down-regulating CYR61", Am J Obstet Gynecol., 2010; 202:466. e1-7.

Zhang, Y et al., "Elevated levels of hypoxia-inducible microRNA-210 in pre-eclampsia: new insights into molecular mechanisms for the disease", J Cell Mol Med., 2012; 16:249-259.

Zhao, FL et al., "Serum microRNA-195 is down-regulated in breast cancer: a potential marker for the diagnosis of breat cancer", Mol Biol Rep., 2014; 41:5913-5922.

Zheng, X et al., "MiR-15b and miR-152 reduce glioma cell invasion and angiogenesis via NRP-2 and MMP-3", Cancer Lett., 2013; 329:146-154.

Zhou, X et al., "Altered expression of miR-152 and miR-148a in ovarian cancer is related to cell proliferation", Oncol Rep., 2012; 27:447-454.

Zhu, XM et al., "Differential expression profile of microRNAs in human placentas from preeclamptic pregnancies vs normal pregnancies", Am J Obstet Gynecol., 2009; 200: 661.e1-7.

Zhu, XM et al., "Overexpression of miR-152 leads to reduced expression of human leukocyte antigen-G and increased natural killer cell mediated cytolysis in JEG-3 cells", American Journal of Obstetrics & Gynecol., 2010; 202:592.e1-7.

Ahmed, A et al., "Introduction of Placental Heme Oxygenase-1 Protective Against TNFα-induced Cytotoxicity and Promotes Vessel Relaxation", Feb. 9, 2000, Molecular Medicine, pp. 391-409, 6(5).

Constantine, MM et al., Pravastatin for the Prevention of Preeclampsia in High-risk Pregnant Women, Obs. Gynecol., Feb. 2013, pp. 349-353, vol. 121.

Cudmore, M et al., "Negative Regulation of Soluble Flt-1 and Soluble Endoglin Release by Heme Oxygenase-1", Circulation, Jan. 19, 2007, pp. 1789-1797, vol. 115.

George, EM et al., "Introduction of heme oxygenase-1 attenuates sFlt-1-induced hypertension in pregnant rats", Am. J. Physiol., Aug. 24, 2011, pp. r1495-r1500, vol. 115.

Great Britain Search Report dated Dec. 9, 2015.

International Search Report dated Aug. 25, 2016.

Lefkou, E et al., "Clinical improvement and Successful Pregnancy in a Preclamptic Patient With Antiphospholipid Syndrome Treated With Pravastatin", Hypertension, Mar. 3, 2014, pp. e118-e119.

Liu Chuanix Ed—Ha Hundjoo et al., Archives of Pharmacal Research, Natl. Fisheries University, Pusan, KR, vol. 36, No. 10, Jul. 24, 2013 (Jul. 24, 2013), pp. 1169-1177, XP035312424, ISSN: 0253-6269, [retrieved on Jul. 24, 2013], DOI: 10.1007/S12272-013-0213-4.

Pineles, BL et al., "Distinct subsets of microRNAs are expressed differently in the human placentas of patients with preeclamsia", American Journal of Obstetrics & Gynecology, Mar. 6, 2007, pp. 261.e1-261.e6, vol. 196, No. 3, Mosby, St Louis, MO, US.

Ramma, W & Ahmed, A, "Therapeutic potential of statins and the induction of heme oxygenase-1 in preeclampsia", Journal of Reproductive Immunology, Mar. 2014, pp. 153-160, 101-102(100).

Zhou, C. et al., "Angiotensin Receptor Agonistic Autoantibody-Mediated Tumor Necrosis Factor-α-induction Contributes to Increased Soluble Endoglin Production in Preeclampsia", Circulation, Jan. 11, 2010, pp. 436-444, 121(3).

Ahmad S, Ahmed A, "Elevated placental soluble vascular endothelial growth factor receptor-1 inhibits angiogensis in preeclampsia", Cir Res, 2004; 95:884-891.

Ahmad, S et al., "Autocrine activity of soluble Flt-1 controls endothelial cell function and angiogenesis", Vasc Cell, 2011; 3:15.

Ahmad, S et al., "Direct evidence for endothelial vascular endothelial growth factor receptor-1 function in nitric oxide-mediated angiogenesis", Cir Res., 2006; 99:715-722.

Albrecht, EW et al., "Protective role of endothelial nitric oxide synthase", Journal of Pathology, 2003; 199:8-17.

Amer, M et al., "Hsa-miR-195 targets PCMT1 in hepatocellular carcinoma that increases tumor life span", Tumor Biol., 2014. 35:11301-11309.

Bando, H et al., "Association between intratumoral free and total VEGF, soluble VEGFR-1, VEGFR-2 and prognosis in breast cancer", Br J Cancer, 2005; 92:553-561.

Bartel, DP, "MicroRNAs: target recognition and regulatory functions", Cell, 2009; 136:215-233.

Baumwell, S et al., "Pre-Eclampsia: Clinical Manifestations and Molecular Mechanisms", Nephron Clin Pract., 2007; 106:c72-c81.

Blann, AD et al., "Vascular endothelial growth factor and its receptor, Flt-1, in the plasma of patients wit coronary or peripheral atherosclerosis, or Type II diabetes", Clin Sci (London), 2002; 102:187-194.

Bonauer, A et al., "MicroRNA-92a controls angiogenesis and functional recovery of ischemic tissues in mice", Science, 2009; 324:1710-1713.

Braconi, C et al., "MicroRNA-dependent regulation of DNA methyltransferase-1 and tumor suppressor gene expression by interleukin-6 in human malignant cholangiocytes", Hepatology, 2010; 51:881-890.

Bujold, E et al., "Acetylsalicylic acid for the prevention of preeclampsia and intra-uterine growth restriction in women with abnormal uterine artery Doppler: a systematic review and meta-analysis", J Obstet Gynaecol Can, 2009; 31:818-826.

Busk, PK et al., "MicroRNA profiling in early hypertrophic growth of the left ventricle in rats", Biochemical Biophysical Research Communications, 2010; 396:989-993.

Bussolati, B et al., Vascular endothelial growth factor receptor-1 modulates vascular endothelial growth factor-mediated angiogenesis via nitric oxide, Am J. Pathol, 2001, 159: 993-1008.

Chen, Y et al., "Altered Expression of MiR-148a and MiR-152 in gastrointestinal cancers and its clinical significance", J Gastrointest Surg., 2010; 14:1170-1179.

Chen, YQ et al., "Abated microRNA-195 expression protected mesangial cells from apoptosis in early diabetic renal injury in mice", J Nephol., 2012; 25:566-576.

Cheng, W et al., "microRNA-155 regulates angiotensin II type 1 receptor expression in umbilical vein endothelial cells from severely pre-eclamptic pregnant women", Int J Mol Med., 2011; 27:393-399.

Dai, Y et al., "MicroRNA-155 inhibits proliferation and migration of human extravillous trophoblast derived HTR-8/Svneo cells via down-regulatting cyclin D1", Placenta, 2012; 33:824-829.

Dai, Y et al., "MicroRNA-155 is involved in the remodelling of human-trophoblast-derived HTR-8/Svneo cells induced by lipopolysaccharides" Hum Reprod., 2011; 26:1882-1891.

De Vivo, A et al., "Endoglin, P1GF and sFlt-1 as markers for predicting pre-eclampsia", Acta Obstetricia et Gynecologica Scand., 2008; 87:837-842.

Duda, DG et al., "Role of eNOS in neovascularization: NO for endothelial progenitor cells", Trends in Molecular Medicine, 2004; 10:143-145.

Ebox, JM et al., "A naturally occurring soluble form of vascular endothelial growth factor receptor 2 detected in mouse and human plasma" Mol Cancer Res., 2004; 2:315-326.

Enquobahrie, DA et al., "Placental microRNA expression in pregnancies complicated by preeclampsia", Am J Obstet Gynecol., 2011; 204:178.e12-21.

(56) References Cited

OTHER PUBLICATIONS

Fatini, C et al., "Endothelial nitric oxide synthase gene influences the risk of pre-eclampsia, the recurrence of negative pregnancy events, and the maternal-fetal flow", J Hypertens., 2006; 24:1823-1929.

Findley, CM et al., "Plasma levels of soluble Tie2 and vascular endothelial growth factor distingeush critical limb schemia from intermitttent claudication in patients with peripheral arterial disease", J AM Coll Cardiol., 2008; 52:387-393.

Forstermann, U et al., "Endothelial nitric oxide synthase in vascular disease: from marvel to menace", Circulation, 2006; 113:1708-1714.

Francis, SE et al., "Central role of alpha5beta1 integrin and fibronectin in vascular development in mouse embryos and embryoid bodies", Arterioscler Thromb Vasc Biol., 2002; 22:927-933.

Fu, MG et al., "Differntial expression of miR-195 in esophageal squamous cell carcinoma and miR-195 expression inhibits tumor cell proliferation and invasion by targeting of Cdc42", FEBS Lett., 2013;3471-3479.

Grill, S et al., "Potential markers of preeclampsia—a review", Reprod Biol Endocrinol., 2009; 7:70-83.

Grzesiak, JJ et al., "Type I Collagen and Divalent Cation Shifts Disrupt Cell-Cell Adhesion, Increase Migration, and Decrease PTHrP, IL-6, and IL-8 Expression in Pancreatic Cancer Cells", Int J Gastrointest Cancer, 2005; 36:131-146.

Gu, Y et al., "Differential miRNA expression profiles between the first and third trimester human placentas", Am J Physiol Endocrinol Metab., 2013; 304:E836-E843.

Guo, H et al., "miR-195 Targets HDGF to inhibit proliferation and invasion of NSCLC cells", Tumor Biol., 2014; 35:8861-8866.

Guo, ST et al., "MicroRNA-497 targets insulin-like growth factor 1 receptor and has a tumour suppressive role in human colorectal cancer", Oncogene, 2013; 32:1910-1920.

He, L et al., "MicroRNAs: small RNAs with a big role in gene regulation", Nat Rev Genet., 2004; 5:522-531.

Herrera, BM et al., "Global microRNA expressions profiles in insulin target tissues in spontaneous rat model of type 2 diabetes", Diabetologia, 2010; 53:1099-1109.

Hiroki, E et al., "Changes in microRNA expression levels correlate with clinicopathological features and prognosis in endometrial serous adenocarcinomas", Cancer Sci., 2010; 101:241-249.

Hladunewich, M et al., "Pathophysiology of the clinical manifestations of preeclampsia", Clin J Am Soc Nephrol., 2007; 2:543-549.

Hood, JD et al., "Role of integrins in cell invasion and migration", Nat Rev Cancer, 2002; 2:91-100.

Hou, W et al., "The let-7 microRNA enhances heme oxygenase-1 by suppressing Bach1 and attenuates oxidant injury in human hepatocytes", Biochim Biophys Acta, 2012; 1819:1113-1122.

Hromadnikova, I et al., "Absolute and relative quantification of placenta-specific micromas in maternal circulation with placental insufficiency-related complications", J Mol Diagn.,2012; 14:160-167.

Hu, Y et al., "Differential expression profile of microRNAs in the placentae of Chinese patients with severe pre-eclampsia", Clin Chem Lab Med., 2009; 47(8):923-929.

Huang, J et al., "Down-regulated microRNA-152 induces aberrant DNA methylation in hepatitis B virus-related hepatocellular carcinoma by targeting DNA methyltransferase 1", Hepatology, 2010; 52:60-70.

Huang, PI, "Endothelial Nitric Oxide Synthase and Endothelial Dysfunction", Current Hypertension Reports, 2003; 5:473-480.

Hunter, A et al., "Serum levels of vascular endothelial growth factor in preeclamptic and normotensive pregnancy", Hypertension, 2000; 36:965-969.

Jain, M et al., "ZNF367 inhibits cancer progresion and is targeted by miR-195", PLoS One, 2014; 9:e101423.

Jaroszewicz, J et al., "Circulating vascular endothelial growth factor and its soluble receptors in patients with liver cirrhosis: possible association with hepatic function impairment", Cytokine, 2008; 44:14-17.

Ji, W et al., "MicroRNA-152 targets DNA methyltransferase 1 in NiS-transformed cells via a feedback mechanism", Carcinogenesis, 2013; 34:446-453.

Kendall, RL et al., "Identification of a natural soluble form of the vascular endothelial growth factor receptor, FLT-1, and its heterodimerization with KDR", Biochem Biophys Res Commun., 1996; 226:324-328.

Kitano, K et al., "CpG island methylation of microRNAs is assoicated with tumor size and recurrence of non-small-cell lung cancer", Cancer Sci., 2011; 102:2126-2131.

Kozakowska, M et al., "Role of heme oxygenase-1 in postnatal differentiation of stem cells: a possicble cross-talk with microRNAs", Antioxid Redox Signal., 2014; 20: 1827-1850.

Lamszus, K et al., "Levels of soluble vascular endothelial growth factor (VEGF) receptor 1 in astrocytic tumors and its relation to malignancy, vasularity, and VEGF-A" Clin Cancer Res., 2003; 9:1399-1405.

Lee, DC et al., "miR-210 targets iron-sulfur cluster scaffold homologue in human trophoblast cell lines: siderosis of interstitial trophoblasts as a novel pathology of preterm preeclampsia and small-for-gestational-age pregnancies", Am J Pathol., 2011; 179:590-602.

Leslie, K et al., "Early prediction and prevention of pre-eclampsia", Best Practice & Research Clinical Obstetrics Gynaecology, 2011; 25:343-354.

Levine, RJ et al., "Circulating angiogenic factors and the risk of preeclampsia", N Engl J Med., 2004; 350:672-683.

Lewis, BP et al., "Prediction of mammalian microRNA targets", Cell, 2003; 115:787-798.

Li, P et al., "microRNA-29b contributes to pre-eclampsia through its effects on apoptosis, invasion and angiogenesis of trophoblast cells", Clin Sci (Lond), 2013; 124:27-40.

Lin, MI et al., "Vascular endothelial growth factor signaling to endothelial nitric oxide synthase: more than a FLeeTing moment", Circ Res., 2006; 99: 666-668.

Liu, L et al., "MicroRNA-181a regulates local immune balance by inhibiting proliferation and immunosuppressive properties of mesenchymal stem cells" Stem Cells, 2012; 30:1756-1770.

Lockwood, CJ, et al., "Preeclampsia-related inflammatory cytokines regulate interleukin-6 expression in human decidual cells", Am J Pathol, 2008; 172:1571-1579.

Long, G et al., "Circulating miR-30a, miR-195 and let-7b associated with acute myocardial infarction", PLoS One, 2012;7:e50926.

Luo, L et al., "MicroRNA-378A-5P promotes trophoblast cell survival, migration and invasion by targeting Nodal", Cell Sci., 2012; 125:3124-3132.

Luo, Q et al., "MicroRNA-195-5p is a potential diagnostic and therapeutic target for brest cancer", Oncol Rep., 2014; 31:1096-1102.

Manaster, I et al., "MiRNA-mediated control of HLA-G expression and function" PLoS One, 2012; 7:e33395.

Mancini, M et al., "MicroRNA-152 and -181a participate in human dermal fibroblasts senescence acting on cell adhesion and remodeling of the extra-cellular matrix", Aging (Albany NY), 2012; 4:843-853.

Maynard, SE et al., "Excess placental soluble fms-like tyrosine kinase 1 (sFlt1) may contribute to endothelial dysfunction, hypertension, and proteinuria in preclampsia", J Clin Invest. 2003; 111:649-658.

Mayor-Lynn, K et al., "Expression profile of microRNAs and mRNAs in human placentas from pregnancies complicated by preeclampsia and preterm labor", Reprod Sci., 2011; 18:46-56.

McCarthy, FP et al., "Peroxisome proliferator-activated receptor-y as a potential therapeutic target in the treatment of preeclampsia" Hypertension, 2011; 58:280-286.

Moh, MC et al., "The roles of cell adhesion molecules in tumor suppression and cell migration: a new paradox", Cell Adh Migr., 2009; 3:334-336.

Mortuza, R et al., "miR-195 regulates SIRT1-mediated changes in diabetic retinopathy", Diabetologia, 2014; 57:1037-1046.

Muralimanoharan, S et al., "MIR-210 modulates mitochondrial respiration in placenta with preeclampsia", Placenta, 2012; 33:816-823.

(56) References Cited

OTHER PUBLICATIONS

Murdoch, CE et al., "Glutaredoxin-1 up-regulation induces soluble vascular endothelial growth factor receptor 1, attenuating post-ischemia limb revascularization", J Bio Chem, 2014; 289:8633-8644.

Noack, F et al., "miRNA expression profiling in formalin-fixed and paraffin placental tissue samples from pregnancies with severe preeclampsia", J Perinat Med., 2011; 39:267-271.

Ortega, FJ et al., "Profiling of circulating microRNAs reveals common microRNAs linked to type 2 diabetes that change with insulin sensitization", Diabetes Care, 2014; 37:1375-1383.

Ozkan, S et al., "Placental expressions of insulin-like growth factor-I, fibroblast growth factor-basic, and neural cell adhesion molecule in preeclampsia", J Matern Fetal Neonatal Med, 2008; 21:831-838.

Pan, M et al., "Sequencing the miRNAs in maternal plasma from women before and after parturition", J Nanosci Nanotechnol., 2012; 12:4035-4043.

Pennington, KA et al., "Preeclampsia: multiple approaches for a multifactorial disease", Dis Model Mech, 2012; 5:9-18.

Porrello, ER et al., "MiR-15 family regulates postnatal mitotic arrest of cardiomyocytes", Circ Res., 2011; 109:670-679.

Poston, L et al., "Endothelial dysfunction in pre-eclampsia", Pharmacol Rep., 2006; 58 Suppl: 69-74.

Powe, CE et al., "Preeclampsia, a disease of the maternal endothelium: the role of antiangiogenic factors and implications for later cardiovascular disease", Circulation. 2011; 123:2856-2869.

Qin, J et al., "A panel of microRNAs as a new biomarkers for the detection of deep vein thrombosis", 2015; J Thromb Thrombolysis 39:215-221.

Qin, L et al., "Steroid receptor coactivator-1 upregulates integrin expression to promote breast cancer cell adhesion and migration", Cancer Res., 2011; 71:1742-1751.

Ramma, W et al., "Is inflammation the cause of pre-eclampsia?" Biochem Soc Trans., 2011; 39:1619-1627.

Ramma, W et al., "The elevation in circulating anti-angiogenic factors is independent of markers of neutrphil activation in preeclampsia", Angiogenesis, 2012; 15:341-348.

Sibai, B et al., "Pre-eclampsia", Lancet, 2005, 365:785-799.

Silasi, M et al., "Abnormal Placentation, Angiogenic Factors, and the Pathogenesis of Preeclampsia", Obstet Gynecol Clin North Am., 2010; 37:239-253.

Skrzypek, K et al., "Interplay between heme oxygenase-1 and miR-378 affects non-small cell lung carcinoma growth, vascularization, and metastasis", Antioxid Redox Signal., 2013; 19:644-660.

Soleymanlou, N et al., "Molecular evidence of placental hypoxia in preeclampsia" J Clin Endocrinol Metab, 2005; 90:4299-4308.

Steegers, EA et al., "Pre-eclampsia", Lancet, 2010, 376, 631-644.

Stepan, H et al., "Predictive value of maternal angiogenic factors in second trimester pregnancies with abnormal uterine perfusion", Hypertension, 2007; 49:818-824.

Stumpel, DJ et al., "Hypermethylation of specific microRNA genes in MLL-rearranged infant acute lymphoblastic leukemia: major matters at a micro scale", Leukemia, 2011; 25:429-439.

Sun, HX et al., "Essential role of microRNA-155 in regulating endothelium-dependent vasorelaxation by targeting endothelial nitric oxide synthase", Hypertension, 2012; 60:1407-1414.

Tsuruta, T et al., "miR-152 is a tumor suppressor microRNA that is silenced by DNA hypermethylation in endometrial cancer", Cancer Res., 2011; 71:6450-6462.

Van Rooij, E et al., "A signature pattern of stress-responsive microRNAs that can evoke cardiac hypertrophy and heart failure", Proc Natl Acad Sci USA, 2006; 103:18255-18260.

Venkatesha, S et al., "Soluble endoglin contributes to the pathogenesis of preeclampsia", Nat Med., 2006; 12:642-649.

Verlohren, S et al., "The sFlt-1/P1GF ratio in different types of hypertensive pregnancy disorders and its prognostic potential in preeclampsia patients", Am J Obstet Gynecol., 2012; 206:58.el-8.

Wang, A et al., "MicroRNA-155 inhibits proliferation and migration of human extravillous trophoblast derived HTR-8/Svneo cells via down-regulatting cyclin D1", Placenta, 2012; 33:824-829.

Wang, A et al., "Preeclampsia: the role of angiogenic factors in its pathogenesis", Physiology (Bethesda), 2009; 24:147-158.

Wang, L et al., "MicroRNA-195 inhibits colorectal cancer cell proliferation, colony-formation and invasion through targeting CARMA3", Mol Med Rep., 2014; 10:473-478.

Wang, QY et al., "α1,3 Fucosyltransferase-VII up-regulates the mRNA of α5 Integrin and its Biological Function", J Cell Biochem, 2008; 104:2078-2090.

Wang, R et al., "MicroRNA-195 suppresses angiogenesis and metastasis of hepatocellular carcinoma by inhibiting the expression of VEGF, VAV2, and CDC42" Hepatology, 2013; 58:642-653.

\* cited by examiner

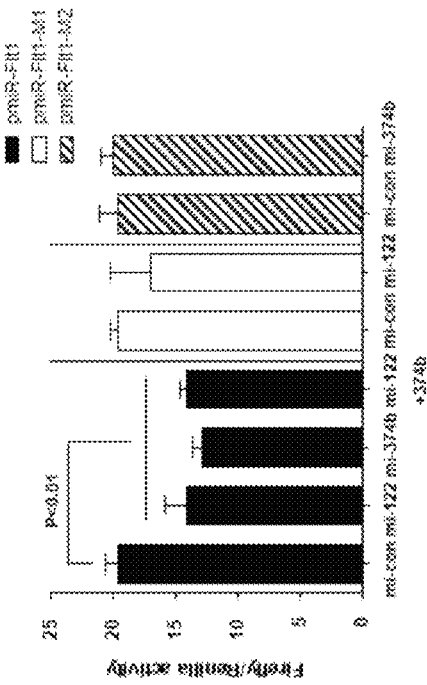
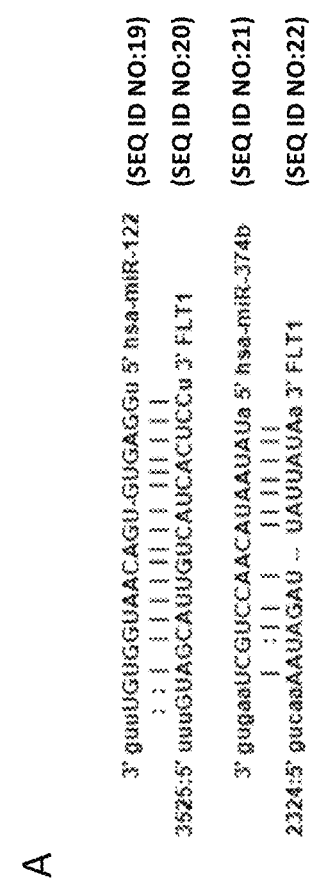
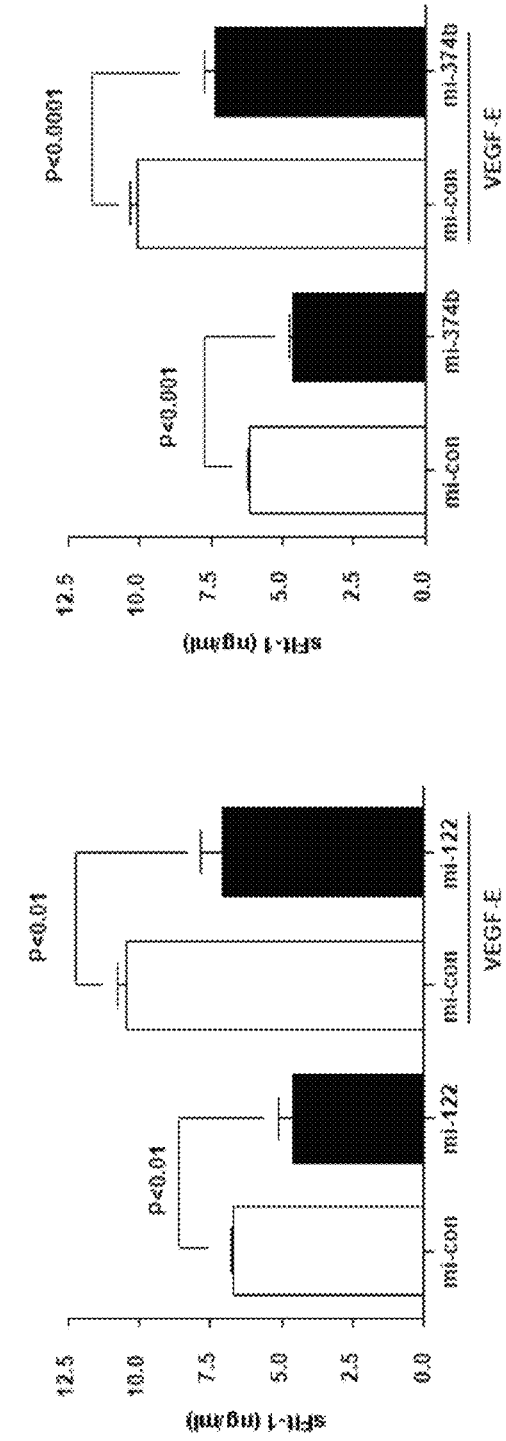
Figures 4A - 4B

PREECLAMPSIA

This application is the National Phase Under 35 USC § 371 of PCT International Application No. PCT/GB2016/050710 filed on Mar. 16, 2016, which claims priority under 35 U.S.C. § 119 on Patent Application No. 1504772.3 filed in the United Kingdom on Mar. 20, 2015, the entire contents of each of which are hereby incorporated by reference.

The invention provides methods of treating preeclampsia by modulating the activity of an miRNA.

INTRODUCTION

Soluble fms-like tyrosine kinase-1 (sFlt-1 or sVEGF-1) is a splice variant of VEGF receptor 1 (Flt-1) and acts as a receptor of vascular endothelial growth factor (VEGF) (Kendall et al., 1996). However, sFlt-1 lacks the transmembrane and cytoplasmic domains of the receptor, and thereby blunts the VEGF signalling pathway by binding to the free circulating VEGF (Wu et al., 2010). The abnormal sFlt-1 expression was identified in many pathological conditions, including different type of cancers, liver cirrhosis, diabetes and peripheral arterial disease (Bando et al., 2005; Ebos et al., 2004; Lamszus et al., 2003; Jaroszewicz et al., 2008; Blann et al., 2002; Findley et al., 2008).

Among these diseases, the role of sFlt-1 is best characterized in the pathogenesis of preeclampsia. Preeclampsia is a maternal medical condition clinically defined as hypertension, proteinuria and renal damage in pregnant women. Currently preeclampsia is the major cause of maternal and perinatal mortality and morbidity (Steegers et al., 2010) and affects 3% to 8% of all pregnancies and women worldwide (Sibai et al., 2005). The pathogenesis of preeclampsia is complex, but it has been suggested that the endothelial dysfunction and resulted abnormal angiogenesis, a process which new blood vessels form from existed ones, in the placenta underlie the clinical manifestation of this medical condition (Hladunewich et al., 2007; Silasi et al., 2010; Maynard et al., 2008). The excessive expression of sFlt-1 in the plasma and placenta of preeclamptic women was identified and the plasma level of sFlt-1 could be used as a potential clinical marker of preeclampsia (Stepan et al., 2007). Moreover, the elevated sFlt-1 was thought to be the main cause of preeclampsia (Maynard et al., 2003; Powe et al., 2011). Our previous data demonstrated that Heme oxygenase 1 (Hmox1), a protective enzyme, negatively regulates sFlt-1 release, whereas the VEGF growth factors promotes sFlt-1 expression (Cudmore et al., 2007; Ahmad et al., 2011). Based on these findings, our and others started pilot trials to use statin, a potent Hmox1 inducer, to prevent the preeclampsia in high risk women (Costantine et al., 2013). However, the molecular mechanism of how Hmox1 or VEGF regulates sFlt-1 is still unknown.

MicroRNA is a 21-23-nt small non-coding RNA which binds to 3'-UTR of the mRNA of their target genes with a partially complement manner, and thus leads to the translational repression of target genes (Bartel 2009; Lewis et al., 2003; Williams 2008). Recently, microRNAs are shown to be important in the regulation of many developmental, physiological and pathological processes (Williams 2008; He and Hannon, 2004). Microarray profiling and further quantitative PCR analysis have revealed that microRNAs are differently expressed in the placenta of preeclamptic and normal pregnant women (Pineles et al., 2007; Zhu et al., 2009; Hu et al., 2009; Mayor-Lynn et al., 2011; Enquobahrie et al., 2011; Noack et al., 2011). Furthermore, the interaction of microRNA and Hmox1 in stem cell differentiation, lung carcinoma and oxidant injury was reported (Kozakowska et al., 2014; Skrzypek et al., 2013; Hou et al., 2012). Thus, we hypothesized that Hmox1 may regulate sFlt-1 release via microRNAs and the dysregulation of microRNAs in placenta contributes to the preeclamptic pathogenesis. Utilizing a qPCR based microarray, our present study identified two microRNAs, miR-122 and miR-374b, which can be regulated by hemin, a potent Hmox1 inducer. Furthermore, these microRNAs were demonstrated to be regulated by statin, Hmox1 and VEGF which also regulate sFlt-1 expression. Moreover, sFlt-1 was proved to be the direct target of these microRNAs and the regulation of sFlt-1 by Hmox1 was conducted by these microRNAs. Most importantly, these microRNAs are decreased in the preeclampsia patients and RuPP preeclamptic model. The negative correlation of these microRNAs and blood pressure in animal model was also discovered. Our study provides the novel molecular mechanism of sFlt-1 regulation and these microRNAs may serve as the new therapeutic targets of sFlt-1 related diseases.

MicroRNA-152 is a member of broadly conserved miR-148/152 family. It has been shown to regulate epigenesis by targeting DNMT1 (Xiang et al., 2013; Ji et al., 2013; Huang et al., 2010; Braconi et al., 2010), inhibits cancer cell proliferation and adhesion (Zhou et al., 2012; Mancini et al., 2012) and increases cell cytolysis (Zhu et al., 2010).

Further study confirmed its anti-tumor effect, and hence the down-regulation of miR-152 expression by hypermethylation in various cancer types (Hiroki et al., 2010; Tsuruta et al., 2011; Braconi et al., 2010; Chen et al., 2010; Huang et al., 2010; Wang et al., 2010; Stumpel et al., 2011; Kitano et al., 2011; Zhou et al., 2012). Most importantly, it has been shown to be up-regulated in the placenta of preeclampsia patients (Zhu et al., 2009). Furthermore, miR-152 reduces tumor cell angiogenesis (Zheng et al., 2013; Xu et al., 2013) and down-regulates expression of important pregnancy-related gene (HLA-G) (Manaster et al., 2012). Since miR-152 inhibits cancer cell proliferation and angiogenesis and also implicated in the preeclampsia by microarray profiling, we hypothesized that miR-152 in the preeclampsia regulates endothelial function to contribute to the pathogenesis of preeclampsia. In the current study, we confirmed the up-regulation of miR-152 in the placenta of different gestational placentas, more precisely defined preeclampsia patients as well as in the animal preeclampsia models, demonstrated the increase of miR-152 expression under hypoxia and inflammatory condition. Further study revealed the decrease of PlGF expression, endothelial cell adhesion and angiogenic abilities upon overexpression of miR-152. Moreover, the intraperitoneal injection of virus expressing miR-152 caused devascularization in the placenta and restricted fetal growth. Furthermore, we identified a novel target of miR-152, ITGA5, in both endothelial cells and mouse models and proved the negative correlation of miR-152 and ITGA5 in the preeclampsia patient placental tissue. The identification of miR-152 and its target, ITGA5, in the pathogenesis of preeclampsia will contribute to the understanding of this medical condition and may offer novel therapeutic targets.

MicroRNA-195 is a member of the broadly conserved miR-15/107 super family. It has been shown to be a tumor suppressor and suppresses cancer cell proliferation, migration, invasion and angiogenesis by targeting various downstream factors (Amer et al., 2014; Zhao et al., 2014; Jain et al., 2014; Guo et al., 2014; Wang et al., 2014 a and b; Yang et al., 2014; Luo et al., 2014; Fu et al., 2013; Wang et al., 2013). Furthermore, miR-195 regulates insulin signalling pathway and is implicated in the type 2 diabetes as well as diabetic associated renal injury and retinopathy (Chen et al., 2012; Mortuza et al., 2014; Yang et al., 2014; Ortega et al., 2014; Herrera et al., 2010; Guo et al., 2013). Moreover, miR-195 is also associated with acute myocardial infarction and cardiac hypertrophy by inhibiting cell cycle in cardiomyocytes (Long et al., 2012; You et al., 2014; van Rooij et al., 2006; Busk and Cirera, 2010; Porrello et al., 2011). Interestingly, miR-195 has been recently demonstrated to regulate aortic extracellular matrix and can be used as biomarker for deep vein thrombosis (Zampetaki et al., 2014; Qin et al., 2014). Further studies revealed its role in the pregnancy and associated complications. The expression of miR-195 was significantly up-regulated in third trimester human placentas compared to first trimester (Gu et al., 2013). More importantly, the expression of miR-195 in the preeclamptic placenta is different compare to the normal pregnant placenta, implying the possible role of mir-195 in the pathogenesis of preeclampsia (Xu et al., 2014; Zhu et al., 2009; Hu et al., 2009).

Endothelial nitric oxide synthase (eNOS or NOS3) is an enzyme that breaks down L-arginin to generate nitric oxide (NO) gas in endothelial cells and plays a key role in the vascular endothelium (Huang, 2003). eNOS produces low concentration of NO which offers protection to the endothelial function and integrity and loss of eNOS causes a variety of diseases including preeclampsia (Albrecht et al., 2003; Förstermann and Münzel, 2006; Fatini et al., 2006). Moreover, eNOS/NO has been identified as a key mediator of neocascularization (Duda et al., 2004) and VEGF fails to angiogenesis in eNOS$^{-/-}$ mouse (Lin and Sessa, 2006). However the regulatory mechanisms of eNOS expression are largely unknown. So far, only one microRNA, miR-155, was reported to directly target eNOS in endothelial cells (Sun et al., 2012).

Since miR-195 inhibits cancer cell proliferation and angiogenesis and also implicated in the preeclampsia by microarray profiling, we hypothesized that miR-195 negatively regulates endothelial function to contribute to the pathogenesis of preeclampsia. In the current study, we confirmed the up-regulation of miR-195 in the placenta of different gestational placentas, obesity pregnant women, more precisely defined preeclampsia patients as well as in the animal preeclampsia models, demonstrated the increase of miR-195 expression under inflammatory (or in combination with hypoxia) condition. Further study revealed the decrease of PlGF expression, endothelial cell proliferation, viability, adhesive and angiogenic abilities upon overexpression of miR-195. Furthermore, we identified eNOS as a novel target of miR-195 and overexpression of eNOS$^{S1177D}$ rescued miR-195 mediated suppression of angiogenesis in endothelial cells. Giving the importance of eNOS in the pathogenesis of preeclampsia, the identification of miR-195 will contribute to the current understanding of this medical condition and may offer novel therapeutic targets.

The invention provides a method of treating preeclampsia by modulating the activity of microRNA (miRNA). The activity is typically the function of the miRNA in RNA silencing or post-transcriptional regulation of gene expression of one or more genes involved in preeclampsia, fetal growth restriction (FGR or IUGR), obesity in pregnancy, post-partum cardiomyopathy (heart failure), cancer and diabetic retinopathy, cardiomyopathy, myocardial infarction, wet macrodegeneration as well as other disorder where angiogenesis is aberrant either diminished or exacerbated, to reduce the symptoms or and diagnosis of these diseases in a subject, such as a human subject having symptoms of these diseases.

The miRNA is typically selected from one or more miR-122, miR-374b, miR-152 and miR-195 or functional fragments or homologues thereof. For example, one or more of miR-122, miR-374b plus miR-152 or miR-122, miR-374b plus miR-195.

miR-122, miR-374b, miR-152 and miR-195 and inhibitors of them are generally known in the art and indeed are commercially available from, for example, Qiagen Ltd, Manchester, United Kingdom.

They may be:

```
hsa-miR-122-5p
                                        (SEQ ID NO: 1)
uggagugugacaaugguguuug hsa-miR-374b
                                        (SEQ ID NO: 2)
auauaauacaaccugcuaagug hsa-miR-152-3p
                                        (SEQ ID NO: 3)
ucagugcaugacagaacuugg hsa-miR-195-5p
                                        (SEQ ID NO: 4)
uagcagcacagaaauauuggc hsa-miR-122-5p inhibitor
                                        (SEQ ID NO: 5)
caaacaccauugucacacucca hsa-miR-374b inhibitor
                                        (SEQ ID NO: 6)
cacuuagcagguuguauuauau hsa-miR-152-3p inhibitor
                                        (SEQ ID NO: 7)
ccaaguucugucaugcacuga hsa-miR-195-5p inhibitor
                                        (SEQ ID NO: 8)
gccaauauuucugugcugcua
```

Typically inhibitors are nucleic acid molecules substantially complementary to the miRNA to allow a duplex to form. For example, one or two bases may not be complementary, but still allow duplex formation to occur.

The term "functional fragments" is intended to mean fragments of miRNA (or inhibitors of miRNA) retaining the same biological activity as the native miRNA or its inhibitor. The native miRNA or its inhibitors may also have additional sequences of nucleic acids, such as 1, 2, 3, 5, 10 or 15 nucleic acids added to the 5' or 3' end of the miRNA sequence or its complementary sequence as appropriate. To increase the stability or achieve better efficiency, the native miRNA or its inhibitors may be modified chemically, for example pegylated. The activity is typically the ability to treat one or more symptoms of preeclampsia.

The term "homologue" is intended to mean a miRNA having the same activity as the miRNA, such as the regulation of the same gene(s) as the miRNA. For example, it is known that animal miRNAs are able to recognise target mRNAs by using as little as 6-7 nucleotides (the seed region) at the 5' end of the miRNA. Hence, typically such homologues are typically miRNA having at least 6 to 8, or at least 10 to 12 nucleotides at the 5' end which are identical to those of the native miRNA. The miRNA may be a miRNA mimic. Such mimics are chemically synthesized dsRNA which mimic endogenous miRNAs after transfection into cells.

The treatment may involve one or more of increasing miR-122, miR-374b, miR-152 or miR-195 activity; or decreasing miR-122, miR-374b, miR-152 or miR-195 activity in the subject with preeclampsia, FGR or IUGR, obesity in pregnancy, post-partum cardiomyopathy (heart failure), cancer and diabetic retinopathy, cardiomyopathy, myocardial infarction, wet macrodegeneration as well as other disorder where angiogenesis is aberrant either diminished or exacerbated.

A miRNA activity may be increased by upregulating miRNA production. Alternatively, miRNA, or functional fragments or homologues thereof, may be injected into the organism, for example, into the placenta. Furthermore, the miRNA, or functional fragments or homologues thereof, may be cloned into an expressing plasmid or packed into adenovirus, AAV or Lentivirus and injected into the organism by intravenously (IV), intramuscularly (IM) or subcutaneously (SC) administration.

miRNA may be inhibited by inhibitors of miRNA. For example, single stranded inhibitors of siRNA, such as inhibitors of miR-152 or mirR-195 may be used. Moreover, the inhibitors of miRNA, functional fragments or homologues thereof, may be cloned into an expressing plasmid or packed into adenovirus, AAV or Lentivirus and injected into the organism by intravenously (IV), intramuscularly (IM) or subcutaneously (SC) administration.

The use of miR-122 or miR-374b to modulate angiogenesis is also provided. The miRNA may be, for example, under or overexpressed in cells to study the effect on angiogenesis. This may be used, for example, to model disorder where angiogenesis is aberrant either diminished or exacerbated or, for example, preeclampsia in pregnant women or in post-partum cardiomyopathy in the mother. They may also be used in the treatment of cancers.

Pharmaceutical compositions comprising two or more miR-122, miR-374b, an inhibitor of miR-152 and an inhibitor of miR-195, or functional fragments or homologues, or pharmaceutically acceptable salts thereof. The miRNA may be used as its native form or with a modified form, for example pegylated.

miR-122 and miR374b may be used to inhibit sFlt-1 by introducing the miRNAs into a subject where angiogenesis is aberrant either diminished or exacerbated. They may, for example, be used in cells in vitro or animal models in vivo to modulate sFlt-1 and study the effects of sFlt-1 on the cell or animal model. Furthermore, they may, for example, be used in preeclamptic woman placenta to suppress the sFlt-1 level.

The invention will now be described by way of example only with reference to the following figures:

FIG. 1. Soluble fms-related tyrosine kinase 1 (sFlt-1) is regulated by various compounds and growth factor. (A) HUVEC cells were stimulated with VEGF-A (20 ng/ml) and VEGF-E (20 ng/ml) for 24 hours and the condition media was assayed for sFlt-1. (B) HUVEC cells were treated with 2 uM and 20 uM pravastatin for 24 hours and the conditioned media was assayed for sFlt-1. (C) HUVEC cells were treated with 0.1 uM, 1 uM and 10 uM Hemin under vehicle or VEGF-E stimulation for 24 hours. The conditioned media was collected and assayed for sFlt-1 by ELISA.

Figures 2A, 2B, 2C:
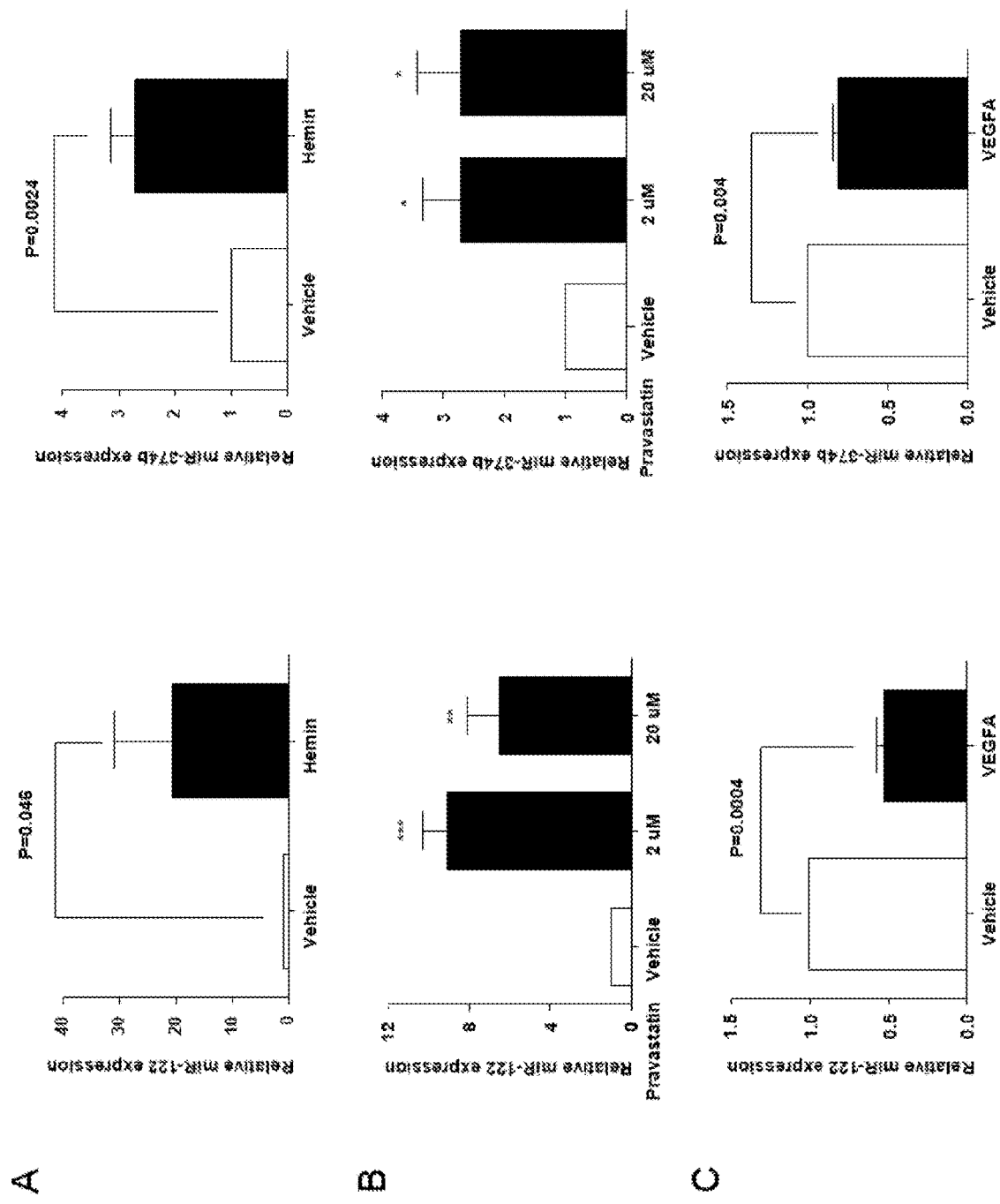
Figure 2D:
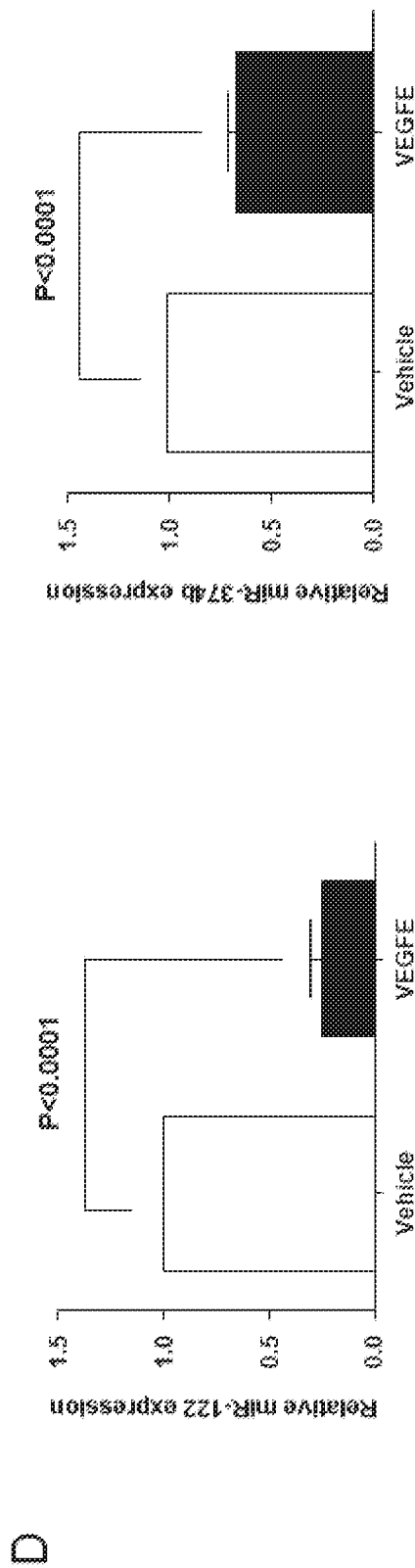

FIG. 2. MiR-122 and miR-374b are regulated by various agents that regulate sFlt-1 release. HUVEC cells were treated with 10 uM Hemin (A), 2 uM or 20 uM Pravastatin (B) 20 ng/ml VEGF-A (C) or 20 ng/ml VEGF-E (D) for 24 hours. Total RNA of the treated cells was isolated and the expression of miR-122 and miR-374b was measured by quantitative PCR. The relative miR-122 and miR-374b expression was normalized to RNU6.

FIG. 3. Hmox1 regulates miR-122 and miR-374b expression. HUVEC cells were infected by adenovirus overexpressiong Hmox1 (A) or transfected with siRNA against Hmox1 (B) for 24 hours and the relative expression of miR-122 and miR-374b was measured by qPCR.

FIG. 4. MiR-122 and miR-374b directly regulates sFlt-1 release in endothelial cells. (A) The diagrams show the seed sequence of miR-122 and miR-374b and the according targeting sites in the 3'-UTR of sFlt-1 mRNA. (B) HUVEC cells were electroporated with mimic miR-122 and miR-374b and rested for 24 hours. Transfected cells were then incubated in conditioned media with or without VEGF-E (20 ng/ml) for 24 to 48 hours and the media was assayed for ELISA against sFlt-1. (C) HUVEC cells were electroporated with antagomir of miR-122 and miR-374b and rested for 24 hours. Transfected cells were then incubated in conditioned media with or without pravastatin (20 uM) for 24 hours and the media was assayed for ELISA against sFlt-1. (D) HUVEC cells were electroporated with siHO-1, miR-122 or mi-374b separately or in combination. The transfected cells were then stimulated under vehicle or VEGF-E (20 ng/ml) in conditioned media and assayed for sFlt-1 release by ELISA.

FIG. 5. MiR-122 and miR-374b are decreased both in human severe preeclampsia patients and RuPP mouse model of preeclampsia and negatively correlates with blood pressure in RuPP mice. (A) Placenta samples of term severe preeclampsia patient (N=9-10) and control term pregnant women (N=9-10) have been collected and assayed for relative expression of miR-122 and miR-374b by qPCR. (B) The pregnant Sprague Dawley rats were undergone reduced uterine perfusion pressure (RUPP) surgery and the placenta tissue was collected at term. The expression of microRNA-122 in the placenta of sham control (N=11-12) and RuPP (N=11-12) rats was assayed by quantitative PCR. Data is shown as mean+SEM and analyzed by Student t-test. The relative miR-152 expression was normalized to RNU6. (C) Line graph showing the inverse correlation between mean arterial pressure (MAP) and the expression of miR-122 or miR-374b in the placenta in RuPP mice (N=6). The correlation was calculated by the Pearson's correlation coefficiency (Pearson's correlation r=−0.8101, P=0.05 and r=−0.8451, P=0.034). The relative expression of miR-122 and miR-374b in the placenta of RuPP mice was examined by quantitative.

FIG. 6. Synthetic microRNA-122 and 374b mimic (B, mi-122 and miR-374b) and antagomir (A, anti-122 and anti-374b) were electroporated into HUVEC cells and the relative miR-122 and miR-374b expression was measured by quantitative PCR.

Figures 7A, 7B:
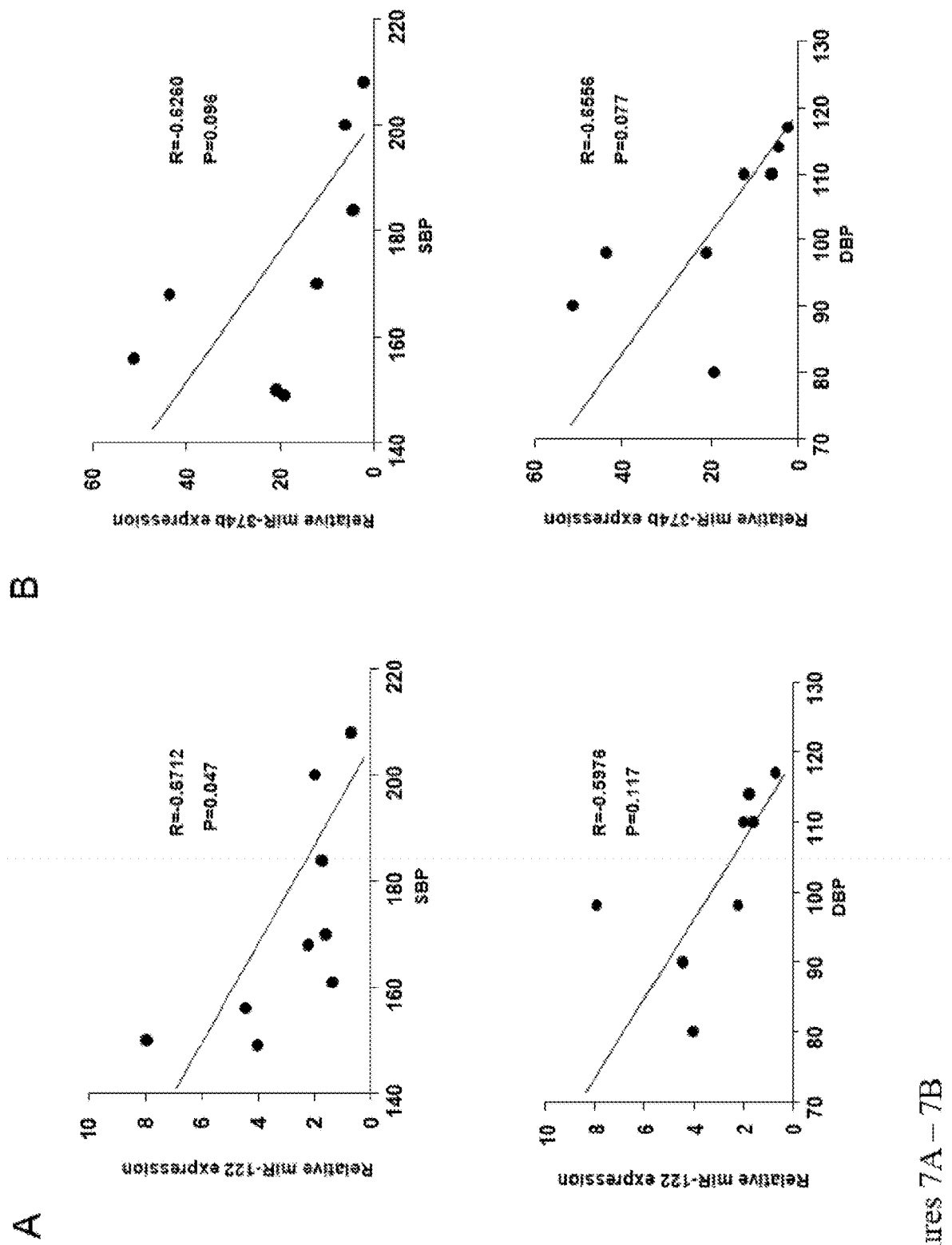

FIG. 7. Inverse correlations between miR-122 or miR-374b expression and systolic or diastolic blood pressure (SBP and DBP) in severe preeclampsia patients. Line graph showing the inverse correlation between SBP or DBP and the expression of miR-122 (A) or miR-374b (B) in the placenta in severe preeclampsia patients (N=8-9). The correlation was calculated by the Pearson's correlation. The relative expression of miR-122 and miR-374b in the placenta of severe preeclampsia patients was examined by quantitative.

Figures 16A, 16B:
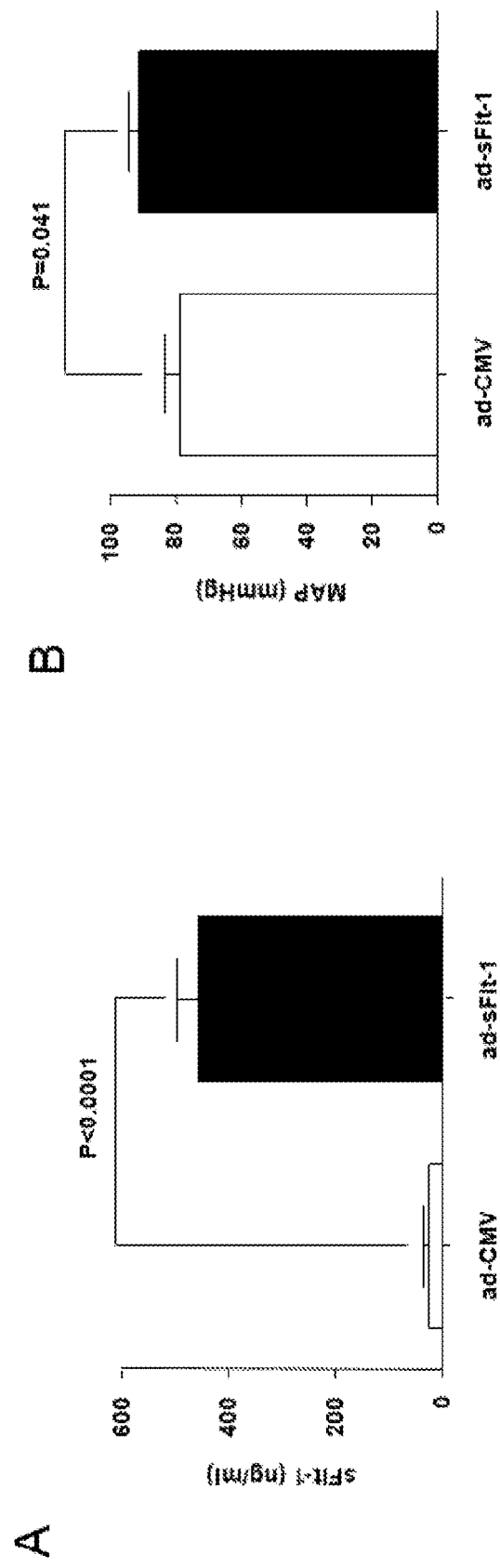

FIG. 8. The expression of miR-152 is increased in the placenta of women with severe preeclampsia and animal preeclamptic models. (A) The placenta samples of severe preeclampsia patients (PE, N=14) and the gestation age matched control patients (N=17) were collected and assayed for miR-152 expression using qPCR. (B) The pregnant Sprague Dawley rats were undergone reduced uterine perfusion pressure (RUPP) surgery and the placenta tissue was collected. The expression of microRNA-152 in the placenta of normal pregnant (N.P., N=12) and RuPP (n=17) rats was assayed by quantitative PCR. (C) The pregnant C57BL/6 mice were injected with $10^9$ PFU adenovirus, ad-CMV or ad-sFlt-1, at E 9.5 via tail vein injection. The sFlt-1 expression level in the circulation was measured using ELISA against Flt-1 and the mean artery pressure (MAP) was evaluated in the carotid artery at E 17.5 (FIG. 16). Placenta tissue from ad-CMV control virus (N=7) and ad-sFlt-1 virus (N=5) injected mice was collected and assayed for microRNA-152 expression using quantitative PCR. Furthermore, the expression of miR-152 was increased in intrauterine growth restriction (IUGR), obesity pregnant women and diabetic mouse model. (D) The expression of miR-152 in the placenta of IUGR (N=12) as well as in the gestation age matched control patients (N=17). (E, F) The expression of miR-152 in the visceral and subcutaneous fat of pregnant women with BMI over 30 (N=25 and 24 respectively) or with normal BMI (18-25) (N=22 for visceral and 20 for subcutaneous fat) was determined by qPCR. (G, H) miRNA-152 expression in the liver and mesenteric fat of db/db diabetic mouse and control mouse line was measured (N=5). Data is shown as mean+SEM and analyzed by Student t-test. The relative miR-152 expression was normalized to RNU6. ***$P<0.001$ vs $1^{st}$ trimester and # # $P<0.01$ vs $2^{nd}$ trimester placental samples.

FIG. 9 Hypoxia, inflammatory cytokine or angiogenic growth factor stimulation increases microRNA-152 expression in endothelial cells and placental explants. Human placental explants was treated with (A) inflammatory cytokine mix (TNF-α, 20 ng/ml, IFN-γ, 20 ng/ml and IL-1β, 2 ng/ml), (B) hypoxia (1% 02) condition or (C) combination of cytokine mix and hypoxia condition and assayed for miR-152 expression using qPCR. Similarly, HUEVC cells were treated with (D) hypoxia (1% 02) condition, VEGF-E (20 ng/ml, E) or FGF-2 (20 ng/ml, F) for 24 hours and used for qPCR analysis of miR-152 expression. Moreover, overexpression of miR-152 inhibited PlGF release, but not the sFlt-1 and sEng in endothelial cells. HUVECs were electroporated with mimic-152 or control mimic-con. After resting for 24 hours, the transfected cells were treated with vehicle or VEGF-E (20 ng/ml) in the conditioned media. The media was collected after 24 hours incubation and assayed for the sFlt-1 (G), sEng (H) and PlGF (I) concentration using ELISA. Data is shown as mean+SEM and analyzed by Student t-test.

FIG. 10. Blocking of miR-152 increased endothelial cell viability, but either inhibition or overexpression of miR-152 did not change endothelial cell proliferation or apoptosis. (A) HUVEC cells were electroporated with anti-152 (I) or mimic-152 (II). After overnight recovery, transfected cells were trypsinized and plated into 96-well plate with $1 \times 10^4$ per well under the vehicle or VEGF-A (20 ng/ml) treatment. After 48 hours, these cells were proceeded to MTT assay. (B) For cell proliferation, anti-152 (I) or mimic-152 (II) transfected HUVEC cells were plated in 24-well plate with $4 \times 10^4$ per well density and stimulated with VEGF-A (20 ng/ml) or VGEF-E (20 ng/ml). After 48 hours treatment, cells were trypsinized and the cell number per well was counted under microscope using a hemocytometer. Data is shown as mean+SEM and analyzed by Student t-test. (C) HUVEC cells were transfected with anti-152 (I) or mimic-152 (II) and rested for 24 hours. Cell lysates were blotted with antibody against cleaved caspase 3.

FIG. 11. miR-152 negatively regulates endothelial cell adhesive and angiogenic abilities. (A) HUVEC cells were electroporated with mimic-con or mimic-152 to overexpress miR-152. After 48 hours, $2 \times 10^4$ mimic-152 or mimic-con transfected cells were plated in the laminin (1 mg/ml), gelatin (2% solution) and collagen type I (0.1% solution) coated 96-well plate and treated with VEGF-A (20 ng/ml) or VEGF-E (20 ng/ml) for 30 minutes. Thereafter, cells were washed three times with PBS, stained with Calcein AM Fluorescent Dye and proceeded to fluorescent microscopy. Representative images were taken under the ×4 magnification and the number of the adhesive cells per field under the ×4 magnification was counted. Data was collected from at least 5 individual fields and shown as mean+SEM. Moreover, HUEVC cells were electroporated with mimic-152 (B) or anti-152 (C) and rested for 48 hours after transfection. Subsequently, the $1 \times 10^4$ transfected cells were plated on the Matri-gel coated 96-well plate under vehicle, VEGF-A (20 ng/ml) or VEGF-E (20 ng/ml) treatment. After incubation for 6-8 hours, the phase contrast images of the tubular-like structure were taken at ×4 magnification and the total tube length per ×4 field was quantified. Data was collected from at least 3-5 individual experiments and shown as mean+SEM.

FIG. 12. Overexpression of miR-152 attenuates revascularization in hind limb ischemia (HLI) mouse model. Male C57Bl/6 mice (3-4 month old) were injected intraterially with ad-CMV or ad-152 then subjected to HLI by surgical excising left femoral artery. (A) The relative expression of miR-152 in the control ad-CMV and ad-152 adenovirus injected gastrocnemius muscle was quantified by qPCR at day 3 (N=4 for both) and day 14 (N=11 for ad-CMV and N=9 for ad-152) after the surgery. (B) Blood flow perfusion was measured by LASER Doppler on plantar aspects of the feet of anesthetized mice. Blood flow recovery at day 0, day 4 and day 7 after surgery was calculated as a ratio of blood flow observed in left ischemic foot compared to right non-ischemic foot. *$P<0.05$. (C) Blood flow recovery at day 7 was calculated (N=11 for ad-CMV and N=9 for ad-152) and the representative images of blood flow perfusion are shown in right panel. Capillary density at day 14 after surgery was quantified in non-ischemic and ischemic gastrocnemius muscle by histological assessment, by isolectin B4 staining. The representative images (D) and quantification of capillary density (E, N=3 each) at day 14 in non-ischemia and ischemia gastrocnemius muscle were shown. (F) The relative expression of miR-152 in the non-ischemia and ischemia gastrocnemius muscle of ad-CMV injected mice (N=9 each) was measured by qPCR.

FIG. 13. Overexpression of miR-152 reduces fetal body weight and impairs vasculature in placenta of pregnancy mice. Female C57Bl/6 mice (3-4 month old) were injected intraperitoneally with $5 \times 10^9$ PFU ad-CMV or ad-152 at embryonic day 11.5 (E11.5) and the pregnancy was terminated and analyzed at embryonic day 17.5. (A) The expression of miR-152 in the plasma of ad-CMV and ad-152 injected mice was measured by qPCR. (B) The representative graph of foetus from mouse injected with ad-CMV or ad-152 at embryonic day 17.5 (E17.5). (C) The average fetal body weight in the C57Bl/6 mice injected intraperitoneally with ad-CMV (N=5) and ad-152 (N=5) was measured at embryonic day 17.5. (D) The representative graph showing the placentas from ad-CMV and ad-152 intraperitoneally injected mice. (E) Isolectin B4 and DAPI staining of haemotrichorial labyrinth zone in the placentas of mice injected with ad-CMV and ad-152 under the fluorescence microscope at 10× and 20× magnifications.

FIG. 14. MiR-152 directly targets ITGA5. (A) The diagram shows the seed sequence of miR-152 and the according targeting site in the 3'-UTR of ITGA5 mRNA. (B) HUVEC cells were electroporated with anti-152 or mimic-152 and rested for 48 h before treatment. The transfected cells were then stimulated with VEGF-A (20 ng/ml) for 1 h and Western blotted with antibodies against Neuropilin 1 (NRP1), caveolin-2 (CAV-2), fms-related tyrosine kinase 1 (Flt-1) and ITGA5. (C) HEK293 cells were transfected with pmiR-ITGA5 or pmiR-ITGA5M (mutation in the microRNA targeting site) together with mimic-con or mimic-152. The plasmid containing *renilla* luciferase gene was also transfected as the transfection control. After incubated for overnight, the relative luciferase activity was measured and normalized to the *renilla* activity. (D) Over-expression of ITGA5 rescued mimic-152 inhibited tube formation. HUEVC cells were infected with adenovirus of ITGA5 for overnight, then electroporated with mi-con or mi-152. After 24-48 hours, cells were trypsinized for Matri-gel tube formation assay. Fluorescence images were taken under phase contrast microscope at ×4 magnification and the total tube length per ×4 field was calculated. The over-expression of ad-ITGA5 was confirmed by western blot using an anti-ITGA5 antibody (insert).

FIG. 15. The ITGA5 expression is inversely correlated with miR-152 levels in mouse models and severe preeclampsia patients. (A) $2 \times 10^{12}$ GC of adeno-associated control virus (AAV-con) or miR-152 AAV virus were injected into adductor muscle of C57BL/6 mice and the muscle samples were collected after 4 weeks and western blotted for ITGA5 and GFP antibodies. The relative ITGA5 expression was calculated as a ratio of ITGA5 expression in AAV-152 injected muscle compared to AAV-con injected muscle (N=4 each). (B) The gastrocnemius muscle samples from Hind limb ischemia were blotted with antibody against ITGA5. The ratio of ITGA5 expression in the ischemic and non-ischemic muscle in ad-CMV (N=11) and ad-152 (N=9) injected mice was calculated. (C) The ITGA5 protein expression in the placenta of mice injected intraperitoneally with ad-CMV (N=4) and ad-152 (N=4) was examined by western blot. (D) The relative expression of miR-152 in the placenta of eight severe preeclampsia patients was examined by quantitative PCR and the corresponding ITGA5 protein expression was also determined by western blot using an anti-ITGA5 antibody. (E) Line graph showing the inverse correlation between the expression of miR-152 and ITGA5 levels in the placentas of severe preeclampsia patients. The correlation was calculated by the Pearson's correlation coefficiency from eight severe preeclampsia patient samples (Pearson's correlation r=−0.823, P=0.0121).

FIG. 16. The sFlt-1 expression and mean artery pressure (MAP) in the ad-sFlt-1 injected mice. The pregnant C57BL/6 mice were injected with 109 PFU adenovirus, ad-CMV or ad-sFlt-1, at E 9.5 via tail vein injection. (A) The sFlt-1 expression level in the plasma was measured using ELISA against Flt-1 in the plasma of ad-CMV (N=6) and ad-sFlt-1 (N=5) injected mice at E 17.5. (B) The mean artery pressure (MAP) was evaluated in the carotid artery in the ad-CMV (N=4) and ad-sFlt-1 (N=5) injected mice at E 17.5.

Figure 17A:
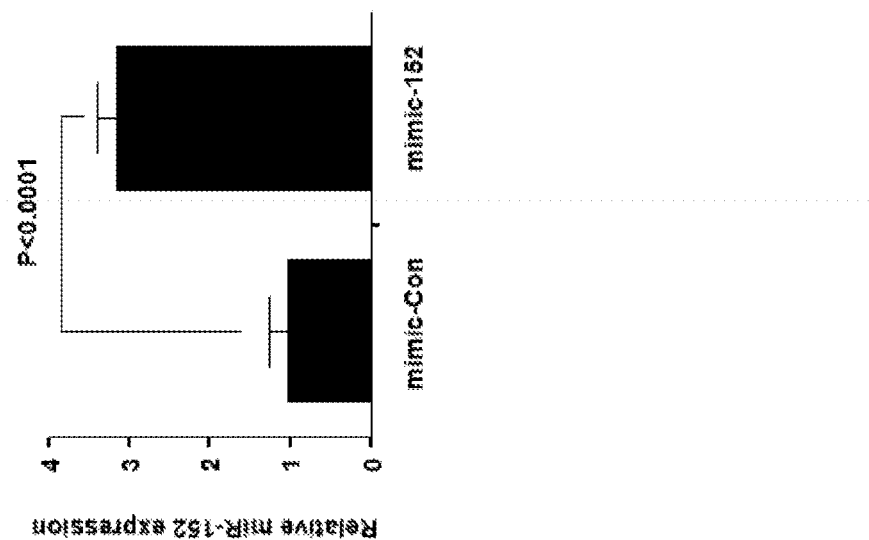
Figure 17B:
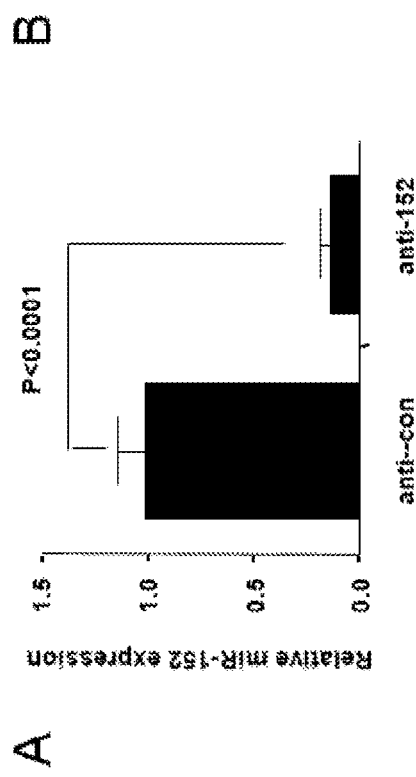

FIG. 17. Synthetic microRNA-152 antagomir (A, anti-152) and mimic (B, mimic-152) were electroporated into HUVEC cells and the relative miR-152 expression was measured by quantitative PCR.

Figure 18A:
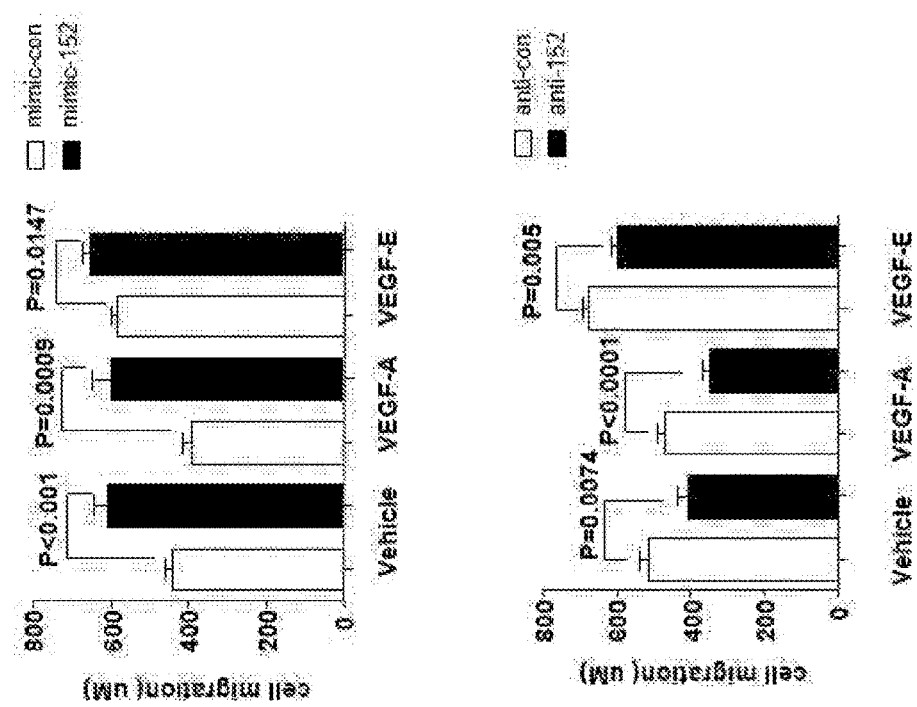
Figure 18B:
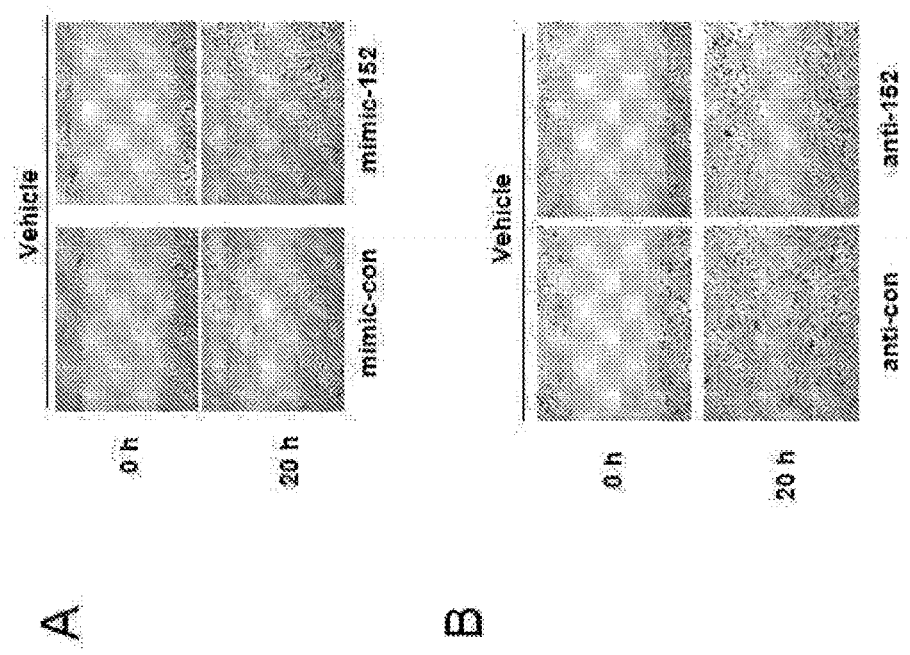

FIG. 18. MiR-152 positively regulates HUVEC cell migration. HUEVC cells were electroporated with anti-microRNA-152 (A) or mimic-152 (B). After 48 hours recovery, the scratch was made in the centre of the transfected confluent cells in a 12- or 6-well plate. The width of the scratches was measured immediately at 0 and 16-20 hours after the scratches were generated. The cell migration distance was calculated by subtracting the width of scratches at 0 and 16-24 hours. Data was collected from at least 4-5 wells and three random areas from each scratch were measured under microscope.

Figure 19A:
Figure 19B:
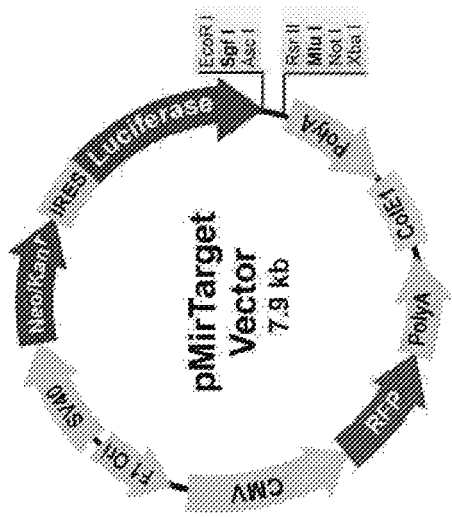

FIG. 19. (A) The diagram of pMirTarget plasmid used for the microRNA target validation. (B) The expression of red fluorescent protein (RFP) in the HUEVC cells transfected with pmir-ITGA5 plasmid.

Figures 20A, 20B, 20C:
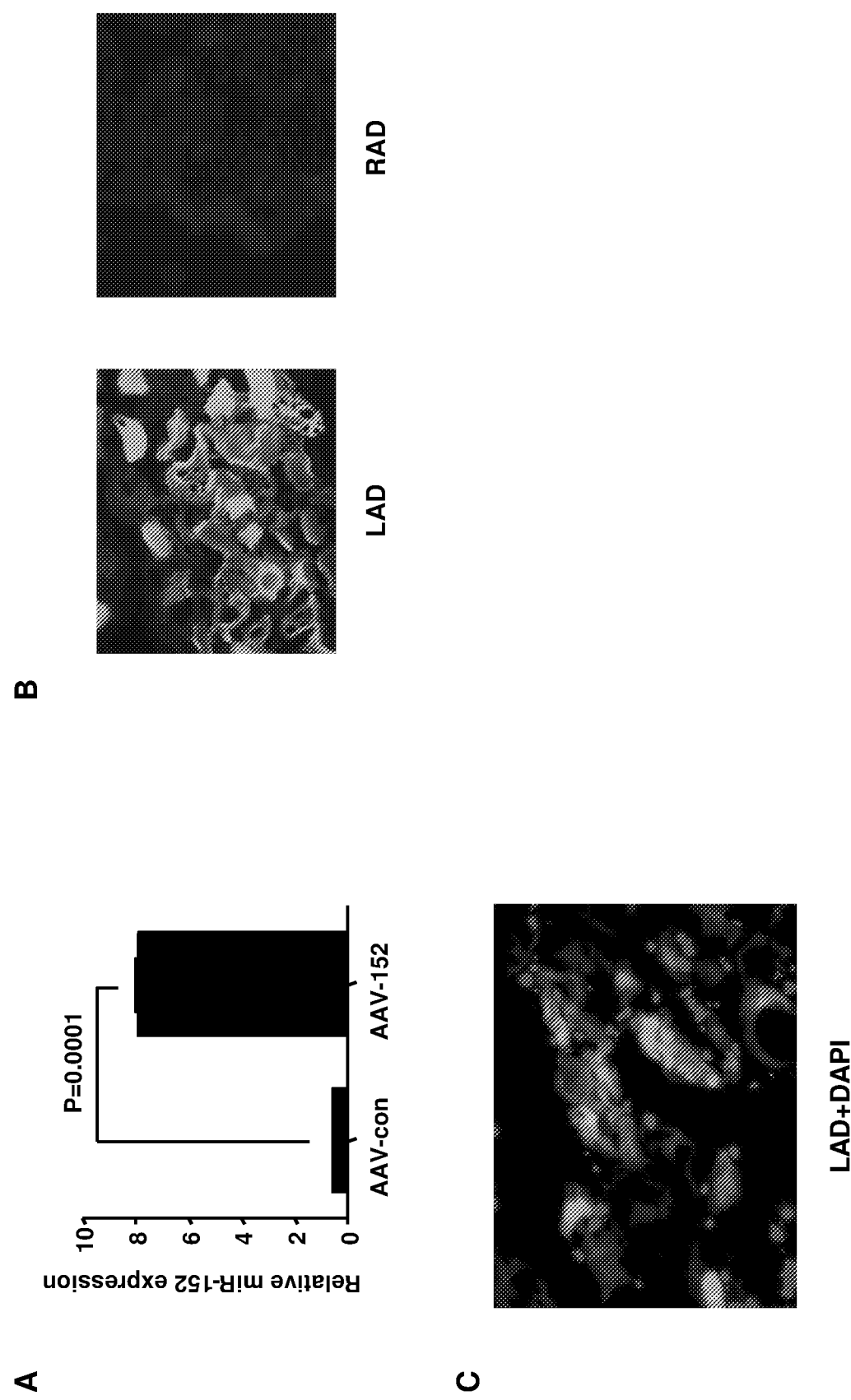

FIG. 20. The expression of miR-152 in AAV-152 infected C57BL/6 mouse. $2 \times 10^{12}$ GC of AAV-con or AAV-152 per animal were injected locally into the left side adductor (LAD) muscle and the same volume saline solution was injected into the right side (RAD) as control. After 4 weeks, the adductor muscle from both left and right side was collected and each sample was separated into two parts for qPCR analysis, western blotting and frozen sectioning. (A) The expression of miR-152 in the adductor muscle injected with AAV1-con and AAV1-152 after 4 weeks was assayed by quantitative PCR. (B) The frozen muscle samples of LAD and RAD were cut into 5 uM sections with a cryostat and the images of GFP expression were taken at ×20 magnification using a fluorescence microscope. (C) The representative image of GFP and DAPI overlapping in the LAD muscle.

Figure 25:
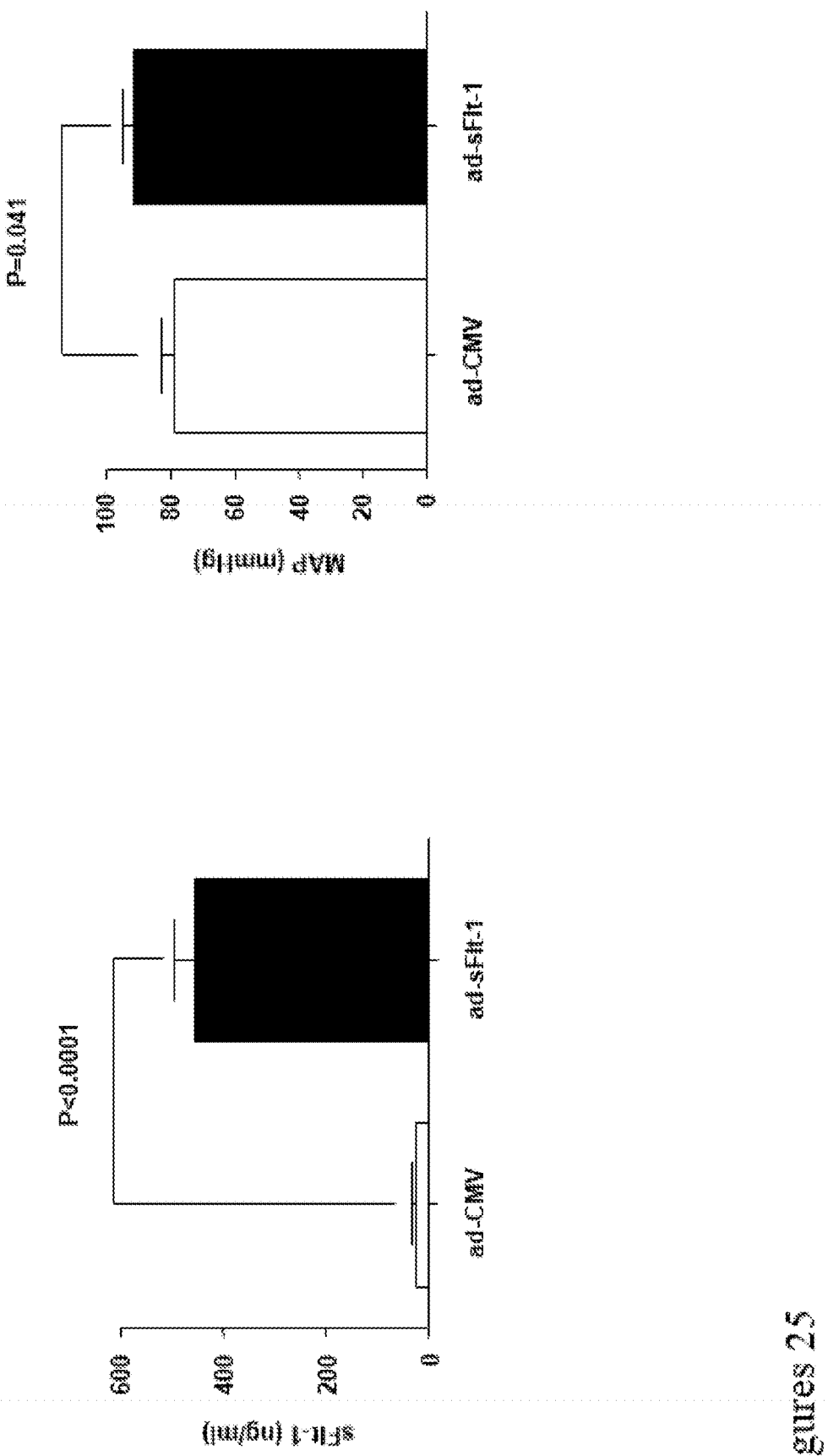

FIG. 21. The expression of miR-195 is increased in the placenta of women with severe preeclampsia and animal preeclamptic models. (A) Placenta tissue from pregnant women of 1st trimester (N=6), 2nd trimester (N=6) and 3rd trimester (N=4) was collected and measured for relative miR-195 expression by qPCR. Furthermore, the expression of miR-195 in the visceral (B) and subcutaneous fat (C) of pregnant women with BMI over 30 (N=25 and 24 respectively) or with normal BMI (18-25) (N=22 for visceral and 20 for subcutaneous fat) was determined by qPCR. (D) The expression of miR-195 was measured in the placenta of severe preeclampsia (N=14), IUGR (Intrauterine growth restriction, N=12) as well as in the gestation age matched control patients (N=17). (E) The pregnant C57BL/6 mice were injected with $10^9$ PFU adenovirus, ad-CMV or ad-sFlt-1, at E 9.5 via tail vein injection. The sFlt-1 expression level in the circulation was measured using ELISA against Flt-1 and the mean artery pressure (MAP) was evaluated in the carotid artery at E 17.5 (FIG. 25). Placenta tissue from ad-CMV control virus (N=7) and ad-sFlt-1 virus (N=5) injected mice was collected and assayed for miR-195 expression using qPCR. (F) The pregnant Sprague Dawley rats were undergone reduced uterine perfusion pressure (RUPP) surgery and the placenta tissue was collected. The expression of miR-195 in the placenta of normal pregnant (N.P., N=12) and RuPP (n=17) rats was assayed by qPCR. Moreover, inflammatory cytokine mix alone or in combination with hypoxia increases microRNA-195 expression in endothelial cells and placental explants. (G, H) HUEVCs were stimulated with Inflammatory cytokine mix (TNF-α, 20 ng/ml, IFN-γ, 20 ng/ml and IL-1β, 2 ng/ml) alone or in combination with hypoxia (1% O2) for 12-24 h and the expression of miR-195 was measured by qPCR. (I) Placenta explants were treated with Inflammatory cytokine mix in combination with hypoxia (1% O2) and the expression of miR-195 was measured by qPCR.

FIG. 22. microRNA-195 negatively regulates endothelial cell proliferation, viability, adhesive ability and angiogenesis. (A) HUVECs were electroporated with mi-con or mi-195 and treated under vehicle or VEGF-A (20 ng/ml) for 24 h. Medium supernatant was collected for ELISA assay against PlGF and data was generated from three independent experiments. (B) HUEVCs were transfected with mi-195 and plated in 24-well plate with stimulation of VEGF-A (20 ng/ml) or VGEF-E (20 ng/ml). After 48 h treatment, cells were trypsinized and the cell number per well was counted under microscope using a hemocytometer. (C) HUEVC cells were electroporated with mi-195 and plated into 96-well plate with $1\times10^4$ per well under the vehicle or VEGF-A (20 ng/ml) treatment. After 48 h incubation, cells were used for MTT assay. (D) HUVEC cells were electroporated with mi-195 or control mi-con. After 48 h, $2\times10^4$ mi-195 or mi-con transfected cells were plated in the 2% gelatin coated 96-well plate and treated with VEGF-A (20 ng/ml) or VEGF-E (20 ng/ml) for 30 mins. Subsequently, cells were washed three times with PBS, stained with Calcein AM Fluorescent Dye and proceeded to fluorescent microscopy. The number of the adhesive cells per field under the 10× magnification was counted. Data was collected from at least 5 individual fields. (E) HUEVC cells were electroporated with mi-195 and rested for 48 h. Thereafter, $1\times10^4$ transfected cells were plated in the matri-gel coated 96-well plate under vehicle, VEGF-A or VEGF-E treatment. After incubation for 6-8 h, images of the tubular-like structure were taken for quantitative analysis.

FIG. 23. microRNA-195 increases HUVEC cell migration. HUEVC cells were electroporated with antagomir anti-195 (A) or mimic mi-195 (B) and rested for 24-48 h to reach confluence. The scratch was made in the centre of the wells of transfected confluent cells in a 12- or 6-well plate. The width of the scratches was measured immediately at 0 h and 16-24 h after the scratches were generated. The cell migration distance was calculated by subtracting the width of scratches at 0 h and 16-24 h. Data was collected from at least 4-5 wells and three random areas from each scratch were measured under microscope.

FIG. 24. miR-195 directly targets eNOS. (A) The diagram shows the seed sequence of human miR-195 and the according targeting site in the 3'-UTR of eNOS mRNA from different species. (B) HEK293 cells were transfected with pmiR-eNOS or pmiR-eNOSM (mutation in the microRNA targeting site) together with mi-con or mi-195. The plasmid containing *renilla* luciferase gene was co-transfected as control. After incubated for overnight, the relative luciferase activity was measured and normalized to the *renilla* control activity. (C) HUVECs were transfected with mi-con or mi-195 and total RNA was isolated for qPCR analysis. The expression of eNOS mRNA was measured using primers against eNOS coding sequence. (D) HUVECs were electroporated with mi-con or mi-195 and recovered for 48 h before treatment. After 48 h, cells were stimulated with VEGF-A (20 ng/ml) for 1 h and Western blotted with anti-phosphor-eNOS and total eNOS antibodies. (E) The relative expression of phosphor-eNOS and total eNOS was quantified using Image J. (F) HUEVCs were infected with ad-195 (MOI=100) and assayed for nitric oxide release using a Sievers NO chemiluminescence analyzer. (G) Overexpression of eNOS rescued mi-195 mediated decrease of tube formation. HUEVCs were infected with adenovirus of ad-eNOS (MOI=50) for overnight and subsequently electroporated with mi-con or mi-195. After 24-48 h, cells were trypsinized for matri-gel tube formation assay. The phase contrast images of the tubular-like structure were taken after incubation for 6-8 hours at ×4 magnification. (H) The total tube length per ×4 field was quantified by Image Pro Plus software. Data was collected from at least 3-5 individual experiments and shown as mean+SEM.

FIG. 25. The sFlt-1 expression and mean artery pressure (MAP) in the ad-sFlt-1 injected mice. The pregnant C57BL/6 mice were injected with $10^9$ PFU adenovirus, ad-CMV or ad-sFlt-1, at E 9.5 via tail vein injection. (A) The sFlt-1 expression level in the plasma was measured using ELISA against Flt-1 in the plasma of ad-CMV (N=6) and ad-sFlt-1 (N=5) injected mice at E 17.5. (B) The mean artery pressure (MAP) was evaluated in the carotid artery in the ad-CMV (N=4) and ad-sFlt-1 (N=5) injected mice at E 17.5. Data is shown as mean+SEM and analyzed by unpaired t-test.

FIG. 26. The expression of miR-195 in HUVECs transfected with synthetic antagomir (anti-195) or mimic (mi-195) of microRNA-195 or infected with adenovirus overexpressing miR-195 (ad-195). (A) The efficiency of synthetic anti-195 and mi-195 was determined by quantitative PCR. Anti-195 significantly reduced, while mi-195 increased microRNA-195 expression in transfected HUVEC cells. (B) HUVECs were infected with ad-195 with a MOI of 100. The expression of miR-195 was measured by real-time quantitative PCR and compared to the control adenovirus infected cells.

Figures 27A, 27B:
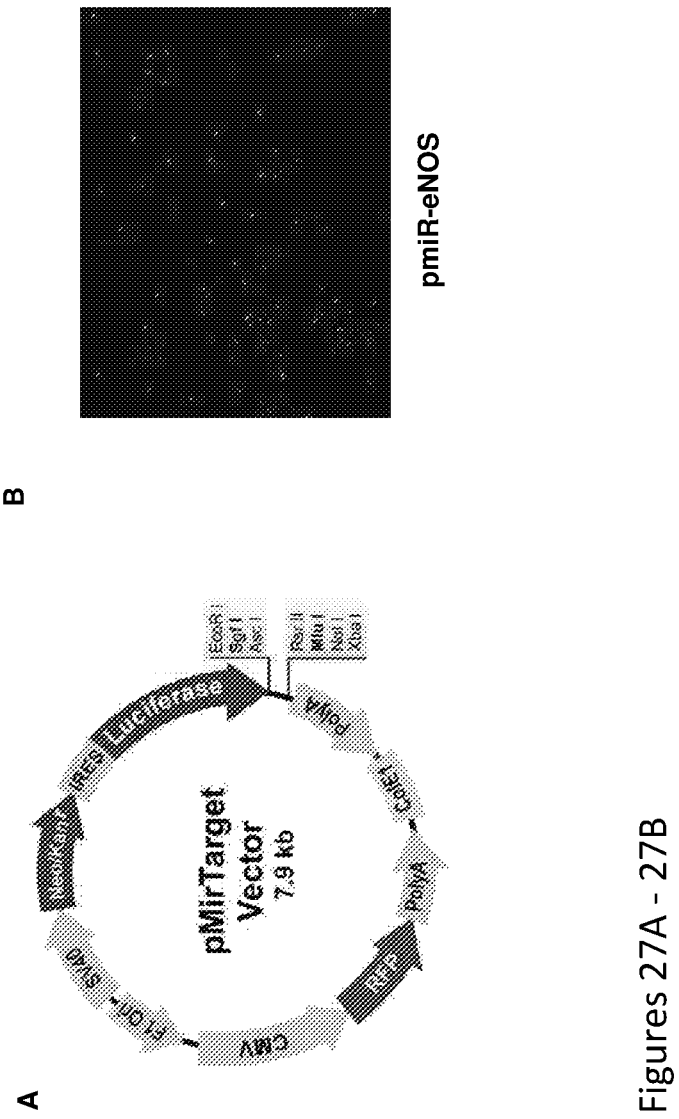

FIG. 27. (A) The diagram of pMirTarget plasmid used for the microRNA target validation. (B) The expression of red fluorescent protein (RFP) in the HUEVC cells transfected with pmir-eNOS plasmid.

MIR-122 AND MIR-374B

Methods and Materials:
Reagents and Chemicals

Recombinant growth factors, vascular endothelial growth factor A (VEGF-A), VEGF-E were purchased from RELIATech (Brauschweig, Germany). Hemin and pravastatin were purchase from Sigma-Aldrich (USA). M199 medium was purchased from Invitrogen (Paisley, UK).

Quantitative PCR primer against miR-122 and mir-374b, gScript™ microRNA cDNA and Synthesis PerfeCTa® SYBR® Green SuperMix Kit were purchased from Quanta Biosciences.
Human Placental Tissue Collection and Preparation Institutional Ethics Committee approved the placental tissue collection and written informed consent was obtained. All women were followed prospectively from enrolment until delivery. Human placental tissues were collected from women with pregnancy complicated by preeclampsia (N=14) and Intrauterine growth restriction (IUGR, N=12), and from normotensive pregnant women (N=17). The placental tissues collected were further used for quantitative PCR and western blot. Preeclampsia was defined as blood pressure >140/90 mm Hg on at least two consecutive measurements and maternal proteinuria of at least 300 mg/24 h and IUGR was defined as a foetus with estimated weight below the 10th percentile for its gestational age and abdominal circumference below the 2.5th percentile.
Reduced Uterine Perfusion Pressure (RUPP) Rat Model of Preeclampsia Placenta samples of RUPP preeclamptic model were a gift from Dr. Fergus McCarthy (Cork University Maternity Hospital, Wilton, Cork, Ireland). The experimental procedure and the characterization of rat undergone RUPP surgery were described previously (McCarthy et al., 2011).
Cell Culture Human umbilical vein endothelial cells (HUVECs) were isolated and cultured in M199 medium as described previously (Bussolati et al, 2001). Experiments were performed on third or fourth passage HUVEC.

PCR-Based microRNA Microarray

MicroRNA expression profiling in HUVEC cells stimulated with hemin was determined using a qPCR based array system. HUVEC cells were treated with 10 uM Hemin for 24 hours and the total RNA was isolated for Human miFinder RT$^2$ miRNA PCR Array (Qiagen, Cat. No. 331211). The PCR procedure and result analysis were performed according to manufacturer's instruction.

miRNA Mimic and Inhibitor Against miR-122 and miR-374b

Figures 6A, 6B:
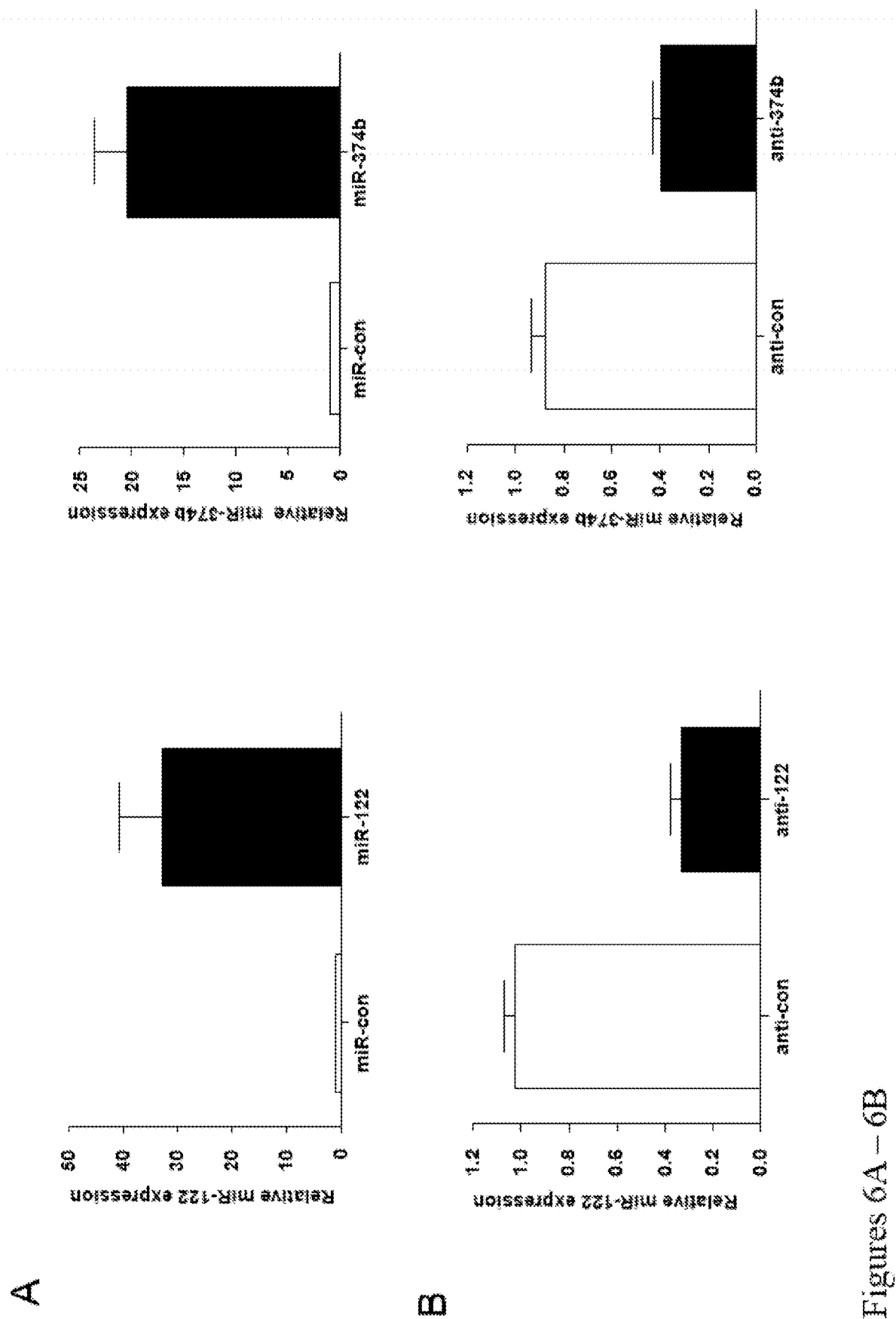

Chemically synthesized double-stranded microRNA mimic and single-stranded inhibitor against miR-122 (mi-122 and anti-122) and miR-374b (mi-374b and anti-374b) were purchased from Qiagen and the efficiency was tested by Qper (FIG. 6A, B). HUVECs were trypsinized, and $1\times10^6$ cells were electroporated with ≈0.6 ug mimic-122 or mimic-374b, ≈3 ug anti-122 or anti-374 or control molecules using electroporation (Amaxa GmbH, Cologne, Germany) as described previously (Cudmore et al., 2007).

Adenoviral Gene Transfer

The recombinant, replication-deficient adenovirus-encoding rat HO-1 (AdHO-1) was used as described previously (Cudmore et al., 2008).

siRNA Against Hmox1

The siRNA against Hmox1 was described previously (Cudmore et al., 2008).

Real-Time Polymerase Chain Reaction

Sample preparation and real-time quantitative PCR was performed as described previously (Cudmore et al., 2007).

Enzyme-Linked Immunosorbent Assay

Enzyme-linked immunosorbent assay (ELISA) kits for human sFlt-1 was obtained from R&D Systems and performed according to the manufacturer's specifications.

microRNA Target Assay

The plasmid containing 3'UTR of sFlt-1, pmiR-Flt1, was ordered from GeneCopoeia (Cat No. HmiT054531-MT01, MD, USA). The firefly luciferase cDNA was fused with 3'UTR of sFlt-1 and the control *renilla* luciferase gene was driven by CMV promoter in the same plasmid. The mutant plasmids containing miR-122 and miR-374b binding sites, pmiR-Flt1-M1 and pmiR-Flt1-M2, were generated using site directed mutagenesis technique. The binding site of miR-122 was mutated from "TTTGTAGCATTGTCAT-CACTCCT (SEQ ID NO:9)" to "TTTGTCGACGGATA-GAGAAT (SEQ ID NO:10)". The two binding sites of miR-374b were mutated from "GTCAAAATAGATTAT-TATAA (SEQ ID NO:11)" to "GTCAAGAGCAAGGCGCA (SEQ ID NO:12)" and from "TACAATATTTGTACTAT-TATAT (SEQ ID NO:13)" to "TACAATATTTA-GACGCGCT (SEQ ID NO:14)".

For microRNA target assay, HEK293 cells were transfected with pmiR-ITGA5 or pmiR-ITGA5M together with mimic-con or mimic-152. After overnight incubation, the relative firefly luciferase activity was measured and normalized to the *renilla* activity according to the manufacture's protocol of Dual-Luciferase® Reporter Assay System (E1910, Promega).

microRNA Target Prediction

The direct targets of miR-122 and miR-374b were predicted using online programs, microRNA.org (microrna.org/microrna/home.do), PicTar (pictar.mdc-berlin.de/) and Target Scan (targetscan.org/).

Statistical Analysis

All data are expressed as mean+S.E.M. Statistical comparisons were performed using Student's t-Test or Mann-Whitney U test. Statistical significance was set at a value of $p<0.05$.

Results:

Identification of microRNAs Responding to Hemin Stimulation Using Microarray

Our previous study showed that the release of sFlt-1 in endothelial cells can be regulated by vascular endothelial growth factor (VEGF) and heme oxygenase 1 (Hmox1) (Cudmore et al., 2007; Ahmad et al., 2011). However the molecular mechanisms underlie the sFlt-1 regulation is unclear. Thus we hypothesized that microRNAs may be regulated in the downstream of VEGF or Hmox1 and directly target sFlt-1 mRNA translation. The pilot study confirmed our previous observation that VEGF-E significantly induced sFlt-1 release from endothelial cells (FIG. 1A), while statin, the potent Hmox1 inducer, decreased sFlt-1 level at both 2 uM and 20 uM (FIG. 1B). Furthermore another Hmox1 inducer, hemin, decreased sFlt-1 release as expected at 10 uM in endothelial cells and this reduction cannot be recovered by stimulation of VEGF-E, implying VEGF-E and hemin are individual regulators of sFlt-1 (FIG. 1C).

To identify the microRNAs that respond to hemin stimulation, a qPCR-based microarray was performed using RNA samples isolated from hemin treated HUVEC cells. Briefly, HUVEC cells were treated with 10 uM Hemin for 24 hours and the total RNA was isolated for Human miFinder RT2 miRNA PCR Array (Qiagen, Cat. No. 331211). The results were analyzed using the programme provided by manufacture and the differently expressed microRNAs upon Hemin treatment were determined. In summary, there are 24 up-regulated and 26 down-regulated microRNAs have been identified. To further select the microRNAs directly target sFlt-1, the up-regulated microRNAs were analyzed for the possibility of directly targeting sFlt-1 mRNA using online bioinformatic tools, including microRNA.org, PicTar and Target Scan. Finally, 3 microRNAs, miR-122, miR-144 and miR-374b, were predicted to be the ones directly target sFlt-1 and used for further study.

miR-122 and miR-374b Expression was Regulated by VEGF and Hmox1 Inducer

Since miR-122, miR-144 and miR-374b are predicted to be direct regulator of sFlt-1 and VEGF or Hmox1 inducers regulate sFlt-1 release, we tested whether these microRNAs can be regulated by VEGF or Hmox1 inducers. HUVECs were treated with hemin (10 uM), VEGF-A (20 ng/ml) or VEGF-E (20 ng/ml) and the expression of these microRNAs was determined by qPCR. Treatment with hemin increased miR-122 and miR-374b expression by 20-fold and 2.7-fold respectively (FIG. 2A), but had no significant effect on miR-144 expression (data not shown). Moreover, both 2 uM and 20 uM pravastatin stimulation significantly induced miR-122 and mir-374b expression by 3-9-fold and 2.7-fold respectively (FIG. 2B). Inversely, decreased miR-122 expression was decreased by 47% and 75% in VEGF-A and VEGF-E stimulation (FIG. 2C, D). The expression of miR-374b was reduced by 20% and 34% respectively upon VEGF-A and VEGF-E treatment (FIG. 2C, D).

Hmox1 Regulates miR-122 and miR-374b Expression

Figures 3A, 3B:
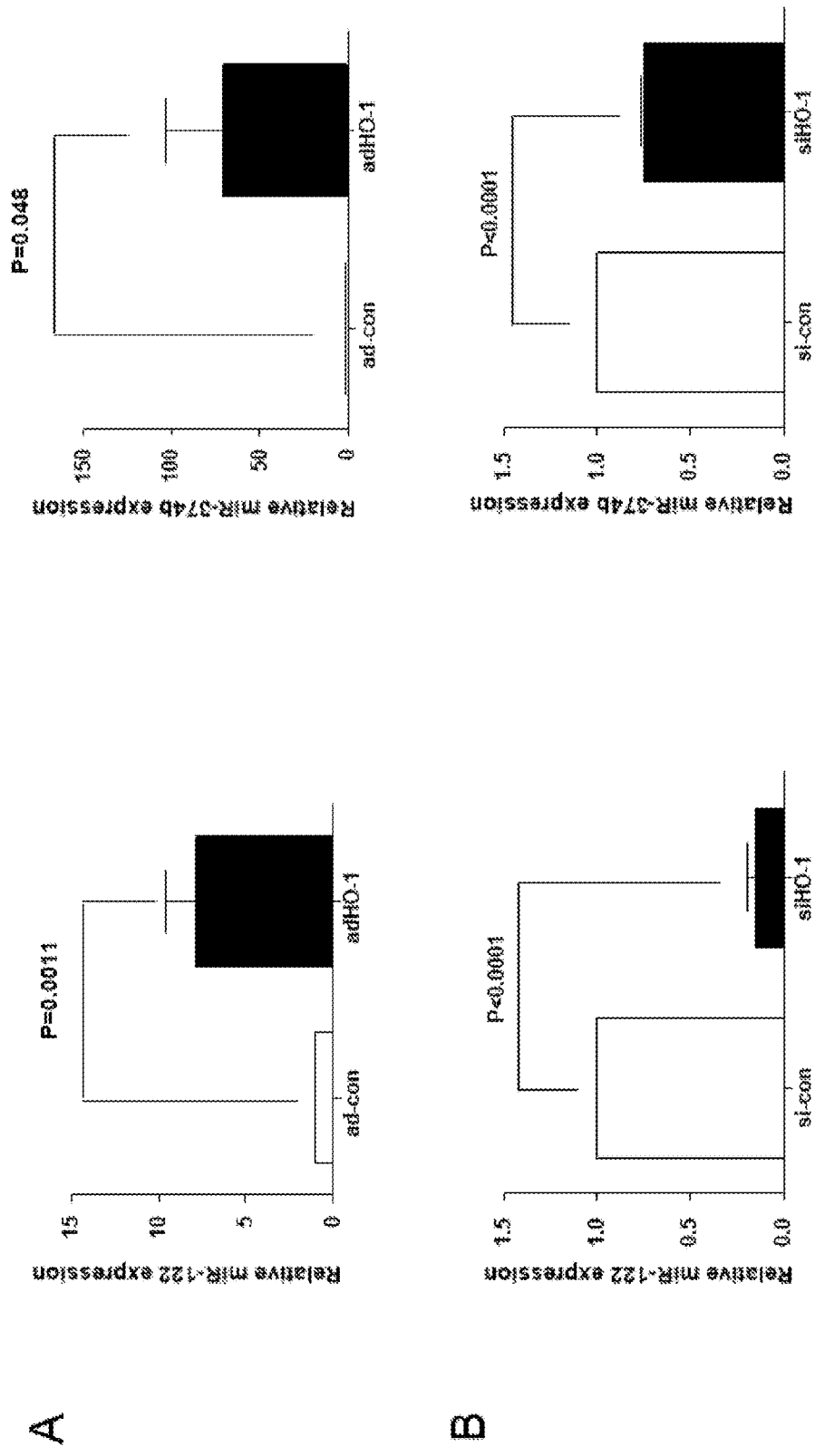

As Hmox1 inducers modulate miR-122 and miR-374b expression, we investigated whether these microRNAs can be regulated directly by Hmox1. HUVEC cells were infected with adenovirus overexpressing Hmox1 and the expression of miR-122 and miR-374b in these cells were quantified by qPCR. As expected, overexpression of Hmox1 increased miR-122 and miR-374 expression by 7.8-fold and 70-fold respectively (FIG. 3A), but the miR-144 expression was not changed. Conversely, HUVEC cells transfected with siRNA against Hmox1 showed decreased expression of miR-122 and miR-374b at 85% and 25% respectively (FIG. 3B).

MiR-122 and miR-374b Directly Target sFlt-1 mRNA

Figures 4C, 4D:
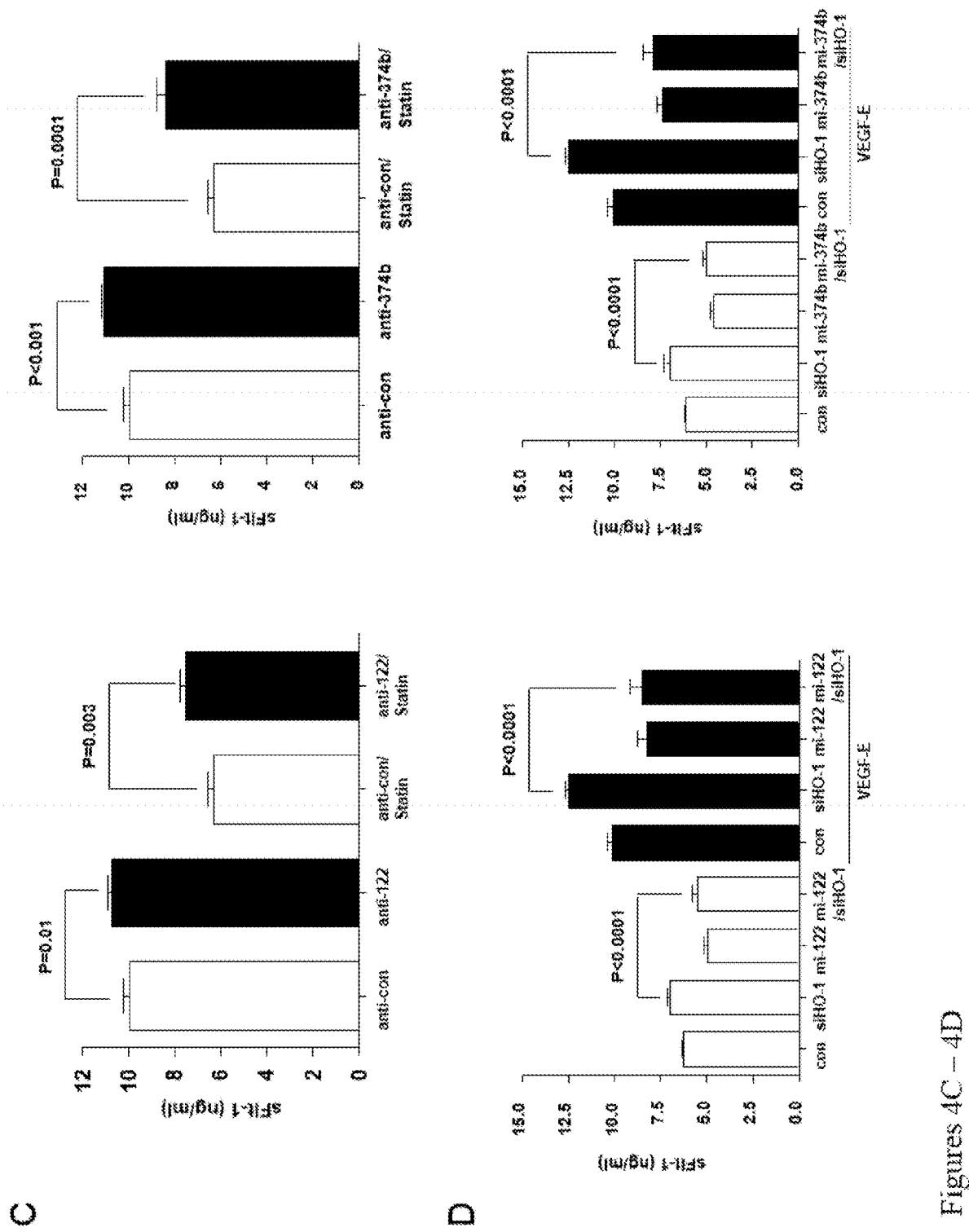

The previous bioinformatic analysis predicted that miR-122 and miR-374b can directly bind to the 3'-untranslated region (UTR) of sFlt-1 mRNA (FIG. 4A). To further confirm that sFlt-1 mRNA is directly targeted by these microRNAs, the luciferase assay using 3'-UTR of sFlt-1 and mimic of miR-122 (mi-122) or miR-374b (mi-374b) was performed. The plasmids containing 3'-UTR of sFlt-1 either with intact sequence or mutated sequence which the miR-122 and miR-374b binding sites have been modified were fused to the firefly luciferase and transfected into HEK293 cells. These cells were also co-transfected with mimic control, mi-122 and mi-374b alone or in combination. The luciferase activity assay revealed that mi-122 and mi-374b transfection significantly suppressed luciferase activity compared to mimic control transfected cells, while this suppression was not observed in the mutant plasmids containing modified microRNA binding sites (FIG. 4A). Interestingly, the combination of mi-122 and mi-374b did not reduce the luciferase activity further than the individual transfection of mi-122 or mi-374b (FIG. 4A). The targeting of sFlt-1 by miR-122 and mir-374b was confirmed additionally by ELISA measuring sFlt-1 in the culture medium of HUVECs transfected with mi-122 and mi-374b alone or in combination. The sFlt-1 level in the medium of HUVECs transfected with mi-122 or mi-374b was reduced around 30% compared to mimic control in the condition of both vehicle and VEGF-E stimulation (FIG. 4B). Reversely, HUVECs transfected with antagomir of miR-122 (anti-122) and miR-374b (anti-374b) released significantly more sFlt-1 into the medium especially in the condition of statin stimulation (FIG. 4C). More importantly, these microRNAs act in the downstream of Hmox1 to target sFlt-1 expression. HUVECs were transfected with siHO-1 in combination with mi-122 or mi-374b and the sFlt-1 release was measured by ELISA. As expected, siHO-1 transfection significantly increased sFlt-1 expression, while co-transfection with mi-122 or mi-374b completely abolished this increase mediated by siHO-1 (FIG. 4D).

Implication of miR-122 and miR-374b in the Pathogenesis of Preeclampsia

Figures 5A, 5B:
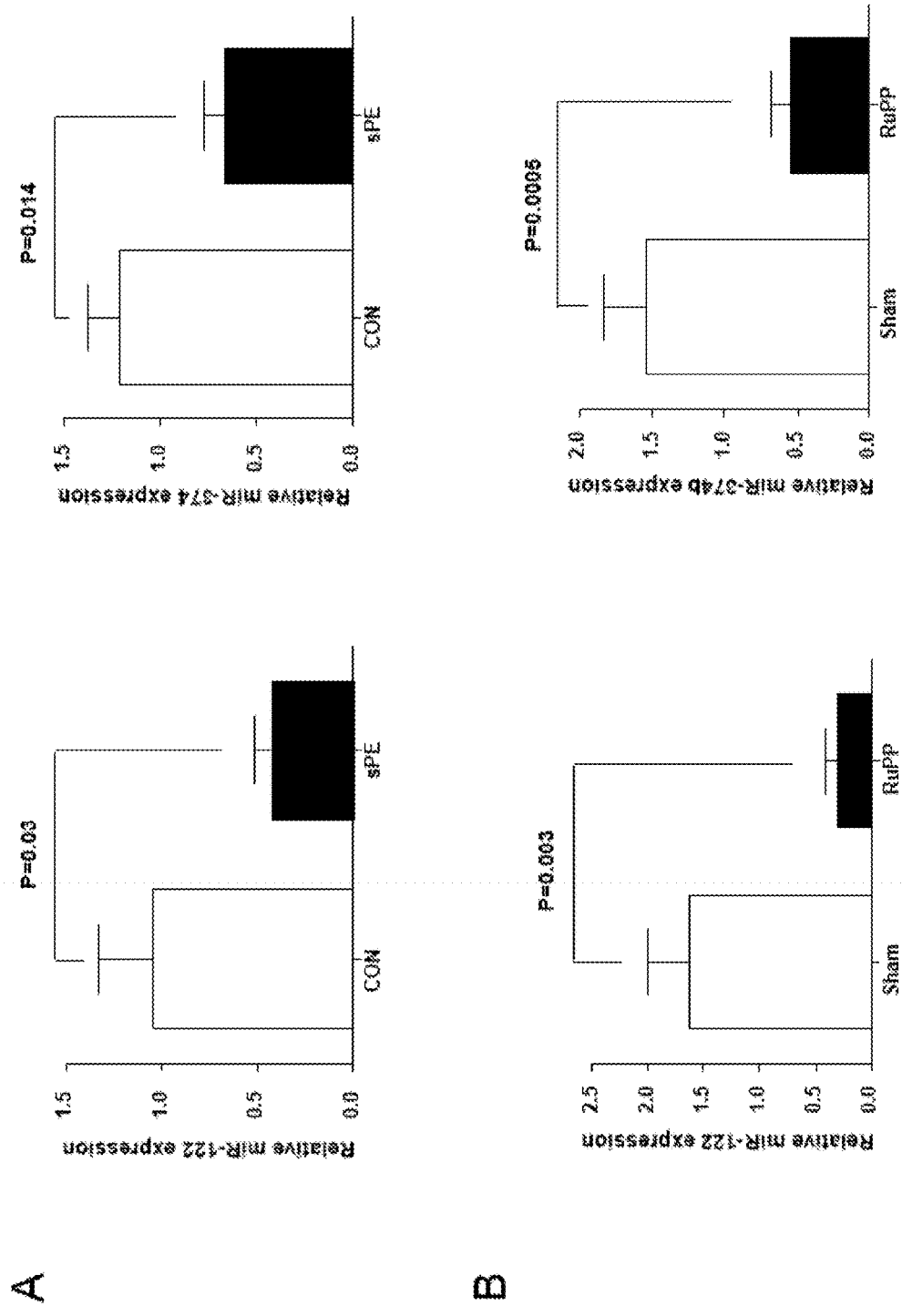
Figure 5C:
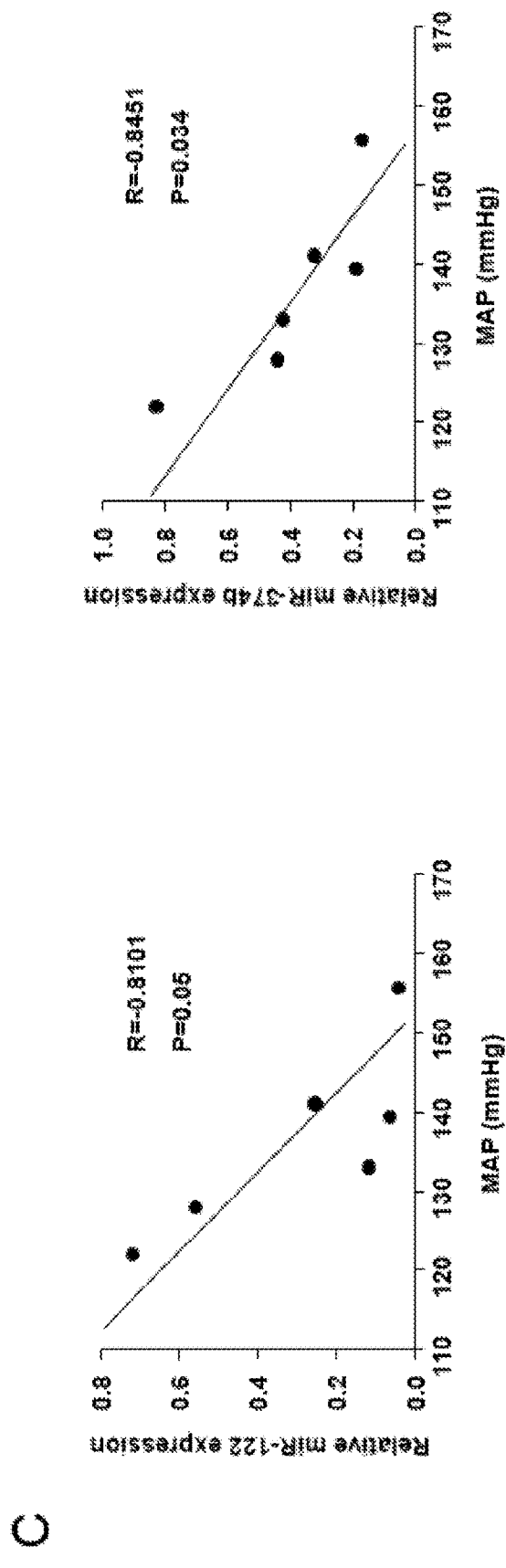

Since the angiogenic imbalance is the main cause of preeclampsia and sFlt-1 antagonists VEGF signalling pathway (Levine et al., 2004; Venkatesha et al., 2006; Ramma and Ahmed, 2011), we measured the expression of miR-122 and miR-374b by qPCR in the placenta of preeclamptic patients and RuPP preeclampsia mouse model. The expression of miR-122 and miR-374b in the preeclamptic placenta was decreased by around 60% and 45% respectively compared to age matched controls (FIG. 5A). Furthermore, their expression in the placenta of RuPP mice was decreased by about 81% and 64% respectively compared to sham control (FIG. 5B). More importantly, the expression of miR-122 and miR-374b was negatively correlated with the blood pressure in the RuPP mice (FIG. 5C, N=6, R=−0.81 and R=−0.845 respectively) and ad-sFlt-1 virus injected mouse model (FIG. 8, N=5, R=−0.9778 and R=−0.9397 respectively). Moreover, this correlation has been further confirmed in the severe preeclampsia patient. The expression of miR-122 and miR-374b in the placenta of severe preeclampsia patient was negatively correlated with their systolic and diastolic blood pressure (SBP and DBP) (FIG. 7, N=8-9).

miR-152

Methods and Materials:

Reagents and Antibodies

Recombinant growth factors, vascular endothelial growth factor A (VEGF-A), VEGF-E, tumor necrosis factor alpha (TNF-α), interferon gamma (IFN-γ) and interleukin 1 beta (IL-1β) were purchased from RELIATech (Brauschweig, Germany). Rabbit antibody against ITGA5, Caspase 3, Flt-1, CAV2 and NRP1 were obtained from Cell Signaling Technology (Danvers, Mass. 01923, United States). Mouse anti-β-Actin antibody and rabbit anti-GAPDH were obtained from Sigma-Aldrich (A5441, St. Louis, Mo., United States) and Santa Cruze Biotech respectively. Quantitative PCR primer against miR-152, gScript™ microRNA cDNA and Synthesis PerfeCTa® SYBR® Green SuperMix Kit were purchased from Quanta Biosciences. Growth factor reduced Matrigel purchased from Becton Dickinson (Oxford, UK). M199 medium was purchased from Invitrogen (Paisley, UK). Calcein AM Fluorescent Dye was purchased from BD Bioscience (P.O. Box 999 Sparks, Md., USA 21152). DyLight 594 labelled *Lycopersicon Esculentum* (Tomato) Lectin (LEL, TL) was purchased from Vector Laboratories (Burlingame, Calif. 94010). Alexa Fluor® 594 Conjugated Isolectin GS-IB4 was purchased from Life Technologies (Paisley, UK). OCT compound was purchased from VWR International Ltd. (Leicestershire, LE17 4XN, England).

Human Placental Tissue Collection and Preparation

Institutional Ethics Committee approved the placental tissue collection and written informed consent was obtained. All women were followed prospectively from enrolment until delivery. Human placental tissues were collected from women with pregnancy complicated by preeclampsia (N=14) and Intrauterine growth restriction (IUGR, N=11), and from normotensive pregnant women (N=17). The placental tissues collected were further used for quantitative PCR and western blot. Preeclampsia was defined as blood pressure >140/90 mm Hg on at least two consecutive measurements and maternal proteinuria of at least 300 mg/24 h and IUGR was defined as a foetus with estimated weight below the 10th percentile for its gestational age and abdominal circumference below the 2.5th percentile.

Cell and Placental Explants Culture

Human umbilical vein endothelial cells (HUVECs) were isolated and cultured in M199 medium as described previously (Bussolati et al, 2001). Experiments were performed on third or fourth passage HUVEC. First trimester placental tissues (6-9 weeks gestational age) were retrieved from normal pregnancies that had undergone elective termination. Placental villus tissue explants were prepared as described previously (Ahmad and Ahmed, 2004). Briefly, human placental villus explants were incubated under stimulation of test substances or hypoxia condition and collected for quantitative PCR of miR-152. To create hypoxic condition, 70-80% confluent HUEVCs or placental explants were cultured in an incubator with 1% O2 and 5% $CO_2$ at 37° C.

miRNA Mimic and Inhibitor Against miR-152

Chemically synthesized double-stranded microRNA mimic and single-stranded inhibitor against miR-152 (mimic-152 and anti-152) were purchased from Qiagen. HUVECs were trypsinized, and $1\times10^6$ cells were electroporated with ≈0.6 ug mimic-152, ug anti-152 or control molecules using electroporation (Amaxa GmbH, Cologne, Germany) as described previously (Cudmore et al., 2007).

Adenovirus and Adeno-Associated Virus Animal Injection

Adenovirus, ad-sFlt-1, was a gift from Prof. Richard Mulligan (Harvard Medical School, Boston, USA). The ad-sFlt-1 and ad-CMV control virus were amplified and titered and $10^9$ PFU adenoviruses were injected into C57BL/6 mice at E 9.5 via tail vein to over-express sFlt-1.

Adeno-associated virus (serotype 1) over-expressing miR-152 (AAV-152) was generated and titered by Vector Biolabs (Philadelphia, USA). The GFP was fused with miR-152 cDNA as reporter gene. In the hind limb muscle injection, $2\times10^{12}$ GC of AAV1-con or AAV1-152 AAVs were injected locally into left side adductor muscle of C57BL/6 mice and the same volume saline solution was injected into the right side as control. The virus infection was confirmed by co-expressed GFP reporter protein and overexpression of miR-152 was determined in the muscle 4 weeks after injection by quantitative PCR (FIG. 20).

Reduced Uterine Perfusion Pressure (RUPP) Rat Model of Preeclampsia

Placenta samples of RUPP preeclamptic model were a gift from Dr. Fergus McCarthy (Cork University Maternity Hospital, Wilton, Cork, Ireland). The experimental procedure and the characterization of rat undergone RUPP surgery were described previously (McCarthy et al., 2011).

Real-Time Polymerase Chain Reaction

Sample preparation and real-time quantitative PCR was performed as described previously (Cudmore et al., 2007).

Western Blotting

Total protein from HUVECs or animal tissue was lysed in RIPA buffer and assayed as previously described (Ahmad and Ahmed, 2004).

Enzyme-Linked Immunosorbent Assay

Enzyme-linked immunosorbent assay (ELISA) kits for human sFlt-1, sEng and PlGF were obtained from R&D Systems and performed according to the manufacturer's specifications.

In Vitro Cell Adhesion Assay

HUVECs were electroporated with mimic-152 or control mimic-con. After 48 h, $2\times10^4$ mimic-152 or mimic-con transfected cells were plated in the 2% gelatin coated 96-well plate and treated with VEGF-A (20 ng/ml) or VEGF-E (20 ng/ml) for 30 mins. Thereafter, cells were washed three times with PBS, stained with Calcein AM Fluorescent Dye and proceeded to fluorescent microscopy. The number of the adhesive cells per field under the 4× magnification was counted.

In Vitro Tube Formation Assay

Formation of capillary-like structures of mimic-152, anti-152 or mimic-152 and ad-ITGA5 treated HUEVCs on growth factor reduced Matrigel was determined as previously described (Bussolati et al, 2001).

In Vitro Cell Viability and Proliferation Assay

HUVEC cells were electroporated with anti-152 or mimic-152. After overnight recovery, transfected cells were trypsinized and plated into 96-well plate with $1\times10^4$ per well under the vehicle or VEGF-A (20 ng/ml) treatment. After 48 h, these cells were proceeded to MTT assay using cell growth determination kit (CDG1, Sigma-Aldrich). For cell proliferation assay, transfected cells were plated in 24-well plate with $4\times10^4$ per well and stimulated with VEGF-A (20 ng/ml) or VGEF-E (20 ng/ml). After 48 h treatment, cells were trypsinized and the cell number per well was counted under microscope using a hemocytometer.

In Vitro Cell Migration Assay

HUEVC cells were electroporated with anti-152 or mimic-152. After overnight recovery, the scratch was made in the centre of the transfected confluent cells in a 12- or 6-well plate. The width of the scratches was measured immediately at 0 h and 16-24 h after the scratches were generated. The cell migration distance was calculated by subtracting the width of scratches at 0 h and 16-24 h.

Hind Limb Ischemia Mouse Model

Animal study protocols were approved by Aston University Ethical Review Committee and conducted in accordance with the United Kingdom Animals (Scientific Procedures) Act, 1986. Male C57Bl/6 mice (3-4 month old) were injected intraterially with ad-152 or ad-CMV then subjected to HLI by surgical excising left femoral artery as previously described (Murdoch et al., 2014). The left femoral artery was isolated. A temporary proximal ligation of both vein and artery was placed on before canulation and injection of ad-152 or ad-CMV into the left femoral artery. After 5 minutes two further ligations were added just to the artery at a proximal and distal location before excising approximately 1.5 mm. The temporary ligation to the vein was removed. Blood flow perfusion was measured by LASER Doppler (Moor Instruments UK) on plantar aspects of the feet of anesthetized mice (ketamine (100 mg/kg) xylazine (10 mg/kg); i.p.) as previously described (Murdoch et al., 2014). Blood flow recovery was calculated as a ratio of blood flow observed in left ischemic foot compared to right non-ischemic foot. Capillary density was quantified in non-ischemic and ischemic gastrocnemius muscle by histological assessment, by Isolectin B4 staining.

Mouse Pregnancy Study

Three to four month old C57BL/6 mice were mated. The first day of pregnancy (E0.5) was defined by the presence of a vaginal plug the following morning. Pregnant mice were randomly assigned into two groups at day E11.5 and injected intraperitoneally with ad-152 or ad-CMV with a dose of $5\times10^9$ PFU per mouse. After 6 days, the pregnant mice were mice were anesthetized using a Ketamine/Xylazine cocktail and subsequently sacrificed for sampling. The live foetuses and placentas were counted and weighed. Their blood was taken and kidneys, livers, spleens and placentas were collected. The expression of miR-152 was measured by qPCR in blood and placentas. The placental tissue was later stained with Isolectin B4 for analyzing of the placental vasculature.

microRNA Target Assay

The *Homo sapiens* cDNA containing untranslated region (UTR) of ITGA5 was purchased from Origene (Rockville, Md. 20850, USA) and the UTR region was subcloned into pMirTarget to generate ITGA5-UTR-Luciferase (firefly) expression plasmid, pmiR-ITGA5. The successful transfection of pmiR-ITGA5 in endothelial cells was validated by the expression of red fluorescent protein (RFP) (FIG. 20). The plasmid harbouring mutant on miR-152 and ITGA5-UTR binding site was generated using site-directed mutagenesis kit (Stratagene) with PCR primers containing the mutant site and the resulted plasmid was designated as pmiR-ITGA5M. The primers used for PCR amplification were mITGA5-F, TCCCTCCCCCCCATGCTGTGG (SEQ ID NO:15), and mITGA5-R, TGTAAACAAGGGTC-CACAGCA (SEQ ID NO:16).

For microRNA target assay, HEK293 cells were transfected with pmiR-ITGA5 or pmiR-ITGA5M together with mimic-con or mimic-152. The plasmid containing *renilla* luciferase gene was also transfected as the internal control. After overnight incubation, the relative firefly luciferase activity was measured and normalized to the *renilla* activity according to the manufacture's protocol of Dual-Luciferase® Reporter Assay System (E1910, Promega).

microRNA Target Prediction

The direct targets of miR-152 were predicted using online programs, microRNA.org (http://www.microrna.org/microrna/home.do), PicTar (http://pictar.mdc-berlin.de/) and Target Scan (targetscan.org/).

MicroArray Profiling

HUVEC cells were transfected with mimic-152 and the total RNA sample was collected for whole genome gene array analysis using Affymetrix genechip Human Gene 1.0

ST. The up-regulated and down-regulated genes upon mimic-152 transfection are selected using a ±1.25-fold cut off Statistical Analysis All data are expressed as mean+S.E.M. Statistical comparisons were performed using Student's t-Test or Mann-Whitney U test. Statistical significance was set at a value of $p<0.05$.

Figures 8A, 8B, 8C, 8D:
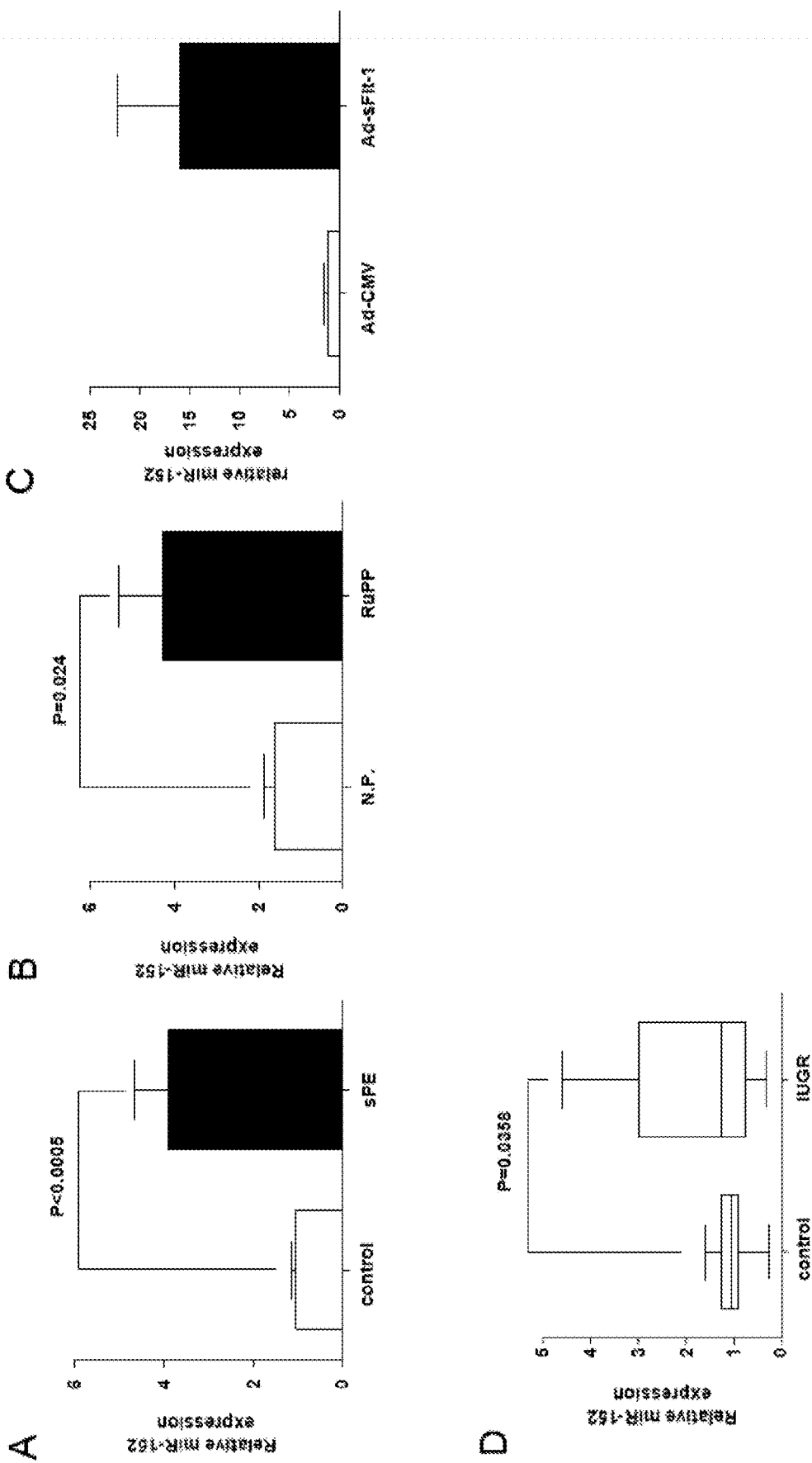

Results:

Placental miR-152 Expression is Increased in Preeclampsia Patient and Animal Models, IUGR, Obesity Pregnant Women and Diabetic Mouse Model Although Zhu and colleagues demonstrated the elevated expression of miR-152 in preeclampsia (Zhu et al., 2009), the placental samples used in their study were collected from preeclampsia women with an average gestational age of 35.9 weeks. To investigate the miR-152 expression in more precisely defined severe preeclampsia patient, the placental samples from preeclampsia women with an average gestational age of 29.7 weeks were collected and examined for miR-152 expression by quantitative PCR. Quantitative PCR revealed that miR-152 in the preeclamptic placenta (N=14) was significantly increased compared to gestation age matched control normotensive placenta (N=17), but not changed in IUGR placenta (N=11), implying miR-152 is up-regulated specifically in preeclampsia (FIG. 8A).

To further confirm the up-regulation of miR-152 in preeclampsia, the expression of miR-152 was examined in two animal models of preeclampsia. The pregnant mice receiving ad-sFlt-1 adenovirus injection exhibited significant increased placental miR-152 level (FIG. 8C) as well as elevated sFlt-1 expression and mean artery pressure compared to ad-CMV control virus injected mice (FIG. 16). Moreover, the miR-152 expression in placenta of pregnant Sprague Dawley rats that undergone reduced uterine perfusion pressure surgery (N=17) was also significantly increased compared to normal pregnant rat (N=12, FIG. 8B), suggesting that miR-152 elevation is associated with pathogenesis of preeclampsia. Severe preeclampsia patients are normally associated with fetal growth restriction (IUGR), thus we examined the miR-152 level in IUGR patient placentas. The expression of miR-152 in the IUGR patients (N=11) was increased by 88% compared to the gestational age-matched controls (N=17, FIG. 8D).

Figures 8E, 8F, 8G, 8H:
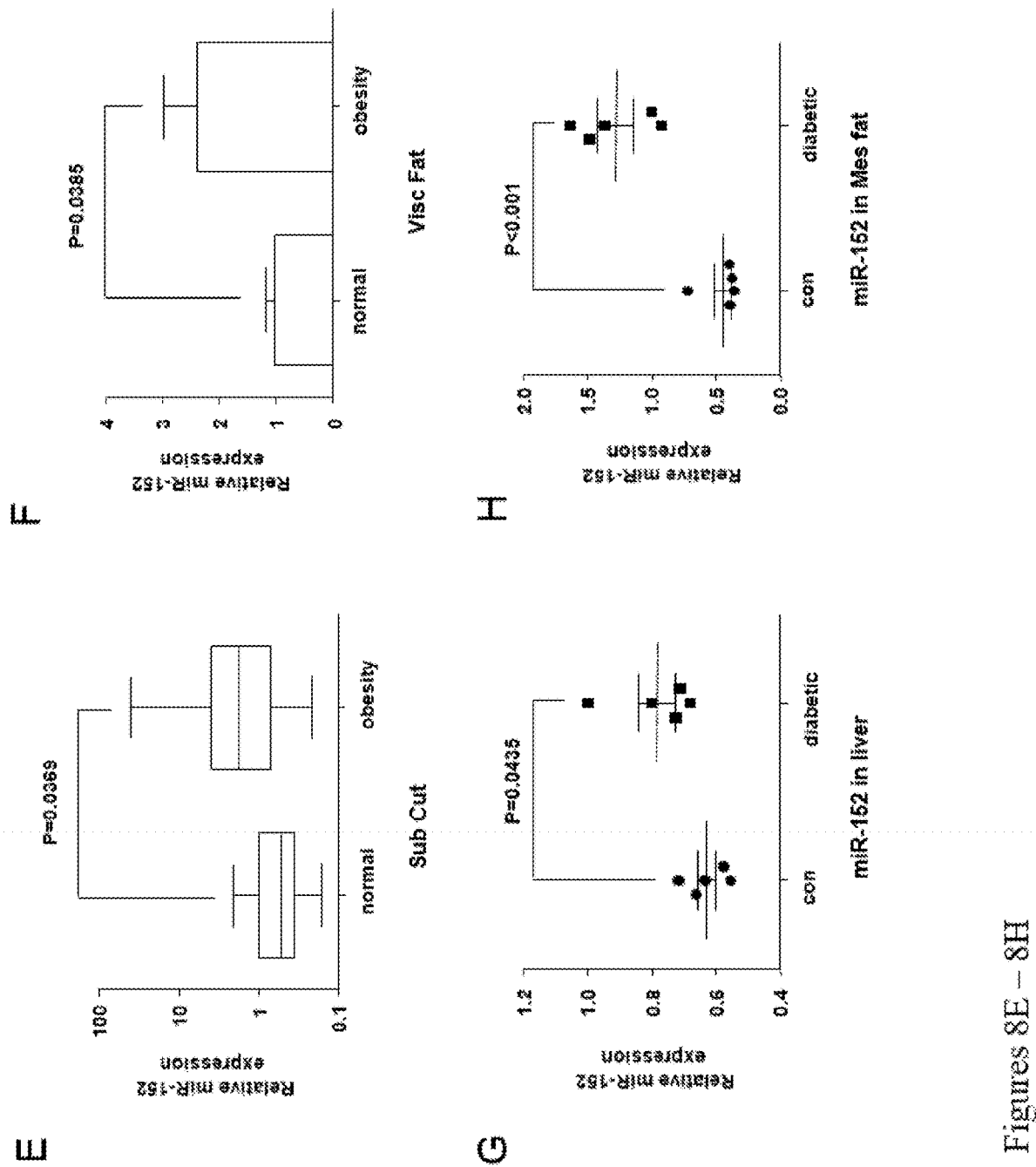

Since obesity pregnant women pose a high risk to preeclampsia, we examined the miR-152 expression in the adipose tissues of obesity pregnant women. As expected, miR-152 expression in the visceral (N=25) and subcutaneous fat (N=24) of obesity pregnant women was increased significantly compared to lean pregnant women (N=20-22) (FIGS. 8E and F). Moreover, we tested the miR-152 level in liver and mesenteric fat of the diabetic db/db mouse. The results confirmed the significant elevation of miR-152 expression in db/db mice compared to controls (N=5, FIGS. 8G and H).

Hypoxia, Inflammation and Growth Factors Elevated MiR-152 Expression

Figures 9A, 9B, 9C, 9D, 9E, 9F, 9G, 9H, 9I:
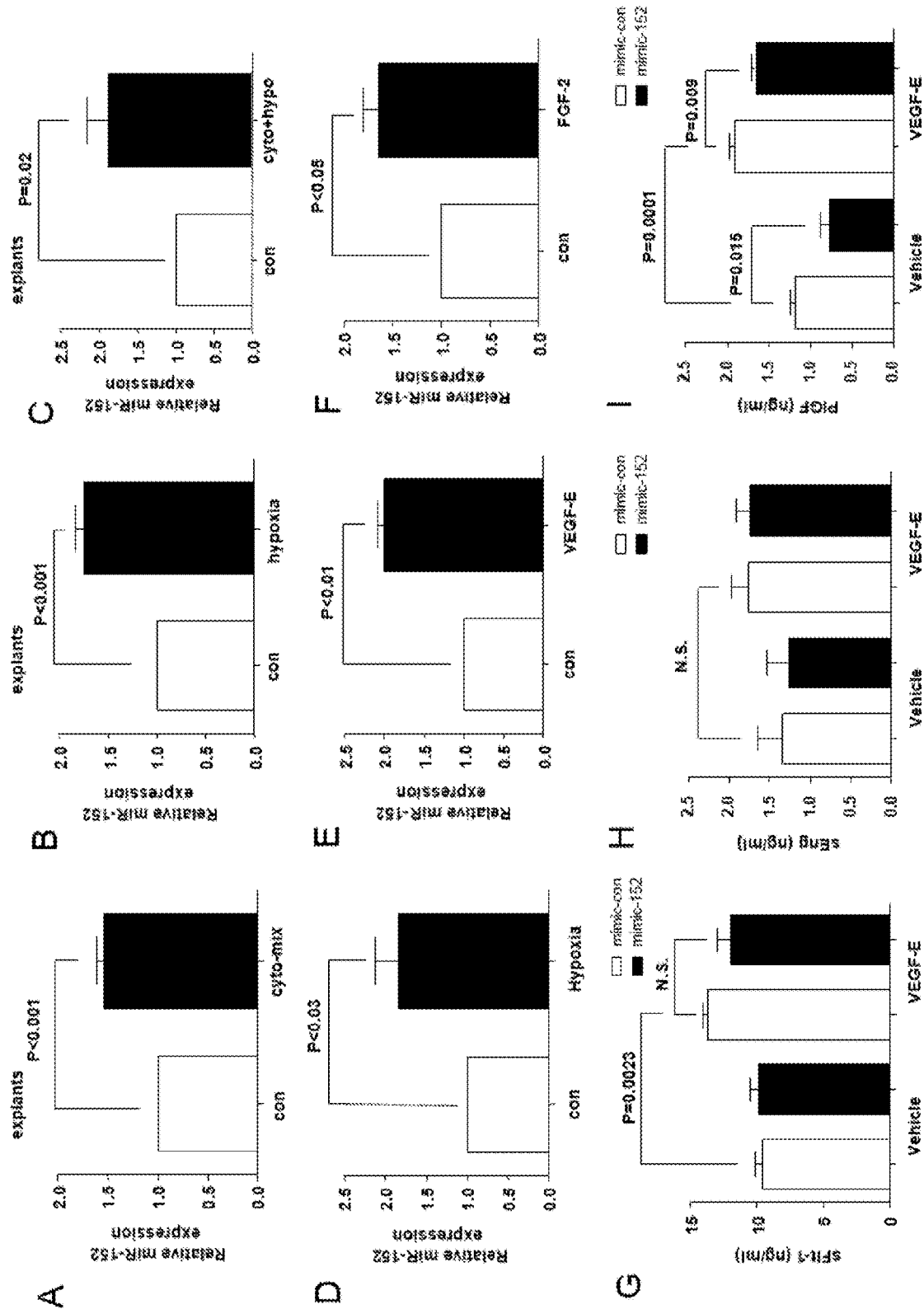

Preeclamptic placenta is associated with hypoxia, inflammation condition as well as the elevation of VEGF and FGF-2 growth factors (Hunter et al., 2000; Ozkan et al., 2008), thus the miR-152 expression in the placental explants and endothelial cells under hypoxia, inflammation and VEGF stimulation was determined by qPCR. Stimulation of mixed inflammatory cytokines in placental explants increased miR-152 by approximate 55% (FIG. 9A). Furthermore, hypoxia treatment increased miR-152 expression by 75% and 84% in placental explants (FIG. 9B) and endothelial cells (FIG. 9D) respectively. The combination of hypoxia and inflammatory cytokine mixture stimulation increased miR-152 expression by 87% in placental explants (FIG. 9C). Moreover, VEGF and FGF-2 stimulation elevated miR-152 expression by approximately 100% and 65% respectively (FIGS. 9E and F). These data confirmed that miR-152 is regulated by the pathological conditions in preeclamptic placenta.

MiR-152 Modulates PlGF Expression in Endothelial Cells

The release of anti-angiogenic factors, sFlt-1 and sEng, and the inhibition of placental growth factor expression are the main cause of preeclampsia (Powe et al., 2011; Ahmad and Ahmed, 2004). Moreover, VEGF and inflammatory cytokines stimulation increases sFlt-1 and sEng release (Cudmore et al., 2008), therefore we examined whether miR-152 modulates sFlt-1, sEng or PlGF expression in endothelial cells. HUVECs were transfected with mimic-152 to over-express miR-152 (FIG. 17) and the sFlt-1, sEng and PlGF levels were examined by ELISA. Overexpression of miR-152 in HUVECs decreased PlGF expression under both vehicle and VEGF-E stimulation (FIG. 9I). Although the expression of sFlt-1 (FIG. 9G) and sEng (FIG. 9H) was unaltered, the PlGF level was significantly reduced, thus the ratio of sFlt-1/PlGF was increased. These data further support the concept that miR-152 upregulation may contribute to the pathogenesis of preeclampsia.

MiR-152 has No Effect on Cell Proliferation

Figures 10A, 10B, 10C:
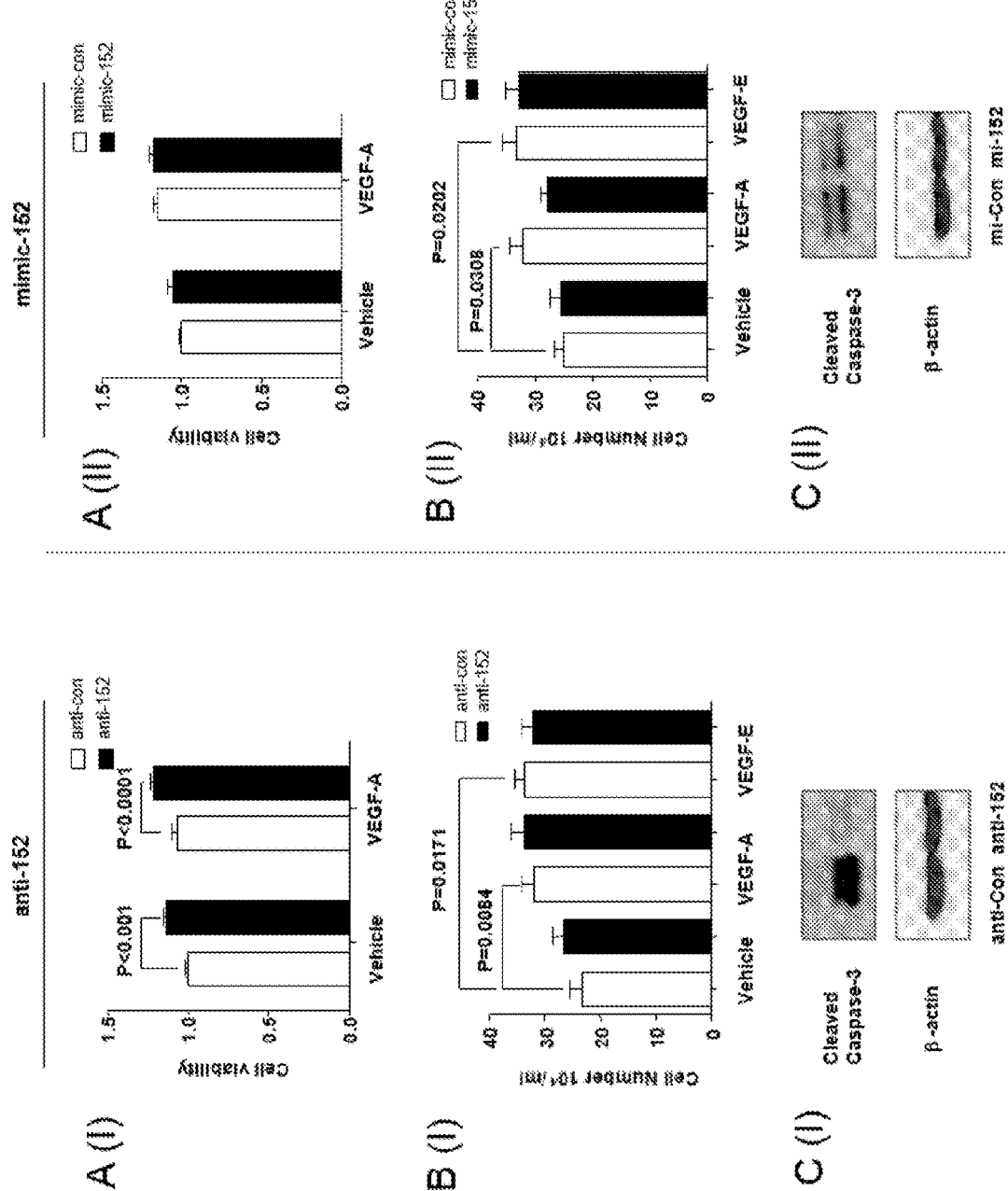

Since endothelium dysfunction is the main cause of preeclampsia, we tested whether miR-152 modulates endothelial cell functions. HUVEC cells were transfected with either synthetic inhibitor (anti-152) (I) or the mimic of miR-152 (mimic-152) (II) and the MTT (FIG. 10A) or cell proliferation assay (FIG. 10B) was performed. Although anti-152 significantly increased cell viability in HUVECs, the mimic-15 did not change the cell viability under vehicle or VEGF-A stimulation (FIG. 10A). Moreover, cell proliferation assay confirmed that either anti- or mimic-152 had no effect on HUEVC cell proliferation (FIG. 10B). Furthermore, western blot analysis revealed that the expression of cleaved Caspase-3 in HUVECs transfected with anti- or mimic-152 was not changed (FIG. 10C).

Figures 11A, 11B, 11C:
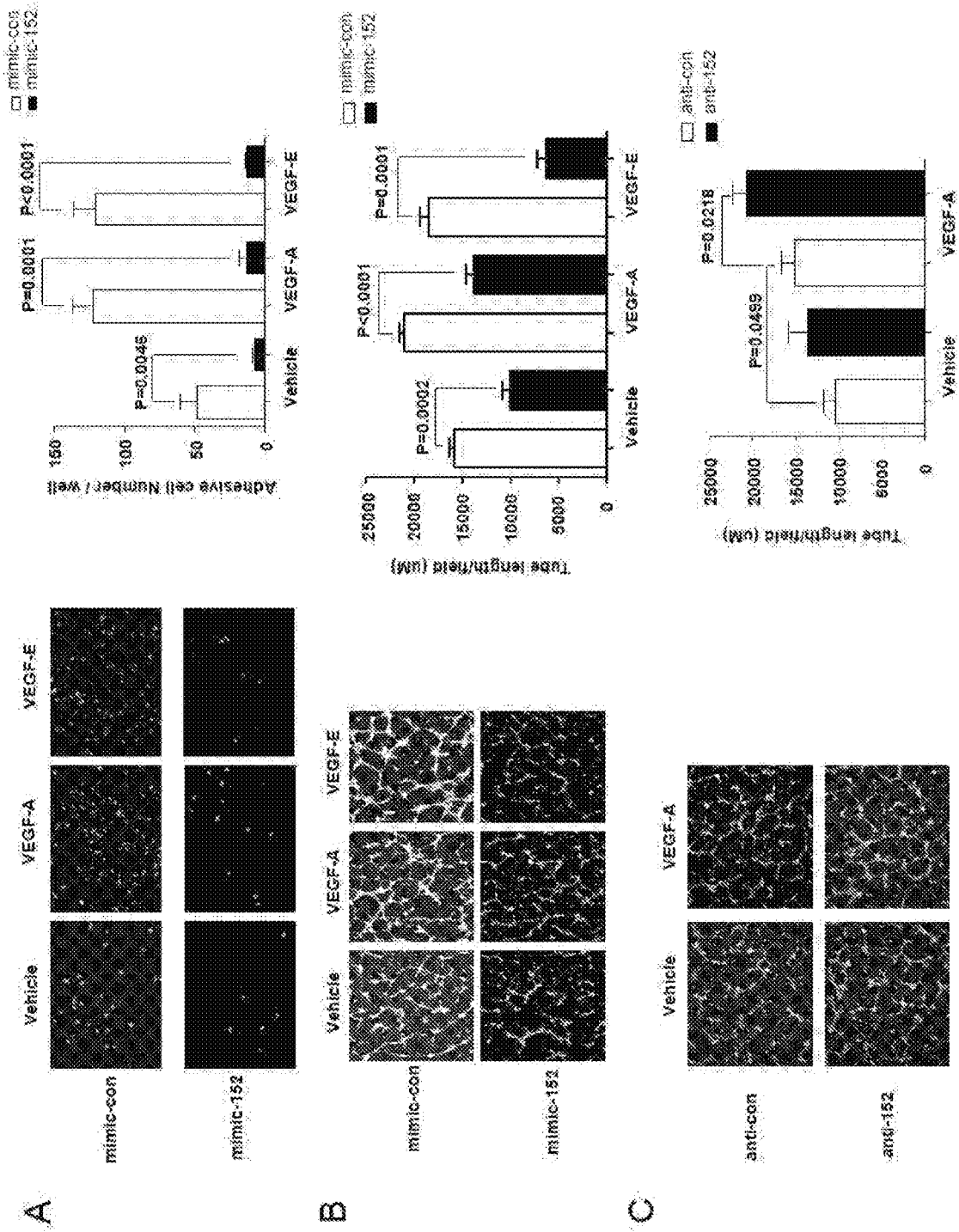

MiR-152 Inhibits Endothelial Cell Adhesion and In Vitro Endothelial Cell Tube Formation, but Promotes Cell Migration The effects of miR-152 in endothelial cell adhesion, migration and angiogenesis were further tested. HUVEC cell adhesive ability was dramatically decreased in the mimic-152 transfected cells regardless the stimulation of VEGF-A and VEGF-E. Cell counting confirmed an 84% reduction of the numbers of adhesive cells in the mimic-152 transfected HUVECs under vehicle condition, while approximate 89% reduction under VEGF-A and VEGF-E stimulation compared to mimic-con transfected HUVECs (FIG. 11A).

Since miR-152 inhibits angiogenesis in tumor cells, we speculated that miR-152 also inhibits angiogenesis in placental endothelial cells to contribute to the pathogenesis of preeclampsia. HUVEC cells transfected with mimic-152 exhibited decreased tube formation on Matrigel under vehicle, VEGF-A or VEGF-E stimulation (FIG. 11B). Quantitative analysis revealed a 37% reduction in the tube formation of mimic-152 transfected cells under vehicle condition and 34% to 66% reduction under VEGF-A and VEGF-E stimulation. Conversely, anti-152 transfection increased tube formation in the HUVEC cells by approximate 33% under VEGF-A stimulation (FIG. 11C). These data confirmed that miR-152 negatively modulates placental endothelial cell in vitro angiogenic ability.

Furthermore, the scratch assay revealed that overexpression of miR-152 increased (FIG. 18A) while inhibition of miR-152 significantly decreased (FIG. 18B) HUVEC cell migration ability under vehicle or growth factor stimulation.

Figures 12A, 12B, 12C, 12D, 12E, 12F:
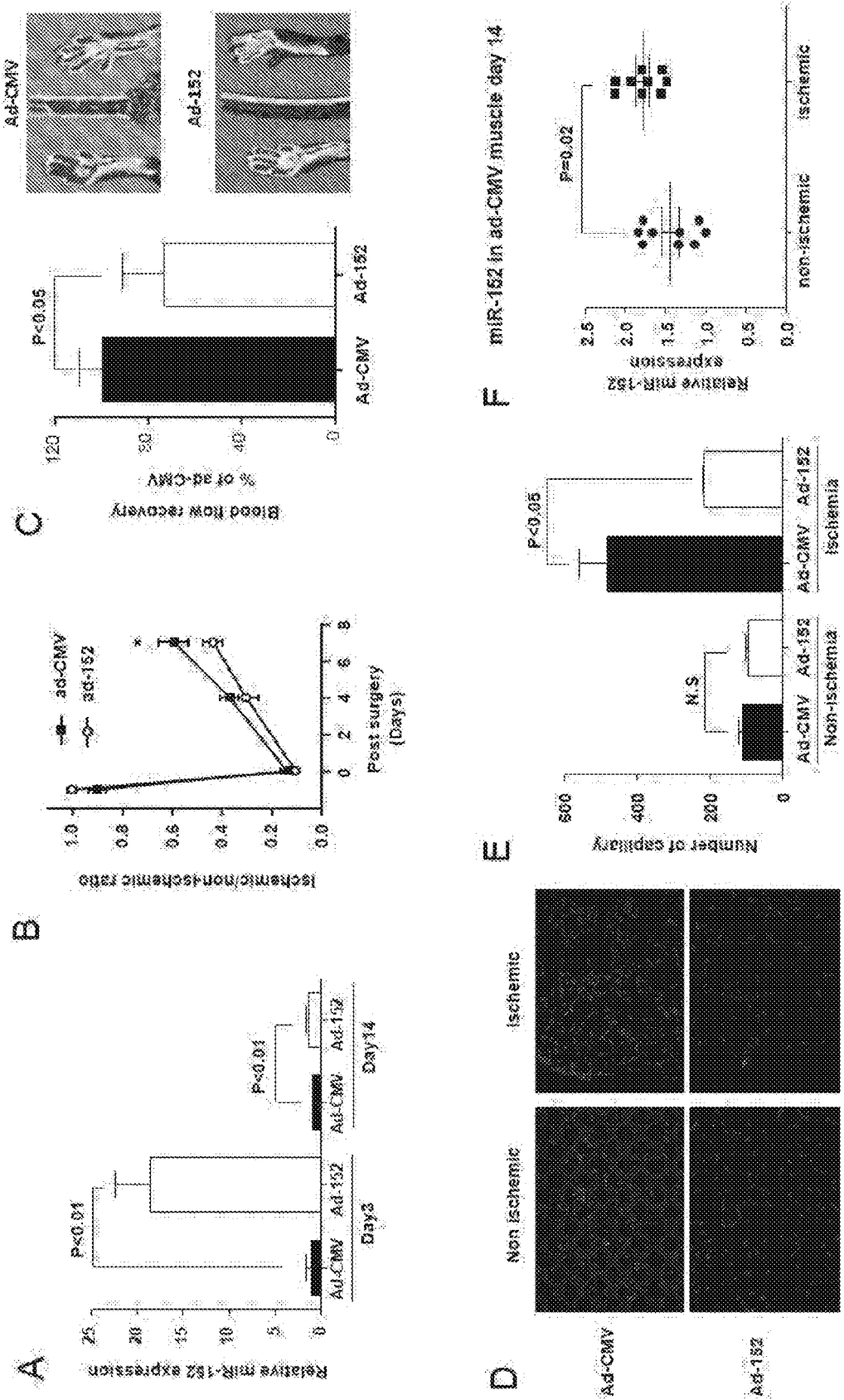
Figures 13A, 13B, 13C, 13D:
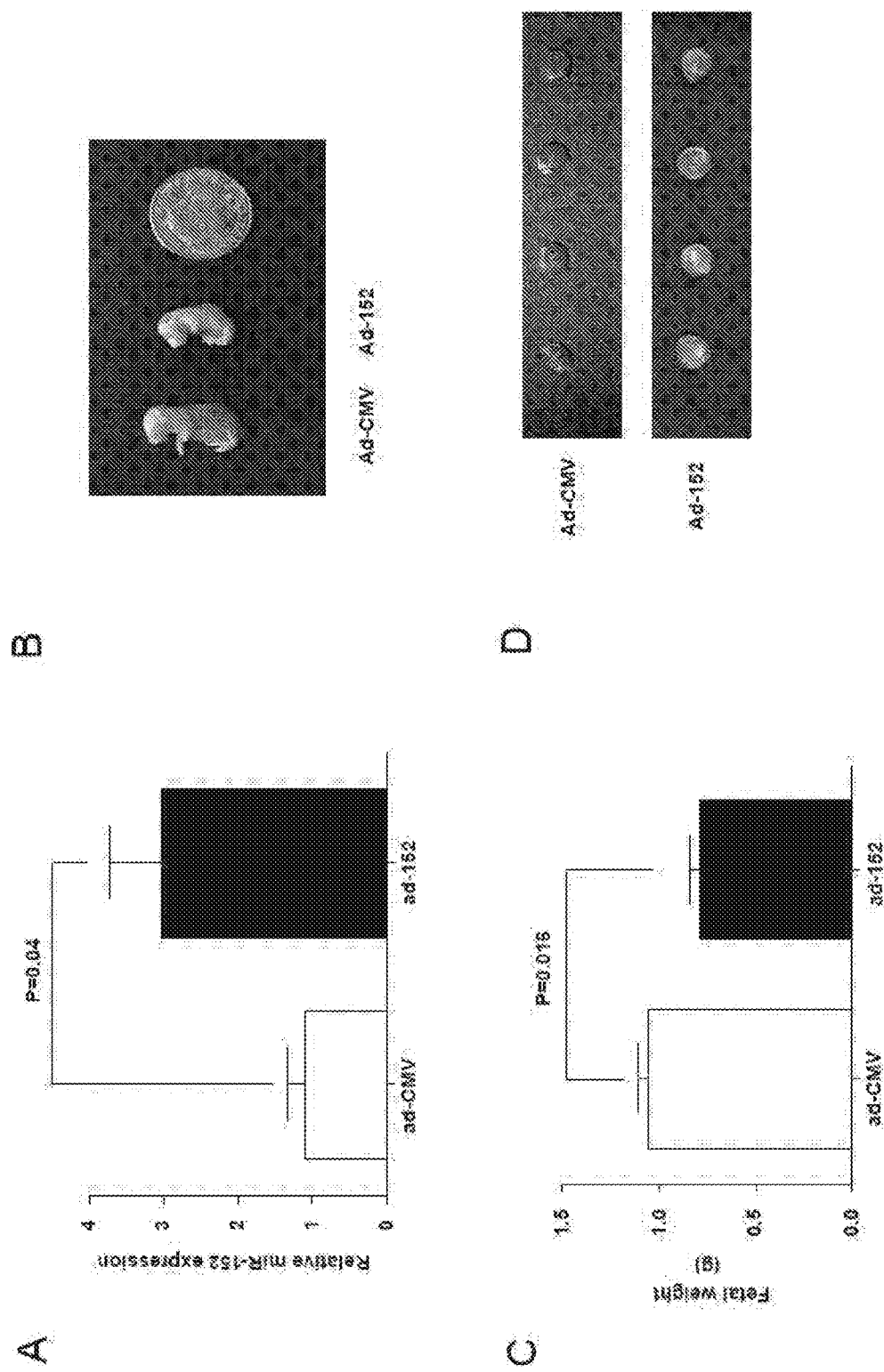

Overexpression of miR-152 Impaired Blood Recovery and Revascularization in Hind Limb Ischemia Model To further test the anti-angiogenic property of miR-152 in vivo, mouse hind limb ischemia model was utilized. Adenovirus overexpressing miR-152 was injected into the femoral artery which was later been removed. The expression of miR-152 in the Gastrocnemius muscle was increased approximate 18-fold on day 3 and 55% on day 14 compared to non-ischemic muscle (FIG. 12A). Hind limb ischemic blood flow recovery was compared in ad-152 injected mice to ad-CMV injected controls. Blood flow was assessed serially after HLI surgery (days 0, 3, 7, and 14) by LASER Doppler in the plantar aspect of the paws (FIG. 12C). The blood flow recovery was evidenced in ad-CMV injected mice on day 3 and the ad-152 injected mice exhibited consistent lower blood flow at day 3 and day 7 (FIG. 12B). At day 7, the blood flow in ad-152 injected mice showed a maximum reduction of approximate 30% compared to controls (FIG. 12C). Since blood flow recovery relates to the increased tissue capillary density, we examined the capillary density in gastrocnemius muscle (FIG. 13D). As expected, capillary density was increased in the ischemic gastrocnemius muscle of both ad-152 and ad-CMV injected mice; however in the ischemic ad-152 injected muscle, there was a marked reduction of the capillary increase (FIG. 12E). Moreover, in agreement with the in vitro observation, the expression of miR-152 in the ischemic muscle of control mice was significantly increased compared to control non-ischemic muscle (FIG. 12F).

Overexpression of miR-152 Impaired Placental Vasculature in Pregnant Mouse and Inhibited Fetal Growth To investigate the effect of miR-152 overexpression in pregnancy, the adenovirus overexpressing miR-152 was injected intraperitoneally into pregnant mice at E11.5. After six days of injection, the blood from ad-CMV and ad-152 injected mice was taken and the expression of miR-152 was measured by qPCR. The ad-152 injection significantly increased miR-152 expression compared to ad-CMV control (FIG. 13A). In line with these data, the fetal growth in the ad-152 injected pregnant mice was significantly restricted (FIG. 13B). This observation was further confirmed by the measurement of average fetal weight in these mice. The foetuses from ad-152 injected mice exhibited around 25% reduction in body weight compared to the ad-CMV injected mice (FIG. 13C).

Figure 13E:
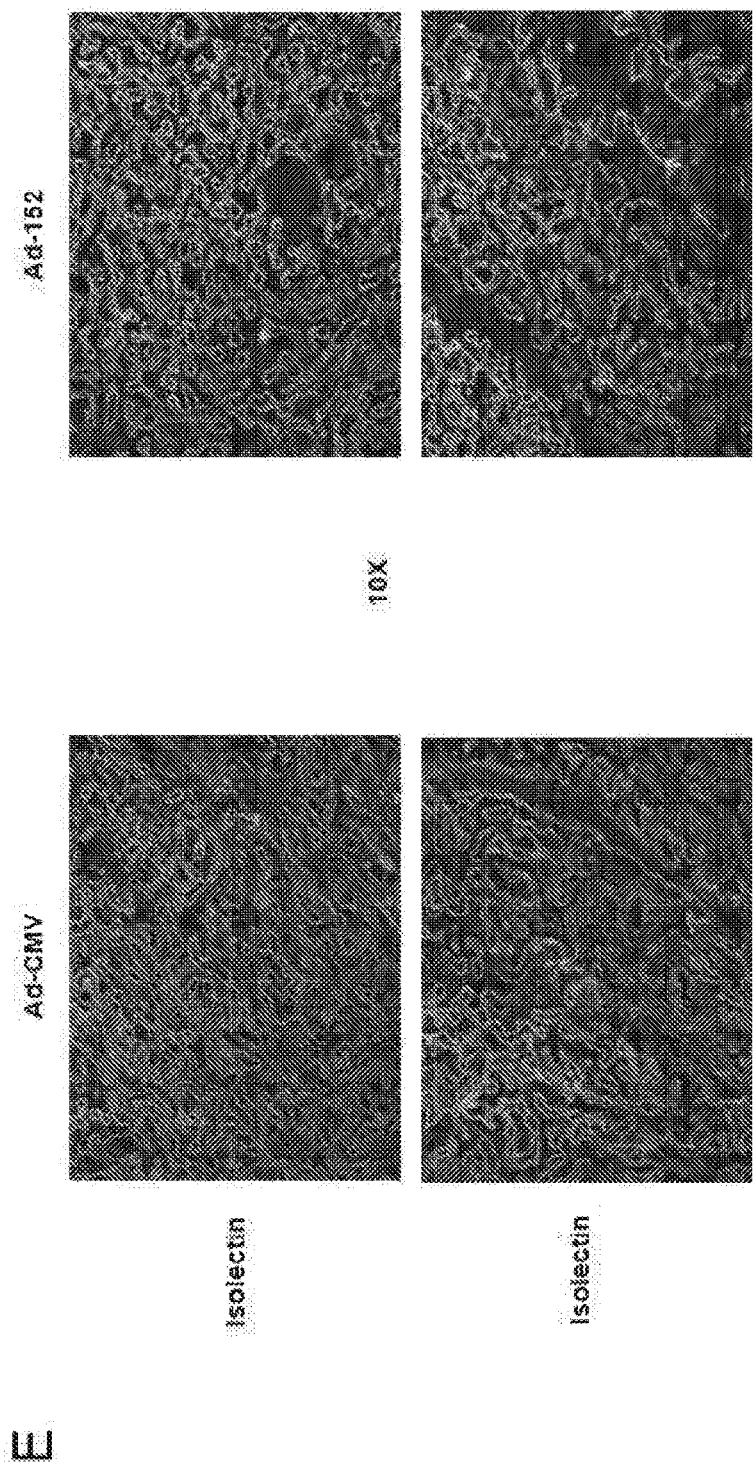

More importantly, the fetal growth restriction could be caused by the impaired neovasculature in the placenta as evidenced by the avasculated placenta in the ad-152 injected mice (FIG. 13D). Histological analysis of placental labyrinth zones further confirmed this observation. The labyrinth zone consists of cells of trophoblast and fetal endothelial cells, forming a large surface area for nutrient and gas exchange between the mother and foetus. Using isolectin B4 to highlight the fetal endothelial cells, the anatomical features of labyrinth zone in ad-152 and ad-CMV injected mice were analyzed. The vasculature in the labyrinth zone of control mice was well organized with high density of fetal vascular branching. However, the vascular structure in the ad-152 injected labyrinth was observed as irregular branching with much lower density (FIG. 13E).

MiR-152 Directly Targets ITGA5 in Endothelial Cells

Figures 14A, 14B, 14C, 14D:
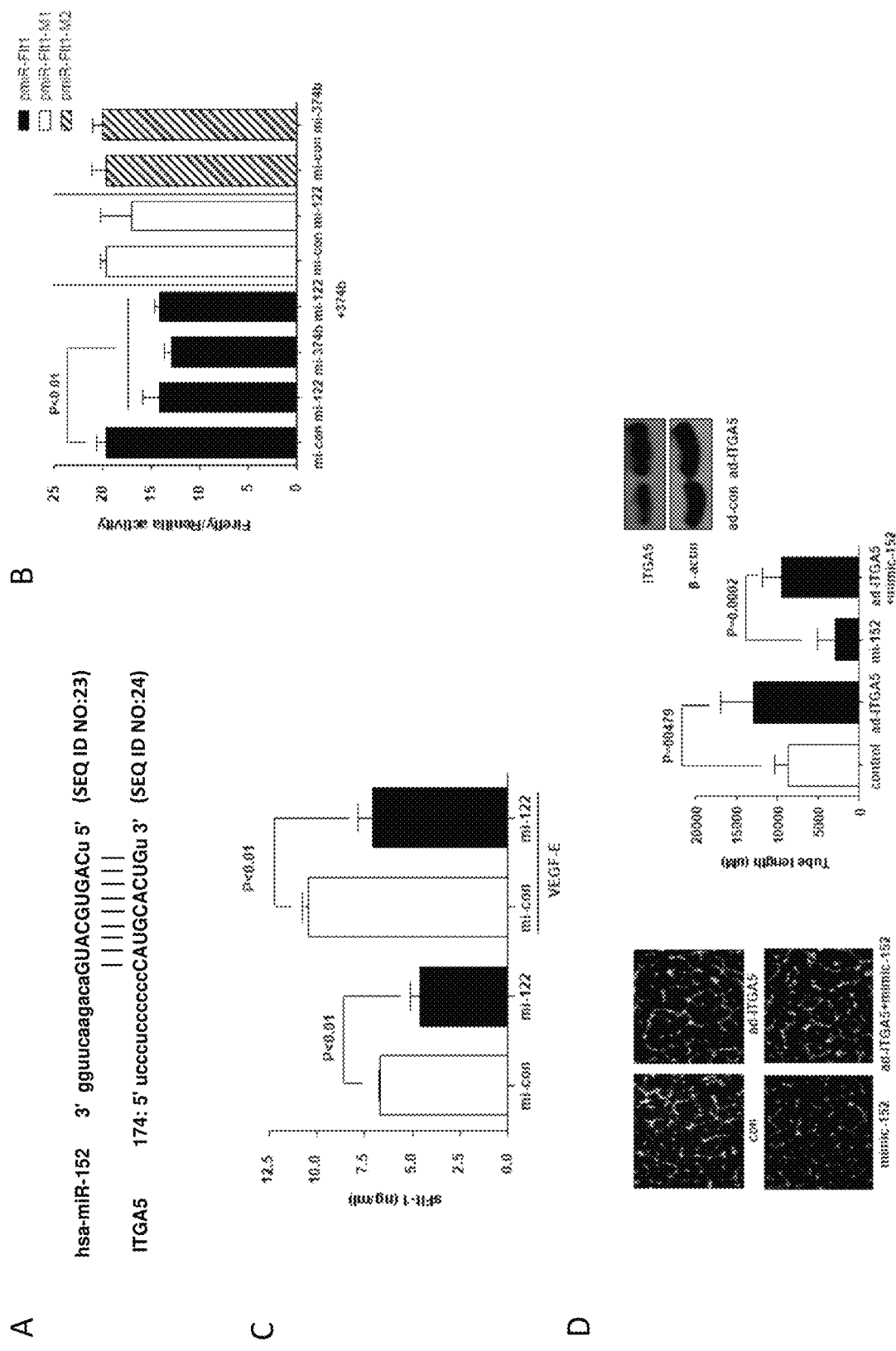

To identify the direct targets of miR-152, gene expression microarray was performed using RNA samples from mimic-152 and mimic-con transfected HUVEC cells. The 14 up-regulated and 34 down-regulated genes upon miR-152 overexpression were selected with ±1.25-fold cut off. These expression altered genes have broad functions on vascular remodelling, cell adhesion, angiogenesis, cell mobility and survival. Moreover, the down-regulated genes were further analyzed using online prediction tools, microRNA.org, PicTar and Target Scan, to confirm the possible direct targets of miR-152 by sequence alignment. Finally, 18 out of 34 down-regulated genes were selected for candidates of miR-152 direct target and the expression of some of these candidate targets were further tested by western blot in HUVEC cells (FIG. 14B).

Among the targets tested, ITGA5 was the one most regulated by miR-152. ITGA 5 was predicted to be miR-152 direct target by the online prediction tools (FIG. 14A) and also confirmed by western blot that miR-152 overexpression decreased while inhibition of miR-152 increased ITGA5 expression in HUVECs (FIG. 14B). MicroRNA target assay further proved that transfection of mimic-152 significantly inhibited luciferase activity in the pmiR-ITGA5 transfected HEK293 cells, but not in the mutant pmiR-ITGA5M transfected cells (FIG. 14C; FIG. 19). To validate that miR-152 target ITGA5 to fulfil its role on endothelial dysfunction, we tested whether overexpression of ITGA5 could rescue the mimic-152 mediated inhibition of angiogenesis. As expected, overexpression of ITGA5 increased spontaneously tube formation and significantly recovered mimic-152 inhibited tube-like structure in HUVEC cells (FIG. 14D).

Figures 15A, 15B, 15C, 15D, 15E:
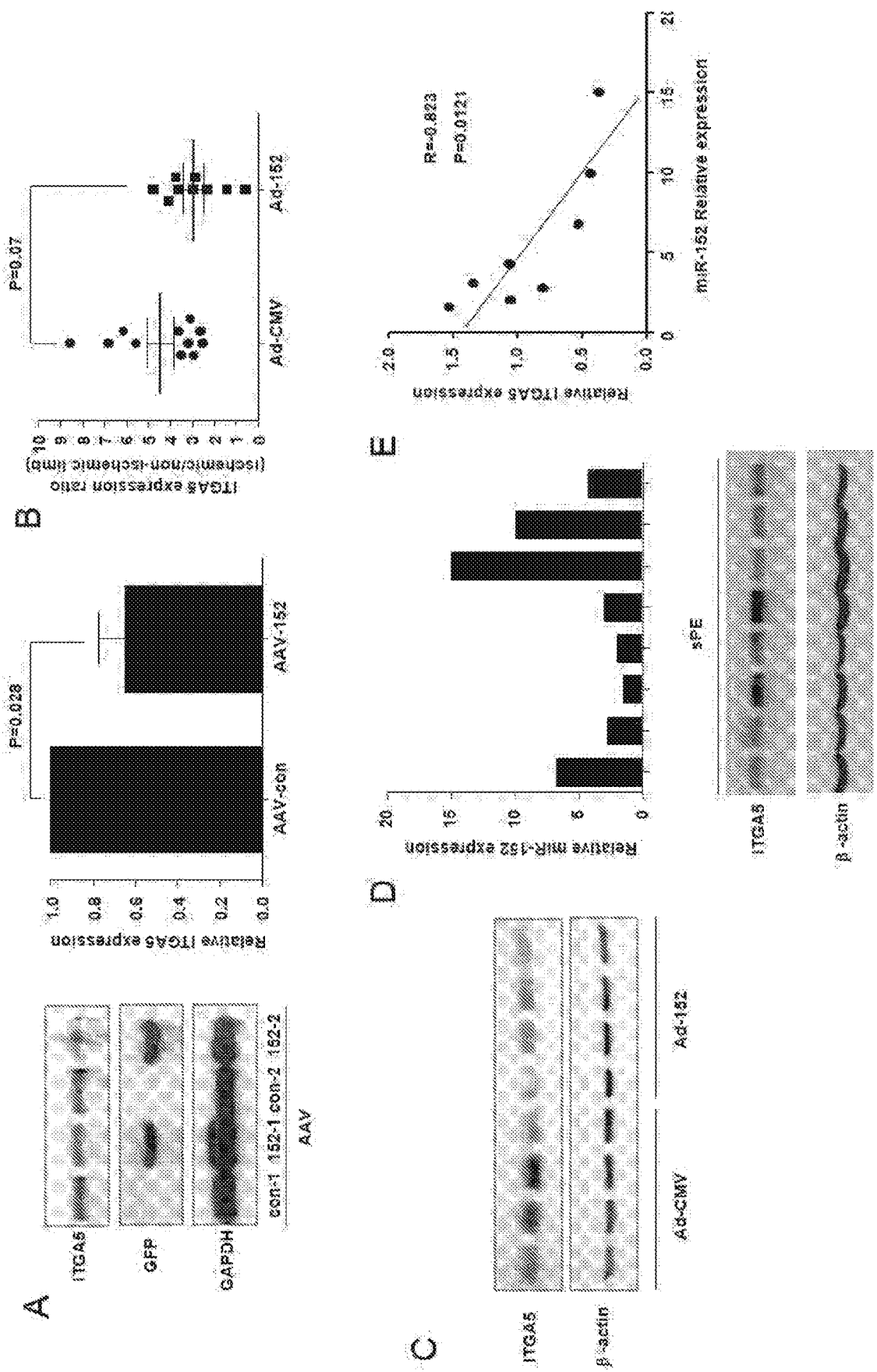

MiR-152 Targets ITGA5 In Vivo and Correlates with ITGA5 in Severe Preeclampsia Patients More importantly, the regulation of ITGA5 by miR-152 was also confirmed in animal models used in this study. AAV-152 virus injection mediated overexpression of miR-152 (FIG. 20) in the muscle of mouse limb significantly decreased ITGA5 expression compared to control AAV virus injected limb muscle (FIG. 15A). Furthermore, in hind limb ischemia condition, the ITGA5 expression in the ischemic muscle of mice injected with ad-152 was decreased compared to ad-CMV injected ischemic muscle (FIG. 15B). Moreover, the ITGA5 expression in the placenta of ad-152 injected pregnant mice decreased dramatically compared to ad-CMV injected placenta (FIG. 15C).

Since miR-152 is up-regulated in preeclampsia patients and ITGA5 is identified to be the direct target of miR-152, we speculate that the expression of miR-152 and ITGA5 in the preeclampsia patients was negatively correlated. The expression of miR-152 and ITGA5 was examined from 8 preeclampsia and 8 gestational age matched control patients using qPCR and western blot respectively (FIG. 16D). The negative correlation of miR-152 and ITGA5 expression was found in the preeclamptic placentas (R=−0.823, FIG. 16E), but not in the control normotensive placentas, suggesting miR-152 targets ITGA5 specifically in the pathological condition of preeclampsia.

Discussion

MiR-152 in Preeclampsia

Although microarray profiling and next generation sequencing techniques revealed that microRNAs are differently expressed in the placenta of preeclamptic women (Yang et al., 2011; Wu et al., 2012; Hromadnikova et al., 2012; Pan et al., 2012), only very limited number of microRNAs have been characterized for their roles in preeclampsia pathogenesis, especially in the dysfunction of endothelium. Mir-152 expression has been shown to be up-regulated in the placenta of preeclampsia patients by microarray profiling (Zhu et al., 2009). In line with this, our data confirmed the elevated expression of miR-152 in a more precisely defined population of severe preeclampsia patients with an average gestational age of 29.7 weeks. Moreover, we proved the up-regulated miR-152 expression in the mouse and rat models of preeclampsia, further strengthened the possibility that miR-152 is associated with preeclamptic pathogenesis.

The preeclamptic placenta is associated with hypoxia and inflammatory conditions (Lockwood et al., 2008; Soleymanlou et al., 2005). Our data demonstrated that hypoxia and inflammatory cytokines increased miR-152 expression in placental explants suggesting miR-152 could be the molecular clue to understand the pathogenesis of preeclampsia. In addition, the imbalance of angiogenesis has been highlighted as the primary culprit in preeclampsia (Ramma and Ahmed, 2011; Ramma et al., 2012). In our study, miR-152 was identified to be a negative regulator of PlGF, an important growth factor for placental function, in endothelial cells. Although sFlt-1 and sEng levels were not changed by overexpression of miR-152, the sFlt-1/PlGF ratio was increased due to the decreased level of PlGF. Since the elevated sFlt-1/PlGF ratio is an important indicator of angiogenic imbalance and a reliable biomarker in the assessment of preeclampsia (De Vivo et al., 2008; Verlohren et al., 2012), the elevated miR-152 expression in the preeclamptic placenta may contribute to the angiogenic dysfunction in preeclampsia pathogenesis.

MiR-152 Modulates Endothelial Functions Via ITGA5

Mir-152 has been shown to inhibit cell proliferation and adhesion (Zhou et al., 2012; Mancini et al., 2012) as well as tumor cell angiogenesis (Zheng et al., 2013; Xu et al., 2013), but not in the endothelial cells. Our data demonstrated that miR-152 decreased endothelial cell adhesive and angiogenic abilities, and increased cell migration, but had no effect on cell proliferation. Endothelial dysfunction plays a central role in the pathogenesis of preeclampsia and causes most clinical symptoms of preeclampsia (Poston 2006; Baumwell and Karumanchi, 2007), thus miR-152 may contribute to the pathogenesis of preeclampsia by modulation of endothelial functions.

ITGA5 belongs to the integrin alpha chain family which promotes cell adhesion, invasion and migration in cancer cells (Hood and Cheresh, 2002; Wang et al., 2008; Qin et al., 2011). Moreover, it has been shown to promote vasculogenesis and angiogenesis in endothelial cells and mouse embryo (Francis et al., 2002; Bonauer et al., 2009). In our study, ITGA5 was found to be the direct target of miR-152 and also the mediator of miR-152 induced endothelial dysfunction. By directly targeting ITGA5, miR-152 inhibited endothelial cell adhesion and the reduced cell adhesion subsequently led to the promoted cell migration (Moh and Shen, 2009; Grzesiak et al., 2005). More importantly, overexpression of ITGA5 rescued the mimic-152 inhibited angiogenesis in endothelial cells suggesting that ITGA5 is the downstream effector of miR-152 mediated endothelial dysfunction at least on the disruption of angiogenesis. Notably, our microarray data revealed more possible targets of miR-152 which regulate vascular remodelling, cell adhesion, angiogenesis, cell mobility and survival processes. These potential targets of miR-152 may further contribute to the different clinical manifestation of preeclampsia.

MiR-152 for Preeclampsia Therapy

Since effective treatment to preeclampsia is not currently available, the early prediction of high-risk women is important for the prevention and primary care of this medical condition (Leslie et al., 2011). Moreover, a recent meta-analysis suggests that low-dose aspirin started before 16 weeks' gestation could prevent up to 50% of PE, severe PE, and intrauterine growth restriction (IUGR) in high-risk women (Bujold et al., 2009). Thus a biomarker that accurately predicts preeclampsia is of great clinical value. Recently, miR-152 has been implicated in the serum of pregnant women and suggested for the potential use as biomarker (Williams et al., 2013). Based on our current study that miR-152 elevated in severe preeclampsia, miR-152 expression in the serum of early pregnancy of preeclampsia high-risk women should be examined to validate its biomarker potential.

Preeclampsia is a multifactorial disease which causes maternal and fetal morbidity and mortality worldwide (Pennington et al., 2012), thus there is a pressing need for novel approaches to tackle this complex medical condition. Our data revealed that miR-152 is elevated in the preeclampsia and subsequently leads to the endothelial dysfunction via targeting ITGA5 suggesting that miR-152 and ITGA5 may serve as potential therapeutic targets in preeclampsia. More importantly, the miR-152 and ITGA5 expression in the placenta of preeclamptic women was negatively correlated, further confirming the therapeutic potential of miR-152 and ITGA5 in preeclampsia.

miR-195

Methods and Materials:

Reagents and Antibodies

Recombinant growth factors, vascular endothelial growth factor A (VEGF-A), VEGF-E, tumor necrosis factor alpha (TNF-α), interferon gamma (IFN-γ) and interleukin 1 beta (IL-1β) were purchased from RELIATech (Brauschweig, Germany). Rabbit antibody against total eNOS and phosphor-eNOS were obtained from Cell Signaling Technology (Danvers, Mass. 01923, United States). Mouse anti-β-Actin antibody was obtained from Sigma-Aldrich (A5441, St. Louis, Mo., United States). Quantitative PCR primer against miR-195, gScript™ microRNA cDNA and Synthesis PerfeCTa® SYBR® Green SuperMix Kit were purchased from Quanta Biosciences. Growth factor reduced Matrigel purchased from Becton Dickinson (Oxford, UK). M199 medium was purchased from Invitrogen (Paisley, UK). Calcein AM Fluorescent Dye was purchased from BD Bioscience (P.O. Box 999 Sparks, Md., USA 21152).

Human Placental Tissue Collection and Preparation

Institutional Ethics Committee approved the placental tissue collection and written informed consent was obtained. All women were followed prospectively from enrolment until delivery. Different gestational placenta tissues from pregnant women of 1st trimester (N=6), 2nd trimester (N=6) and 3rd trimester (N=4) was collected and measured for relative miR-195 expression by qPCR. Human adipose tissues were collected from pregnant women with BMI over 30 (N=25 and 24 respectively) or with normal BMI (18-25) (N=22 for visceral and 20 for subcutaneous fat) and miR-195 expression was determined by qPCR. Moreover, human placental tissues were collected from women with pregnancy complicated by preeclampsia (N=14) and Intrauterine growth restriction (IUGR, N=12), and from normotensive pregnant women (N=17). The placental tissues collected were further used for quantitative PCR. Preeclampsia was defined as blood pressure >140/90 mm Hg on at least two consecutive measurements and maternal proteinuria of at least 300 mg/24 h and IUGR was defined as a foetus with estimated weight below the 10th percentile for its gestational age and abdominal circumference below the 2.5th percentile.

Cell and Placental Explants Culture

Human umbilical vein endothelial cells (HUVECs) were isolated and cultured in M199 medium as described previously (Bussolati et al, 2001). Experiments were performed on third or fourth passage HUVEC. First trimester placental tissues (6-9 weeks gestational age) were retrieved from normal pregnancies that had undergone elective termination. Placental villus tissue explants were prepared as described previously (Ahmad and Ahmed, 2004). Briefly, human placental villus explants were incubated under stimulation of test substances or hypoxia condition and collected for quantitative PCR of miR-195. To create hypoxic condition, 70-80% confluent HUEVCs or placental explants were cultured in an incubator with 1% 02 and 5% $CO_2$ at 37° C. To mimic inflammatory condition, HUVECs or placental explants were stimulated in cyto-mix cocktail containing TNF-α (20 ng/ml), IFN-γ (20 ng/ml) and IL-10 (2 ng/ml).

miRNA Mimic and Inhibitor Against miR-195

Figures 26A, 26B:
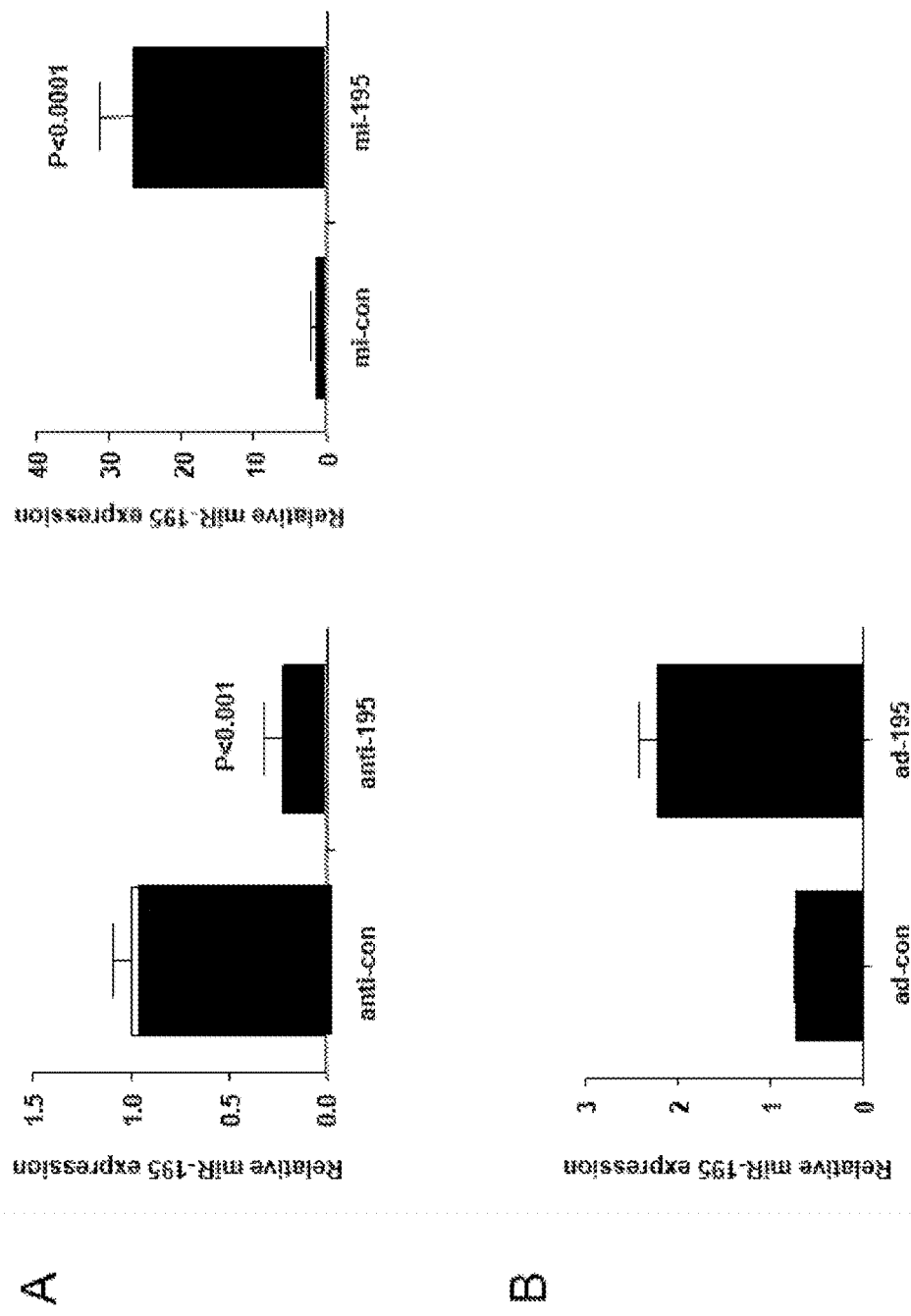

Chemically synthesized double-stranded microRNA mimic and single-stranded inhibitor against miR-195 (mi-195 and anti-195) were purchased from Qiagen. The efficiency of these molecules was tested by qPCR using primer against miR-195 (FIG. 26A). HUVECs were trypsinized, and $1 \times 10^6$ cells were electroporated with ≈0.6 ug mi-195, ≈3 ug anti-195 or equivalent control molecules using electroporation (Amaxa GmbH, Cologne, Germany) as described previously (Cudmore et al., 2007).

Adenovirus for miR-195

Adenovirus overexpressing eNOS constitutively activated form $eNOS^{S1177D}$, $ad-eNOS^{S1177D}$, was a gift from Prof Ingrid Fleming (Johann Wolfgang Goethe University, Germany). The adenovirus overexpressing miR-195, ad-195, were purchased from Vector Biolabs (Philadelphia, Pa., USA) and the efficiency was tested using Qper (FIG. 26B).

Ad-sFlt-1 Induced Mouse Preeclamptic Model

Adenovirus, ad-sFlt-1, was a gift from Prof. Richard Mulligan (Harvard Medical School, Boston, USA). The pregnant C57BL/6 mice were injected with $10^9$ PFU adenovirus, ad-CMV or ad-sFlt-1, at E 9.5 via tail vein injection. The sFlt-1 expression level in the circulation was measured using ELISA against Flt-1 and the mean artery pressure (MAP) was evaluated in the carotid artery at E 17.5 (FIG. 25). Placenta tissue from ad-CMV control virus (N=7) and ad-sFlt-1 virus (N=5) injected mice was collected and assayed for miR-195 expression using qPCR.

Reduced Uterine Perfusion Pressure (RUPP) Rat Model of Preeclampsia

Placenta samples of RUPP preeclamptic model were a gift from Dr. Fergus McCarthy (Cork University Maternity Hospital, Wilton, Cork, Ireland). The experimental procedure and the characterization of rat undergone RUPP surgery were described previously (McCarthy et al., 2011).

Real-Time Polymerase Chain Reaction

Sample preparation and real-time quantitative PCR was performed as described previously (Cudmore et al., 2007). Reverse transcription kit and primers against miR-195 were purchased from Quanta BioSciences.

Enzyme-Linked Immunosorbent Assay

Enzyme-linked immunosorbent assay (ELISA) kit for human PlGF was obtained from R&D Systems and performed according to the manufacturer's specifications.

Western Blotting

Total protein from HUVECs or animal tissue was lysed in RIPA buffer and assayed as previously described (Ahmad and Ahmed, 2004).

In Vitro Cell Viability and Proliferation Assay

HUVEC cells were electroporated with anti-195 or mi-195. After overnight recovery, transfected cells were trypsinized and plated into 96-well plate with $1 \times 10^4$ per well under the vehicle or VEGF-A (20 ng/ml) treatment. After 48 h, these cells were proceeded to MTT assay using cell growth determination kit (Cat No. CDG1, Sigma-Aldrich). For cell proliferation assay, transfected cells were plated in 24-well plate with $4 \times 10^4$ per well and stimulated with VEGF-A (20 ng/ml) or VGEF-E (20 ng/ml). After 48 h treatment, cells were trypsinized and the cell number per well was counted under microscope using a hemocytometer.

In Vitro Cell Adhesion Assay

HUVECs were electroporated with mi-195 or control mi-con. After 48 h, $2 \times 10^4$ mi-195 or mi-con transfected cells were plated in the 2% gelatin coated 96-well plate and treated with VEGF-A (20 ng/ml) or VEGF-E (20 ng/ml) for 30 mins. Thereafter, cells were washed three times with PBS, stained with Calcein AM Fluorescent Dye and proceeded to fluorescent microscopy. The number of the adhesive cells per field under the 4× magnification was counted.

In Vitro Tube Formation Assay

Formation of capillary-like structures of HUVECs transfected with mi-195 or anti-195 or mi-195 co-infected with $ad-eNOS^{S1177D}$ was determined on growth factor reduced Matrigel as previously described (Bussolati et al, 2001).

In Vitro Cell Migration Assay

HUEVC cells were electroporated with anti-195 or mi-195. After overnight recovery, the scratch was made in the centre of the transfected confluent cells in a 12- or 6-well plate. The width of the scratches was measured immediately at 0 h and 16-24 h after the scratches were generated. The cell migration distance was calculated by subtracting the width of scratches at 0 h and 16-24 h.

NO Gas Release Assay

Total NO in conditioned media was assayed as nitrite, the stable breakdown product of NO, using a Sievers NO chemiluminescence analyzer (Analytix, Sunderland, UK) as described previously (Ahmad et al., 2006). Briefly, HUVECs were infected with ad-con or ad-195 with MOI=100 and the condition medium were collected for NO measurement.

microRNA Target Luciferase Assay

The Homo sapiens cDNA containing untranslated region (UTR) of eNOS was purchased from Origene (Rockville, Md. 20850, USA) and the UTR region was subcloned into pMirTarget to generate eNOS-UTR-Luciferase (firefly) expression plasmid, pmiR-eNOS. The successful transfection of pmiR-eNOS in endothelial cells was validated by the expression of red fluorescent protein (RFP) (FIG. 27). The plasmid harbouring eNOS UTR mutant form of miR-195 binding site was generated using site-directed mutagenesis kit (Stratagene) with PCR primers containing the mutant site and the resulted plasmid was designated as pmiR-eNOSM. The primers used for PCR amplification were mNOS3-F (CTCTCAGGAGTAGAGTACCTGTAAAGGA-GAATCTCTAAATCAAGT (SEQ ID NO:17)) and mNOS3-R (ACTTGATTTAGAGATTCTCCTTTACAGG-TACTCTACTCCTGAGAG (SEQ ID NO:18)).

For microRNA target assay, HEK293 cells were transfected with pmiR-eNOS or pmiR-eNOSM together with mi-con or mi-195. The plasmid containing renilla luciferase gene was also transfected as the internal control. After overnight incubation, the relative firefly luciferase activity was measured and normalized to the renilla activity according to the manufacture's protocol of Dual-Luciferase® Reporter Assay System (E1910, Promega).

microRNA Target Prediction

The direct targets of miR-195 were predicted using online programs, microRNA.org (http://www.microrna.org/microrna/home.do), PicTar (pictar.mdc-berlin.de/), Target Scan (targetscan.org/), RNAhybrid 2.2 and RNA22 microRNA target prediction.

MicroArray Profiling

HUVEC cells were transfected with mi-195 and the total RNA sample was collected for whole genome gene array analysis using Affymetrix genechip Human Gene 1.0 ST. The up-regulated and down-regulated genes upon mi-195 transfection are selected using a ±1.25-fold cut off.

Statistical Analysis

All data are expressed as mean+S.E.M. Statistical comparisons were performed using Student's t-Test or Mann-Whitney U test. Statistical significance was set at a value of $p<0.05$.

Figures 21A, 21B, 21C, 21D, 21E, 21F, 21G, 21H, 21I:
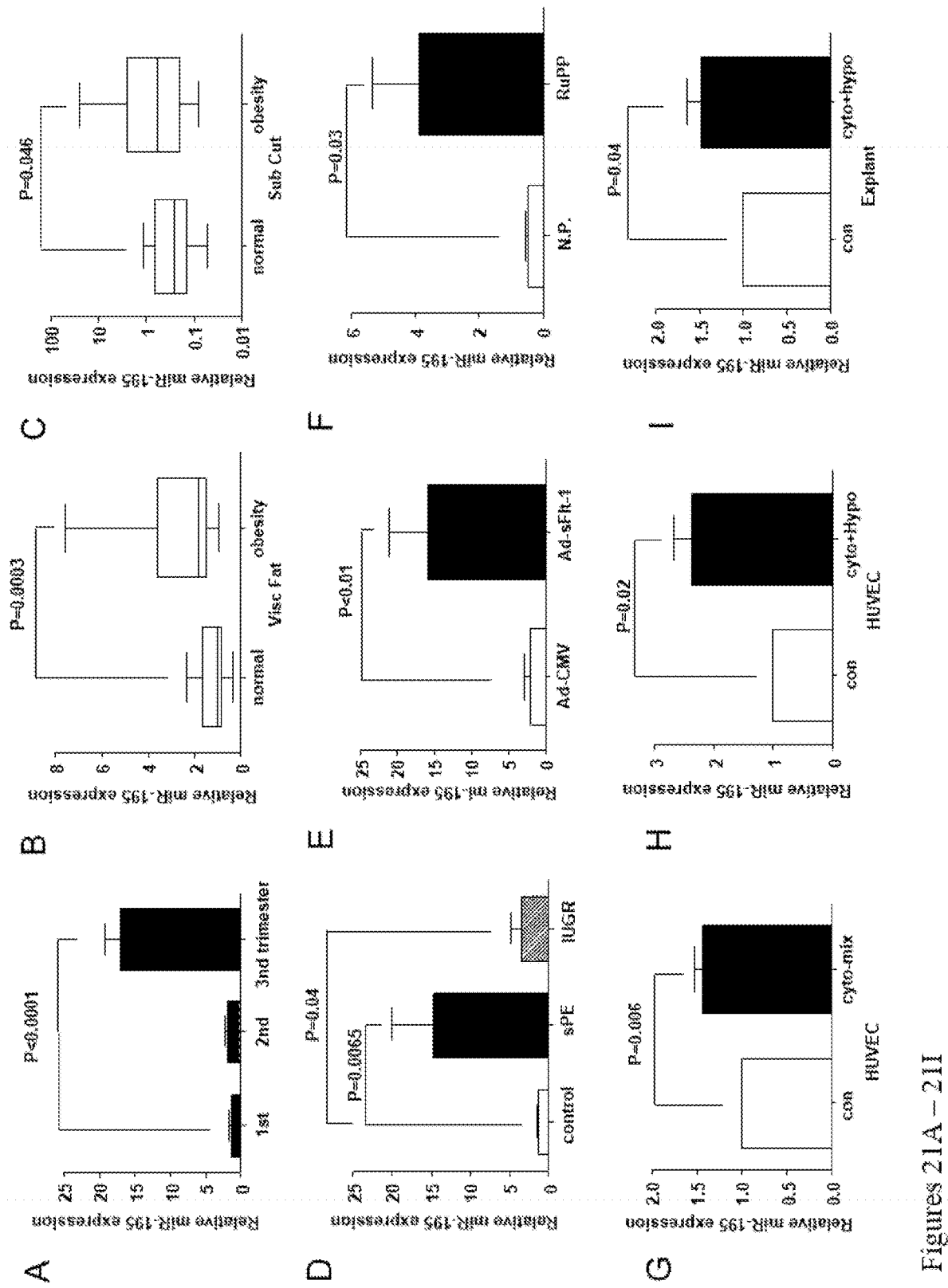
Figures 22A, 22B, 22C, 22D, 22E:
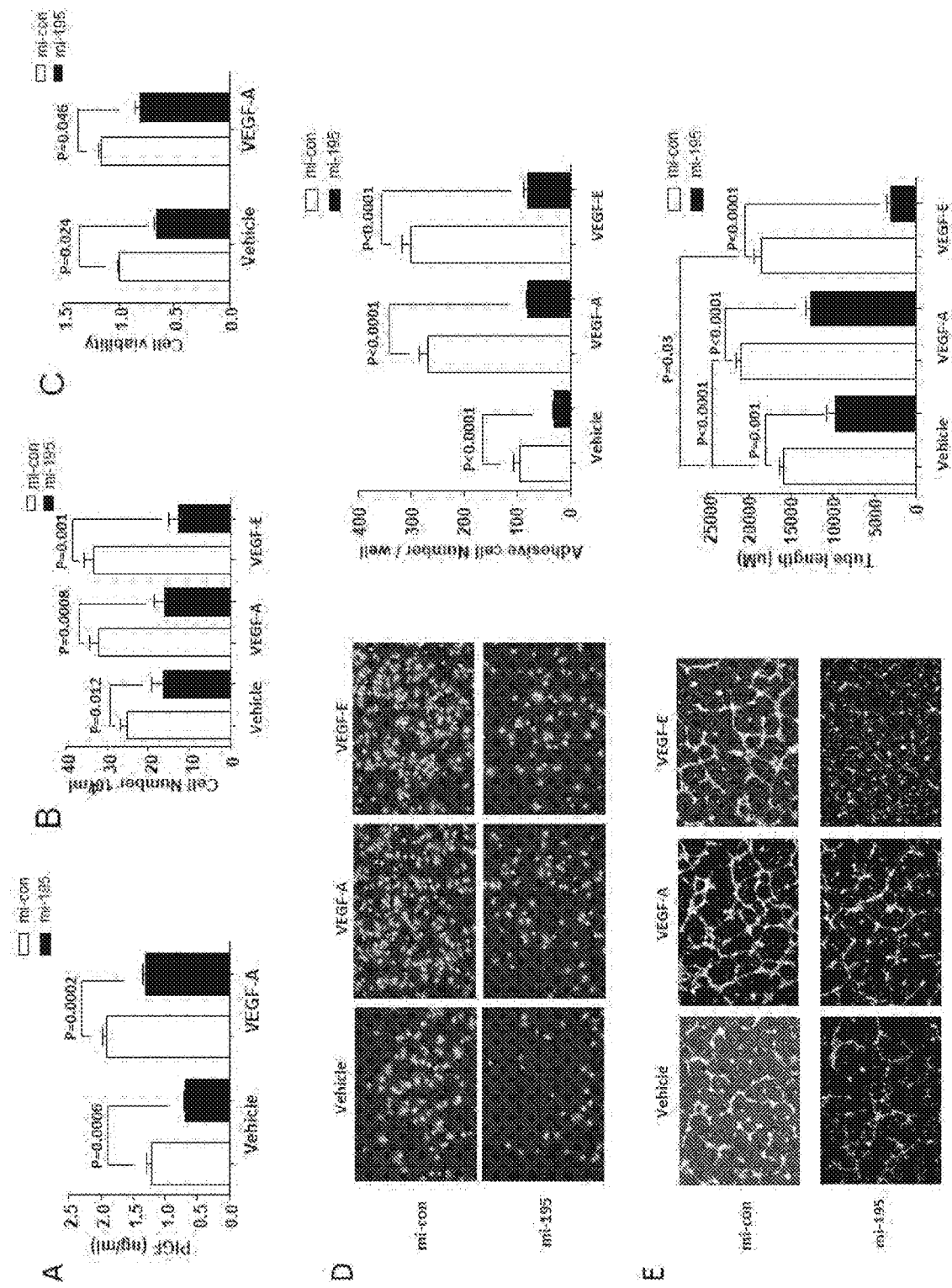

Results:

miR-195 Expression is Elevated in Severe Preeclampsia Patient and Animal Models, IUGR, Obesity Pregnant Women Various microarray studies revealed that miR-195 expression was dysregulated in the placentas of preeclamptic women (Xu et al., 2014; Zhu et al., 2009; Hu et al., 2009). Thus we examined the expression pattern of miR-195 in different human tissues that are related to the pathogenesis of preeclampsia. First, the miR-195 expression in the placentas of pregnant women with different gestational age was determined by qPCR. The miR-195 expression in the $3^{rd}$ trimester placenta (N=4) was up-regulated by 12.5-fold and 8.9-fold respectively compared to $1^{st}$ (N=6) and $2^{nd}$ (N=6) trimester placenta (FIG. 21A). Furthermore, as obesity pregnant women pose a high risk to preeclampsia, we examined the miR-195 expression in the adipose tissues of obesity pregnant women. The miR-195 expression in the visceral (N=25) and subcutaneous fat (N=24) of obesity pregnant women was increased by 2.28-fold and 7.8-fold respectively compared to lean pregnant women (N=20-22) (FIGS. 22B and C).

Although various microarray studies demonstrated the dysregulated expression of miR-195 in preeclampsia, the results from these studies are contradictive. More importantly, the placental samples used in these studies were collected from late gestational age of preeclampsia women range from 34.7 to 35.9 weeks. To investigate the miR-195 expression in more precisely defined early stage severe preeclampsia patients, the placental samples from preeclampsia women with an average gestational age of 29.7 weeks were collected and examined for miR-195 expression by qPCR. Quantitative PCR revealed that miR-195 expression in the preeclamptic placenta (N=14) and IUGR placenta (N=12) was increased by 10.9-fold and 2.6-fold respectively compared to gestation age matched control normotensive placenta (N=17) (FIG. 21D).

To further confirm the up-regulation of miR-195 in preeclampsia, the expression of miR-195 was examined in two animal models of preeclampsia. The pregnant mice receiving ad-sFlt-1 adenovirus injection (N=5) exhibited significant increased placental miR-195 level (FIG. 22E) as well as elevated sFlt-1 expression and mean artery pressure compared to ad-CMV control virus injected mice (N=7) (FIG. 26). Moreover, the miR-195 expression in placenta of pregnant Sprague Dawley rats that undergone reduced uterine perfusion pressure surgery (N=17) was also increased by 7.7-fold compared to normal pregnant rat (N=12, FIG. 21F). Taken together, these data suggest that miR-195 elevation is associated with pathogenesis of preeclampsia.

Hypoxia and Inflammatory Cytokines Elevates miR-195 Expression

Preeclamptic placenta is associated with hypoxia, inflammation condition as well as the elevation of VEGF and FGF-2 growth factors (Hunter et al., 2000; Ozkan et al., 2008), thus the miR-195 expression in the endothelial cells and placental explants under hypoxia and inflammation stimulation was determined by qPCR. Stimulation of mixed inflammatory cytokines in HUVEC cells increased miR-195 by approximate 43% (FIG. 21G). Furthermore, the combination of hypoxia and inflammatory cytokine mixture stimulation increased miR-195 expression by 138% and 48% in HUVECs and placental explants respectively (FIGS. 21H and I). These data confirmed that miR-195 expression is regulated by the pathological conditions that associated with preeclamptic placenta.

MiR-195 Modulates PlGF Expression in Endothelial Cells

The release of anti-angiogenic factors, sFlt-1 and sEng, and the inhibition of placental growth factor (PlGF) expression are the main cause of preeclampsia (Powe et al., 2011; Ahmad and Ahmed, 2004), therefore we examined whether miR-195 modulates sFlt-1, sEng or PlGF expression in endothelial cells. HUVECs were transfected with mi-195 to over-express miR-195 (FIG. 26) and the sFlt-1, sEng and PlGF release was examined by ELISA. Although overexpression of miR-195 in HUVECs did not change sFlt-1 and sEng expression, the PlGF level was significantly reduced under both vehicle and VEGF stimulation (FIG. 22A). As a result, the ratio of sFlt-1/PlGF was increased. These data further support the concept that miR-195 upregulation may contribute to the pathogenesis of preeclampsia.

MiR-195 Inhibits Endothelial Cell Proliferation, Viability, Adhesion and In Vitro Tube Formation, but Promotes Cell Migration Since the impaired endothelium is the main cause of preeclampsia, we tested whether miR-195 modulates endothelial cell functions. HUVECs were transfected with synthetic mimic (mi-195) and the cell proliferation assay was performed. Overexpression of miR-195 decreased cell number by 35% to 62% compared to control under vehicle, VEGF-A or VEGF-E stimulation (FIG. 22B). Moreover, MTT assay in the HUVECs transfected with mi-195 further confirmed that miR-195 overexpression decreased cell viability by 35% or 31% under vehicle or VEGF stimulation respectively (FIG. 22C).

The effect of miR-195 overexpression in endothelial cell adhesion was also tested. The adhesive ability was dramatically decreased in the mi-195 transfected cells regardless the stimulation of VEGF-A or VEGF-E. Cell counting confirmed an approximate 70% reduction of adhesive cells in the mi-195 transfected HUVECs under vehicle, VEGF-A or VEGF-E stimulation compared to mi-con transfected cells (FIG. 22D).

Since miR-195 inhibits angiogenesis in tumor cells, we speculated that miR-195 also inhibits angiogenesis in placental endothelial cells to contribute to the pathogenesis of preeclampsia. HUVECs transfected with mi-195 exhibited decreased tube formation on Matrigel under vehicle, VEGF-A or VEGF-E stimulation (FIG. 22E). Quantitative analysis revealed a 40% reduction in the tube formation of mi-195 transfected cells under vehicle condition and 40% to 84% reduction under VEGF-A or VEGF-E stimulation.

Figures 23A, 23B:
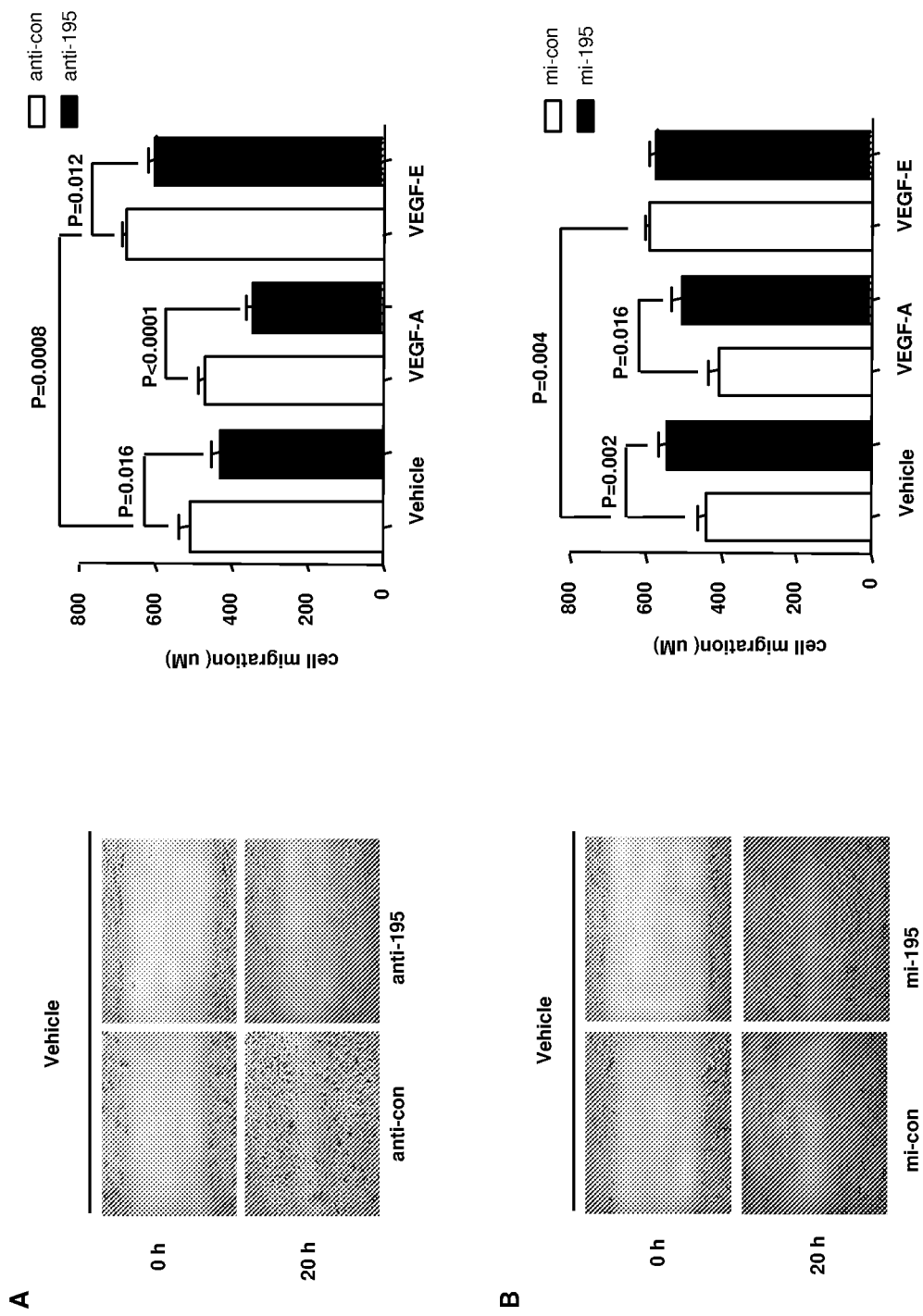

Moreover, the role of miR-195 in endothelial cell migration was determined by scratch assay. HUVECs transfected with anti-195 showed 11% to 26% decrease of migration ability compared to anti-con transfected control cells under vehicle or VGEF stimulation (FIG. 23A). Conversely, Overexpression of miR-195 in HUVECs significantly increased cell migration ability by approximate 1.25-fold under vehicle or VEGF-A stimulation (FIG. 23B).

MiR-195 Directly Targets eNOS in Endothelial Cells

To identify the direct targets of miR-195, gene expression microarray was performed using RNA samples from mi-195 and mi-con transfected HUVEC cells. The 10 up-regulated and 12 down-regulated genes upon miR-152 over-expression were selected with ±1.25-fold cut off. These expression altered genes have broad functions on vascular remodeling, cell adhesion, mobility and angiogenesis. Moreover, the down-regulated genes were further analyzed using online prediction tools to confirm the possible direct targets of miR-195 by sequence alignment. Finally, four down-regulated genes were selected for candidates of miR-195 direct target.

Figures 24A, 24B, 24C, 24D, 24E, 24F, 24G, 24H:
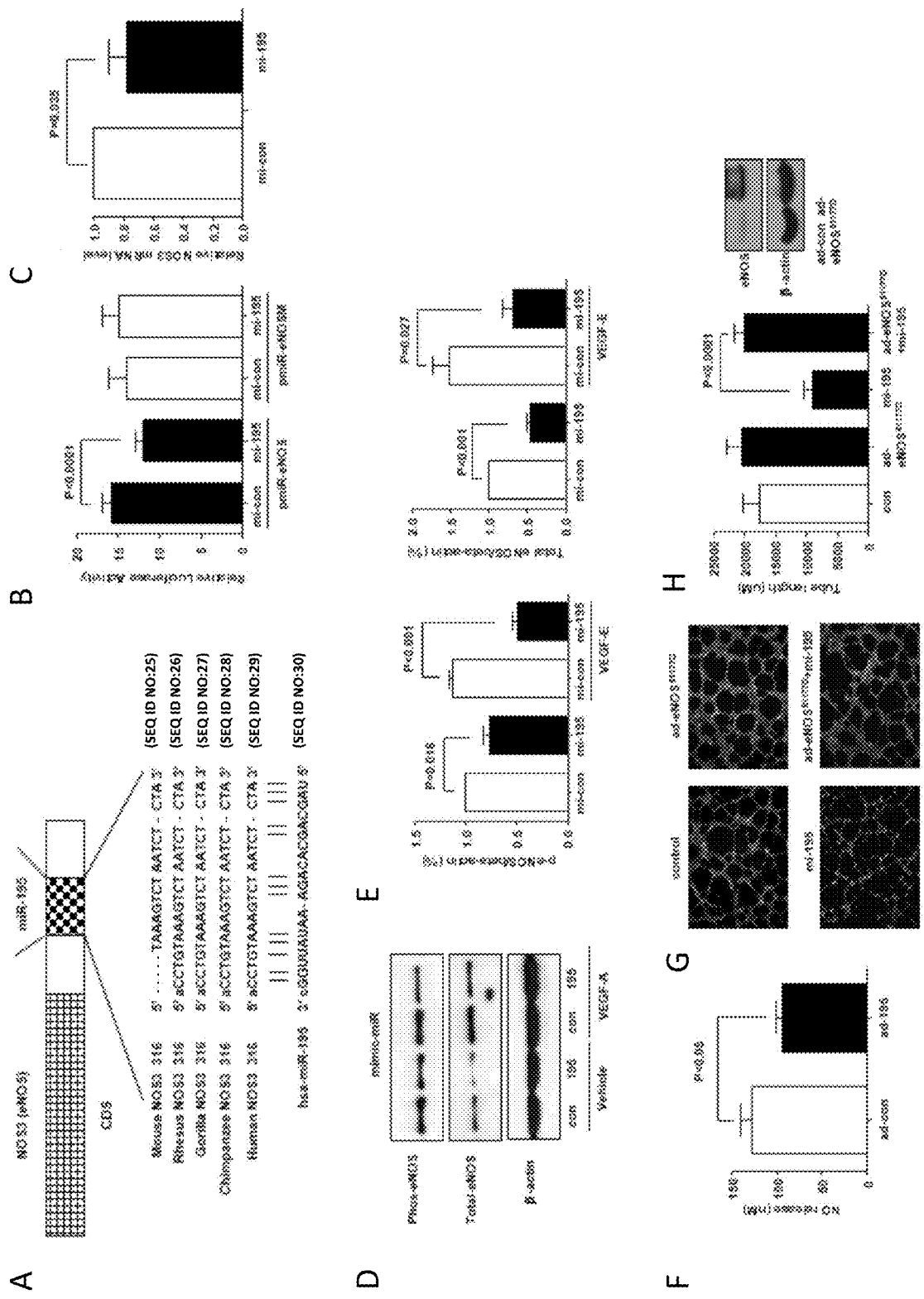

Among these direct targets, eNOS was the most important and well characterized in the literature. First, eNOS was predicted to be miR-195 direct target by the online prediction tools in various animal species (FIG. 24A). Furthermore, microRNA target assay proved that transfection of mi-195 significantly inhibited luciferase activity in the pmiR-eNOS transfected HEK293 cells, but not in the eNOS UTR mutant plasmid, pmiR-eNOSM, transfected cells (FIG. 24B; FIG. 27). The luciferase assay data was further supported by the evidence that eNOS mRNA and protein levels were decreased in the HUVECs transfected with mi-195. Quantitative PCR revealed a 22% decrease in mi-195 transfected HUVECs (FIG. 24C) and western blot using antibodies against total eNOS and phosphor-eNOS demonstrated an approximate 55% reduction of total eNOS and 24% to 56% reduction of phosphor-eNOS in mi-195 transfected cells (FIGS. 24D and E). More importantly, the release of NO gas in the HUVECs transfected with mi-195 was reduced by 27% compared to mi-con transfected cells (FIG. 24F). Finally, in order to validate that eNOS is the downstream effector of miR-195 mediated endothelial dysfunction, we tested whether overexpression of eNOS could rescue the mi-195 mediated inhibition of angiogenesis. As expected, miR-195 overexpression decreased spontaneously tube formation, while overexpression of eNOS$^{S1177D}$ completely recovered mi-195 mediated inhibition of tube-like structure in HUVEC cells (FIGS. 24G and H).

REFERENCE

Ahmad S, Ahmed A. Elevated placental soluble vascular endothelial growth factor receptor-1 inhibits angiogenesis in preeclampsia. *Circ Res.* 2004; 95:884-891.

Bussolati B, Dunk C, Grohman M, Kontos C D, Mason J, Ahmed A. Vascular endothelial growth factor receptor-1 modulates vascular endothelial growth factor-mediated angiogenesis via nitric oxide. *Am J Pathol* 2001; 159: 993-1008.

Sibai B, Dekker G, Kupferminc M. Pre-eclampsia. *Lancet.* 2005; 365: 785-799.

Steegers E A, von Dadelszen P, Duvekot J J, Pijnenborg R. Pre-eclampsia. *Lancet.* 2010; 376: 631-644.

Hladunewich M, Karumanchi S A, Lafayette R. Pathophysiology of the clinical manifestations of preeclampsia. *Clin J Am Soc Nephrol.* 2007; 2:543-549.

Silasi M, Cohen B, Karumanchi S A, Rana S. Abnormal placentation, angiogenic factors, and the pathogenesis of preeclampsia. *Obstet Gynecol Clin North Am.* 2010; 37:239-253.

Maynard S, Epstein F H, Karumanchi S A. Preeclampsia and angiogenic imbalance. *Annu Rev Med.* 2008; 59: 61-78.

Wang A, Rana S, Karumanchi S A. Preeclampsia: the role of angiogenic factors in its pathogenesis. *Physiology (Bethesda).* 2009; 24: 147-158.

Ramma W, Ahmed A. Is inflammation the cause of preeclampsia? *Biochem Soc Trans.* 2011; 39: 1619-1627.

Ramma W, Buhimschi I A, Zhao G, Dulay A T, Nayeri U A, Buhimschi C S, Ahmed A. The elevation in circulating anti-angiogenic factors is independent of markers of neutrophil activation in preeclampsia. *Angiogenesis.* 2012; 15:341-348.

Lockwood C J, Yen C F, Basar M, Kayisli U A, Martel M, Buhimschi I, Buhimschi C, Huang S J, Krikun G, Schatz F. Preeclampsia-related inflammatory cytokines regulate interleukin-6 expression in human decidual cells. *Am J Pathol.* 2008; 172: 1571-1579.

Powe C E, Levine R J, Karumanchi S A. Preeclampsia, a disease of the maternal endothelium: the role of antiangiogenic factors and implications for later cardiovascular disease. *Circulation.* 2011; 123: 2856-2869.

Poston L. Endothelial dysfunction in pre-eclampsia. *Pharmacol Rep.* 2006; 58 Suppl: 69-74.

Soleymanlou N, Jurisica I, Nevo O, Ietta F, Zhang X, Zamudio S, Post M, Caniggia I. Molecular evidence of placental hypoxia in preeclampsia. *J Clin Endocrinol Metab.* 2005; 90:4299-4308.

Grill S, Rusterholz C, Zanetti-Dallenbach R, Tercanli S, Holzgreve W, Hahn S, Lapaire O. Potential markers of preeclampsia—a review. *Reprod Biol Endocrinol.* 2009; 7: 70-83.

Bartel D P. MicroRNAs: target recognition and regulatory functions. *Cell.* 2009; 136:215-233.

Lewis B P, Shih I H, Jones-Rhoades M W, Bartel D P, Burge C B. Prediction of mammalian microRNA targets. *Cell.* 2003; 115: 787-798.

Williams A E. Functional aspects of animal microRNAs. *Cell Mol Life Sci.* 2008; 65: 545-562.

He L, Hannon G J. MicroRNAs: small RNAs with a big role in gene regulation. *Nat Rev Genet.* 2004; 5: 522-531.

Zhu X M, Han T, Sargent I L, Yin G W, Yao Y Q. Differential expression profile of microRNAs in human placentas from preeclamptic pregnancies vs normal pregnancies. *Am J Obstet Gynecol.* 2009; 200: 661.e1-7.

Hu Y, Li P, Hao S, Liu L, Zhao J, Hou Y. Differential expression of microRNAs in the placentae of Chinese patients with severe pre-eclampsia. *Clin Chem Lab Med.* 2009; 47: 923-929.

Pineles B L, Romero R, Montenegro D, Tarca A L, Han Y M, Kim Y M, Draghici S, Espinoza J, Kusanovic J P, Mittal P, Hassan S S, Kim C J. Distinct subsets of microRNAs are expressed differentially in the human placentas of patients with preeclampsia. *Am J Obstet Gynecol.* 2007; 196: 261.e1-6.

Mayor-Lynn K, Toloubeydokhti T, Cruz A C, Chegini N. Expression profile of microRNAs and mRNAs in human placentas from pregnancies complicated by preeclampsia and preterm labor. *Reprod Sci.* 2011; 18:46-56.

Enquobahrie D A, Abetew D F, Sorensen T K, Willoughby D, Chidambaram K, Williams M A. Placental microRNA expression in pregnancies complicated by preeclampsia. *Am J Obstet Gynecol.* 2011; 204: 178.e12-21.

Noack F, Ribbat-Idel J, Thorns C, Chiriac A, Axt-Fliedner R, Diedrich K, Feller A C. miRNA expression profiling in formalin-fixed and paraffin-embedded placental tissue samples from pregnancies with severe preeclampsia. *J Perinat Med.* 2011; 39: 267-271.

Zhang Y, Diao Z, Su L, Sun H, Li R, Cui H, Hu Y. MicroRNA-155 contributes to preeclampsia by down-regulating CYR61. *Am J Obstet Gynecol.* 2010; 202: 466.e1-7.

Cheng W, Liu T, Jiang F, Liu C, Zhao X, Gao Y, Wang H, Liu Z. microRNA-155 regulates angiotensin II type 1 receptor expression in umbilical vein endothelial cells from severely pre-eclamptic pregnant women. *Int J Mol Med.* 2011; 27: 393-399.

Zhang Y, Fei M, Xue G, Zhou Q, Jia Y, Li L, Xin H, Sun S. Elevated levels of hypoxia-inducible microRNA-210 in pre-eclampsia: new insights into molecular mechanisms for the disease. *J Cell Mol Med.* 2012; 16: 249-259.

Dai Y, Diao Z, Sun H, Li R, Qiu Z, Hu Y. MicroRNA-155 is involved in the remodelling of human-trophoblast-derived HTR-8/SVneo cells induced by lipopolysaccharides. *Hum Reprod.* 2011; 26: 1882-1891.

Lee D C, Romero R, Kim J S, Tarca A L, Montenegro D, Pineles B L, Kim E, Lee J, Kim S Y, Draghici S, Mittal P, Kusanovic J P, Chaiworapongsa T, Hassan S S, Kim C J. miR-210 targets iron-sulfur cluster scaffold homologue in human trophoblast cell lines: siderosis of interstitial trophoblasts as a novel pathology of preterm preeclampsia and small-for-gestational-age pregnancies. *Am J Pathol.* 2011; 179: 590-602.

Dai Y, Qiu Z, Diao Z, Shen L, Xue P, Sun H, Hu Y. MicroRNA-155 inhibits proliferation and migration of human extravillous trophoblast derived HTR-8/SVneo cells via down-regulating cyclin D1. *Placenta.* 2012; 33: 824-829.

Wang Y, Fan H, Zhao G, Liu D, Du L, Wang Z, Hu Y, Hou Y. miR-16 inhibits the proliferation and angiogenesis-regulating potential of mesenchymal stem cells in severe pre-eclampsia. *FEBS* 1 2012; 279: 4510-4524.

Muralimanoharan S, Maloyan A, Mele J, Guo C, Myatt L G, Myatt L. MIR-210 modulates mitochondrial respiration in placenta with preeclampsia. *Placenta.* 2012; 33: 816-823.

Li P, Guo W, Du L, Zhao J, Wang Y, Liu L, Hu Y, Hou Y. microRNA-29b contributes to pre-eclampsia through its effects on apoptosis, invasion and angiogenesis of trophoblast cells. *Clin Sci (Lond).* 2013; 124: 27-40.

Liu L, Wang Y, Fan H, Zhao X, Liu D, Hu Y, Kidd A R 3rd, Bao J, Hou Y. MicroRNA-181a regulates local immune balance by inhibiting proliferation and immunosuppressive properties of mesenchymal stem cells. *Stem Cells.* 2012; 30: 1756-1770.

Luo L, Ye G, Nadeem L, Fu G, Yang B B, Honarparvar E, Dunk C, Lye S, Peng C. MicroRNA-378a-5p promotes trophoblast cell survival, migration and invasion by targeting Nodal. *J Cell Sci.* 2012; 125: 3124-3132.

Xiang Y, Ma N, Wang D, Zhang Y, Zhou J, Wu G, Zhao R, Huang H, Wang X, Qiao Y, Li F, Han D, Wang L, Zhang G, Gao X. MiR-152 and miR-185 co-contribute to ovarian cancer cells cisplatin sensitivity by targeting DNMT1 directly: a novel epigenetic therapy independent of decitabine. *Oncogene.* 2013; doi: 10.1038/onc.2012.575.

Ji W, Yang L, Yuan J, Yang L, Zhang M, Qi D, Duan X, Xuan A, Zhang W, Lu J, Zhuang Z, Zeng G. MicroRNA-152 targets DNA methyltransferase 1 in NiS-transformed cells via a feedback mechanism. *Carcinogenesis.* 2013; 34: 446-453.

Huang J, Wang Y, Guo Y, Sun S. Down-regulated microRNA-152 induces aberrant DNA methylation in hepatitis B virus-related hepatocellular carcinoma by targeting DNA methyltransferase 1. *Hepatology.* 2010; 52: 60-70.

Braconi C, Huang N, Patel T. MicroRNA-dependent regulation of DNA methyltransferase-1 and tumor suppressor gene expression by interleukin-6 in human malignant cholangiocytes. *Hepatology.* 2010; 51: 881-890.

Zhou X, Zhao F, Wang Z N, Song Y X, Chang H, Chiang Y, Xu H M. Altered expression of miR-152 and miR-148a in ovarian cancer is related to cell proliferation. *Oncol Rep.* 2012; 27: 447-454.

Mancini M, Saintigny G, Mahe C, Annicchiarico-Petruzzelli M, Melino G, Candi E. MicroRNA-152 and -181a participate in human dermal fibroblasts senescence acting on cell adhesion and remodeling of the extra-cellular matrix. *Aging (Albany N.Y.).* 2012; 4:843-853.

Zhu X M, Han T, Wang X H, Li Y H, Yang H G, Luo Y N, Yin G W, Yao Y Q. Overexpression of miR-152 leads to reduced expression of human leukocyte antigen-G and increased natural killer cell mediated cytolysis in JEG-3 cells. *Am J Obstet Gynecol.* 2010; 202:592.e1-7.

Hiroki E, Akahira J, Suzuki F, Nagase S, Ito K, Suzuki T, Sasano H, Yaegashi N. Changes in microRNA expression levels correlate with clinicopathological features and prognoses in endometrial serous adenocarcinomas. *Cancer Sci.* 2010; 101: 241-249.

Tsuruta T, Kozaki K, Uesugi A, Furuta M, Hirasawa A, Imoto I, Susumu N, Aoki D, Inazawa J. miR-152 is a tumor suppressor microRNA that is silenced by DNA hypermethylation in endometrial cancer. *Cancer Res.* 2011; 71:6450-6462.

Tsuruta T, Kozaki K, Uesugi A, Furuta M, Hirasawa A, Imoto I, Susumu N, Aoki D, Inazawa J. miR-152 is a tumor suppressor microRNA that is silenced by DNA hypermethylation in endometrial cancer. *Cancer Res.* 2011; 71:6450-6462.

Chen Y, Song Y, Wang Z, Yue Z, Xu H, Xing C, Liu Z. Altered expression of MiR-148a and MiR-152 in gastro-intestinal cancers and its clinical significance. *J Gastrointest Surg.* 2010; 14: 1170-1179.

Wang X Y, Wu M R, Liu F, Li Y, Li N, Li G Y, Shen S R. Differential miRNA expression and their target genes between NGX6-positive and negative colon cancer cells. *Mol Cell Biochem.* 2010; 345:283-290.

Stumpel D J, Schotte D, Lange-Turenhout E A, Schneider P, Seslij a L, de Menezes R X, Marquez V E, Pieters R, den Boer M L, Stam R W. Hypermethylation of specific microRNA genes in MLL-rearranged infant acute lymphoblastic leukemia: major matters at a micro scale. *Leukemia.* 2011; 25:429-439.

Kitano K, Watanabe K, Emoto N, Kage H, Hamano E, Nagase T, Sano A, Murakawa T, Nakajima J, Goto A, Fukayama M, Yatomi Y, Ohishi N, Takai D. CpG island methylation of microRNAs is associated with tumor size and recurrence of non-small-cell lung cancer. *Cancer Sci.* 2011; 102: 2126-2131.

Zheng X, Chopp M, Lu Y, Buller B, Jiang F. MiR-15b and miR-152 reduce glioma cell invasion and angiogenesis via NRP-2 and MMP-3. *Cancer Lett.* 2013; 329: 146-154.

Xu Q, Jiang Y, Yin Y, Li Q, He J, Jing Y, Qi Y T, Xu Q, Li W, Lu B, Peiper S S, Jiang B H, Liu L Z. A regulatory circuit of miR-148a/152 and DNMT1 in modulating cell transformation and tumor angiogenesis through IGF-IR and IRS1. *J Mol Cell Biol.* 2013; 5:3-13.

Manaster I, Goldman-Wohl D, Greenfield C, Nachmani D, Tsukerman P, Hamani Y, Yagel S, Mandelboim O. MiRNA-mediated control of HLA-G expression and function. *PLoS One.* 2012; 7: e33395.

Cudmore M, Ahmad S, Al-Ani B, Fujisawa T, Coxall H, Chudasama K, Devey L R, Wigmore S J, Abbas A, Hewett P W, Ahmed A. Negative regulation of soluble Flt-1 and soluble endoglin release by heme oxygenase-1. *Circulation.* 2007; 115:1789-1797.

McCarthy F P, Drewlo S, Kingdom J, Johns E J, Walsh S K, Kenny L C. Peroxisome proliferator-activated receptor-γ as a potential therapeutic target in the treatment of preeclampsia. *Hypertension.* 2011; 58:280-286.

Yang Q, Lu J, Wang S, Li H, Ge Q, Lu Z. Application of next-generation sequencing technology to profile the circulating microRNAs in the serum of preeclampsia versus normal pregnant women. *Clin Chim Acta.* 2011; 412: 2167-2173.

Wu L, Zhou H, Lin H, Qi J, Zhu C, Gao Z, Wang H. Circulating microRNAs are elevated in plasma from severe preeclamptic pregnancies. *Reproduction.* 2012; 143: 389-397.

Hromadnikova I, Kotlabova K, Doucha J, Dlouha K, Krofta L. Absolute and relative quantification of placenta-specific micrornas in maternal circulation with placental insufficiency-related complications. *J Mol Dia.* 2012; 14: 160-167.

Pan M, Ge Q, Li H, Yang Q, Lu J, Zhang D, Lu Z. Sequencing the miRNAs in maternal plasma from women before and after parturition. *J Nanosci Nanotechnol.* 2012; 12: 4035-4043.

De Vivo A, Baviera G, Giordano D, Todarello G, Corrado F, D'anna R. Endoglin, PlGF and sFlt-1 as markers for predicting pre-eclampsia. *Acta Obstet Gynecol Scand.* 2008; 87:837-842.

Verlohren S, Herraiz I, Lapaire O, Schlembach D, Moertl M, Zeisler H, Calda P, Holzgreve W, Galindo A, Engels T, Denk B, Stepan H. The sFlt-1/PlGF ratio in different types of hypertensive pregnancy disorders and its prognostic potential in preeclamptic patients. *Am J Obstet Gynecol.* 2012; 206:58.e1-8.

Baumwell S, Karumanchi S A. Pre-eclampsia: clinical manifestations and molecular mechanisms. *Nephron Clin Pract.* 2007; 106:c72-81.

Hood J D, Cheresh D A. Role of integrins in cell invasion and migration. *Nat Rev Cancer.* 2002; 2:91-100.

Wang Q Y, Zhang Y, Shen Z H, Chen H L. alpha1,3 fucosyltransferase-VII up-regulates the mRNA of alpha5 integrin and its biological function. *J Cell Biochem.* 2008; 104:2078-2090.

Qin L, Chen X, Wu Y, Feng Z, He T, Wang L, Liao L, Xu J. Steroid receptor coactivator-1 upregulates integrin $\alpha_5$ expression to promote breast cancer cell adhesion and migration. *Cancer Res.* 2011; 71:1742-1751.

Francis S E, Goh K L, Hodivala-Dilke K, Bader B L, Stark M, Davidson D, Hynes R O. Central roles of alpha5beta1 integrin and fibronectin in vascular development in mouse embryos and embryoid bodies. *Arterioscler Thromb Vasc Biol.* 2002; 22:927-933.

Bonauer A, Carmona G, Iwasaki M, Mione M, Koyanagi M, Fischer A, Burchfield J, Fox H, Doebele C, Ohtani K, Chavakis E, Potente M, Tjwa M, Urbich C, Zeiher A M, Dimmeler S. MicroRNA-92a controls angiogenesis and functional recovery of ischemic tissues in mice. *Science.* 2009; 324:1710-1713.

Moh M C, Shen S. The roles of cell adhesion molecules in tumor suppression and cell migration: a new paradox. *Cell Adh Migr.* 2009; 3:334-336.

Grzesiak J J, Smith K C, Chalberg C, Burton D W, Deftos L J, Bouvet M. Type I collagen and divalent cation shifts disrupt cell-cell adhesion, increase migration, and decrease PTHrP, IL-6, and IL-8 expression in pancreatic cancer cells. *Int J Gastrointest Cancer.* 2005; 36:131-146.

Leslie K, Thilaganathan B, Papageorghiou A. Early prediction and prevention of pre-eclampsia. *Best Pract Res Clin Obstet Gynaecol.* 2011; 25:343-354.

Bujold E, Morency A M, Roberge S, Lacasse Y, Forest J C, Giguère Y. Acetylsalicylic acid for the prevention of preeclampsia and intra-uterine growth restriction in women with abnormal uterine artery Doppler: a systematic review and meta-analysis. *J Obstet Gynaecol Can.* 2009; 31:818-826.

Williams Z, Ben-Dov I Z, Elias R, Mihailovic A, Brown M, Rosenwaks Z, Tuschl T. Comprehensive profiling of circulating microRNA via small RNA sequencing of cDNA libraries reveals biomarker potential and limitations. *Proc Natl Acad Sci USA.* 2013; 110:4255-4260.

Pennington K A, Schlitt J M, Jackson D L, Schulz L C, Schust D J. Preeclampsia: multiple approaches for a multifactorial disease. *Dis Model Mech.* 2012; 5:9-18.

Murdoch C E, Shuler M, Haeussler D J, Kikuchi R, Bearelly P, Han J, Watanabe Y, Fuster J J, Walsh K, Ho Y S, Bachschmid M M, Cohen R A, Matsui R. Glutaredoxin-1 up-regulation induces soluble vascular endothelial growth factor receptor 1, attenuating post-ischemia limb revascularization. *J Biol Chem.* 2014; 289:8633-44.

Hunter Al, Aitkenhead M, Caldwell C, McCracken G, Wilson D, McClure N. Serum levels of vascular endothelial growth factor in preeclamptic and normotensive pregnancy. *Hypertension.* 2000; 36:965-969.

Ozkan S1, Vural B, Filiz S, Coştur P, Dalçik H. Placental expression of insulin-like growth factor-I, fibroblast growth factor-basic, and neural cell adhesion molecule in preeclampsia. *J Matern Fetal Neonatal Med.* 2008; 21:831-838.

REFERENCE

Sibai B, Dekker G, Kupferminc M. Pre-eclampsia. *Lancet.* 2005; 365: 785-799.

Steegers E A, von Dadelszen P, Duvekot J J, Pijnenborg R. Pre-eclampsia. *Lancet.* 2010; 376: 631-644.

Hladunewich M, Karumanchi S A, Lafayette R. Pathophysiology of the clinical manifestations of preeclampsia. *Clin J Am Soc Nephrol.* 2007; 2:543-549.

Silasi M, Cohen B, Karumanchi S A, Rana S. Abnormal placentation, angiogenic factors, and the pathogenesis of preeclampsia. *Obstet Gynecol Clin North Am.* 2010; 37:239-253.

Maynard S, Epstein F H, Karumanchi S A. Preeclampsia and angiogenic imbalance. *Annu Rev Med.* 2008; 59: 61-78.

Wang A, Rana S, Karumanchi S A. Preeclampsia: the role of angiogenic factors in its pathogenesis. *Physiology (Bethesda).* 2009; 24: 147-158.

Ramma W, Ahmed A. Is inflammation the cause of pre-eclampsia? *Biochem Soc Trans.* 2011; 39: 1619-1627.

Ramma W, Buhimschi I A, Zhao G, Dulay A T, Nayeri U A, Buhimschi C S, Ahmed A. The elevation in circulating anti-angiogenic factors is independent of markers of neutrophil activation in preeclampsia. *Angiogenesis.* 2012; 15:341-348.

Lockwood C J, Yen C F, Basar M, Kayisli U A, Martel M, Buhimschi I, Buhimschi C, Huang S J, Krikun G, Schatz F. Preeclampsia-related inflammatory cytokines regulate interleukin-6 expression in human decidual cells. *Am J Pathol.* 2008; 172: 1571-1579.

Powe C E, Levine R J, Karumanchi S A. Preeclampsia, a disease of the maternal endothelium: the role of antiangiogenic factors and implications for later cardiovascular disease. *Circulation.* 2011; 123: 2856-2869.

Poston L. Endothelial dysfunction in pre-eclampsia. *Pharmacol Rep.* 2006; 58 Suppl: 69-74.

Soleymanlou N, Jurisica I, Nevo O, Ietta F, Zhang X, Zamudio S, Post M, Caniggia I. Molecular evidence of placental hypoxia in preeclampsia. *J Clin Endocrinol Metab.* 2005; 90:4299-4308.

Grill S, Rusterholz C, Zanetti-Dallenbach R, Tercanli S, Holzgreve W, Hahn S, Lapaire O. Potential markers of preeclampsia—a review. *Reprod Biol Endocrinol.* 2009; 7: 70-83.

Bartel D P. MicroRNAs: target recognition and regulatory functions. *Cell.* 2009; 136:215-233.

Lewis B P, Shih I H, Jones-Rhoades M W, Bartel D P, Burge C B. Prediction of mammalian microRNA targets. *Cell.* 2003; 115: 787-798.

Williams A E. Functional aspects of animal microRNAs. *Cell Mol Life Sci.* 2008; 65: 545-562.

He L, Hannon G J. MicroRNAs: small RNAs with a big role in gene regulation. *Nat Rev Genet.* 2004; 5: 522-531.

Hu Y, Li P, Hao S, Liu L, Zhao J, Hou Y. Differential expression of microRNAs in the placentae of Chinese patients with severe pre-eclampsia. *Clin Chem Lab Med.* 2009; 47: 923-929.

Pineles B L, Romero R, Montenegro D, Tarca A L, Han Y M, Kim Y M, Draghici S, Espinoza J, Kusanovic J P, Mittal P, Hassan S S, Kim C J. Distinct subsets of microRNAs are expressed differentially in the human placentas of patients with preeclampsia. *Am J Obstet Gynecol.* 2007; 196: 261.e1-6.

Mayor-Lynn K, Toloubeydokhti T, Cruz A C, Chegini N. Expression profile of microRNAs and mRNAs in human placentas from pregnancies complicated by preeclampsia and preterm labor. *Reprod Sci.* 2011; 18:46-56.

Enquobahrie D A, Abetew D F, Sorensen T K, Willoughby D, Chidambaram K, Williams M A. Placental microRNA expression in pregnancies complicated by preeclampsia. *Am J Obstet Gynecol.* 2011; 204: 178.e12-21.

Noack F, Ribbat-Idel J, Thorns C, Chiriac A, Axt-Fliedner R, Diedrich K, Feller A C. miRNA expression profiling in formalin-fixed and paraffin-embedded placental tissue samples from pregnancies with severe preeclampsia. *J Perinat Med.* 2011; 39: 267-271.

Zhang Y, Diao Z, Su L, Sun H, Li R, Cui H, Hu Y. MicroRNA-155 contributes to preeclampsia by down-regulating CYR61. *Am J Obstet Gynecol.* 2010; 202: 466.e1-7.

Cheng W, Liu T, Jiang F, Liu C, Zhao X, Gao Y, Wang H, Liu Z. microRNA-155 regulates angiotensin II type 1 receptor expression in umbilical vein endothelial cells from severely pre-eclamptic pregnant women. *Int J Mol Med.* 2011; 27: 393-399.

Zhang Y, Fei M, Xue G, Zhou Q, Jia Y, Li L, Xin H, Sun S. Elevated levels of hypoxia-inducible microRNA-210 in pre-eclampsia: new insights into molecular mechanisms for the disease. *J Cell Mol Med.* 2012; 16: 249-259.

Dai Y, Diao Z, Sun H, Li R, Qiu Z, Hu Y. MicroRNA-155 is involved in the remodelling of human-trophoblast-derived HTR-8/SVneo cells induced by lipopolysaccharides. *Hum Reprod.* 2011; 26: 1882-1891.

Lee D C, Romero R, Kim J S, Tarca A L, Montenegro D, Pineles B L, Kim E, Lee J, Kim S Y, Draghici S, Mittal P, Kusanovic J P, Chaiworapongsa T, Hassan S S, Kim C J. miR-210 targets iron-sulfur cluster scaffold homologue in human trophoblast cell lines: siderosis of interstitial trophoblasts as a novel pathology of preterm preeclampsia and small-for-gestational-age pregnancies. *Am J Pathol.* 2011; 179: 590-602.

Dai Y, Qiu Z, Diao Z, Shen L, Xue P, Sun H, Hu Y. MicroRNA-155 inhibits proliferation and migration of human extravillous trophoblast derived HTR-8/SVneo cells via down-regulating cyclin D1. *Placenta.* 2012; 33: 824-829.

Wang Y, Fan H, Zhao G, Liu D, Du L, Wang Z, Hu Y, Hou Y. miR-16 inhibits the proliferation and angiogenesis-regulating potential of mesenchymal stem cells in severe pre-eclampsia. *FEBS J.* 2012; 279: 4510-4524.

Muralimanoharan S, Maloyan A, Mele J, Guo C, Myatt L G, Myatt L. MIR-210 modulates mitochondrial respiration in placenta with preeclampsia. *Placenta.* 2012; 33: 816-823.

Li P, Guo W, Du L, Zhao J, Wang Y, Liu L, Hu Y, Hou Y. microRNA-29b contributes to pre-eclampsia through its effects on apoptosis, invasion and angiogenesis of trophoblast cells. *Clin Sci (Lond).* 2013; 124: 27-40.

Liu L, Wang Y, Fan H, Zhao X, Liu D, Hu Y, Kidd A R 3rd, Bao J, Hou Y. MicroRNA-181a regulates local immune balance by inhibiting proliferation and immunosuppressive properties of mesenchymal stem cells. *Stem Cells.* 2012; 30: 1756-1770.

Luo L, Ye G, Nadeem L, Fu G, Yang B B, Honarparvar E, Dunk C, Lye S, Peng C. MicroRNA-378a-5p promotes trophoblast cell survival, migration and invasion by targeting Nodal. *J Cell Sci.* 2012; 125: 3124-3132.

Amer M, Elhefnawi M, El-Ahwany E, Awad A F, Gawad N A, Zada S, Tawab F M.

Hsa-miR-195 targets PCMT1 in hepatocellular carcinoma that increases tumor life span. *Tumour Biol.* 2014. [Epub ahead of print]

Zhao F L, Dou Y C, Wang X F, Han D C, Lv Z G, Ge S L, Zhang Y K. Serum microRNA-195 is down-regulated in breast cancer: a potential marker for the diagnosis of breast cancer. *Mol Biol Rep.* 2014; 41:5913-5922.

Jain M, Zhang L, Boufraqech M, Liu-Chittenden Y, Bussey K, Demeure M J, Wu X, Su L, Pacak K, Stratakis C A, Kebebew E. ZNF367 inhibits cancer progression and is targeted by miR-195. *PLoS One.* 2014; 9:e101423.

Guo H, Li W, Zheng T, Liu Z. miR-195 Targets HDGF to inhibit proliferation and invasion of NSCLC cells. *Tumour Biol.* 2014; 35:8861-8866.

Wang X, Wang Y, Lan H, Li J. miR-195 inhibits the growth and metastasis of NSCLC cells by targeting IGF1R. *Tumour Biol.* 2014; 35:8765-8770.

Wang L, Qian L, Li X, Yan J. MicroRNA-195 inhibits colorectal cancer cell proliferation, colony-formation and invasion through targeting CARMA3. *Mol Med Rep.* 2014; 10:473-478.

Yang Y, Li M, Chang S, Wang L, Song T, Gao L, Hu L, Li Z, Liu L, Yao J, Huang C. MicroRNA-195 acts as a tumor suppressor by directly targeting Wnt3a in HepG2 hepatocellular carcinoma cells. *Mol Med Rep.* 2014; 10:2643-2648.

Luo Q, Wei C, Li X, Li J, Chen L, Huang Y, Song H, Li D, Fang L. MicroRNA-195-5p is a potential diagnostic and therapeutic target for breast cancer. *Oncol Rep.* 2014; 31:1096-1102.

Fu M G, Li S, Yu T T, Qian L J, Cao R S, Zhu H, Xiao B, Jiao C H, Tang N N, Ma J J, Hua J, Zhang W F, Zhang H J, Shi R H. Differential expression of miR-195 in esophageal squamous cell carcinoma and miR-195 expression inhibits tumor cell proliferation and invasion by targeting of Cdc42. *FEBS Lett.* 2013; 587:3471-3479.

Chen Y Q, Wang X X, Yao X M, Zhang D L, Yang X F, Tian S F, Wang N S. Abated microRNA-195 expression protected mesangial cells from apoptosis in early diabetic renal injury in mice. *J Nephrol.* 2012; 25:566-576.

Mortuza R, Feng B, Chakrabarti S. miR-195 regulates SIRT1-mediated changes in diabetic retinopathy. *Diabetologia*. 2014; 57:1037-1046.

Yang W M, Jeong H J, Park S Y, Lee W. Saturated fatty acid-induced miR-195 impairs insulin signaling and glycogen metabolism in HepG2 cells. *FEBS Lett*. 2014; 5793: 00681-00684.

Ortega F J, Mercader J M, Moreno-Navarrete J M, Rovira O, Guerra E, Esteve E, Xifra G, Martínez C, Ricart W, Rieusset J, Rome S, Karczewska-Kupczewska M, Straczkowski M, Fernández-Real J M. Profiling of circulating microRNAs reveals common microRNAs linked to type 2 diabetes that change with insulin sensitization. *Diabetes Care*. 2014; 37:1375-1383.

Herrera B M, Lockstone H E, Taylor J M, Ria M, Barrett A, Collins S, Kaisaki P, Argoud K, Fernandez C, Travers M E, Grew J P, Randall J C, Gloyn A L, Gauguier D, McCarthy M I, Lindgren C M. Global microRNA expression profiles in insulin target tissues in a spontaneous rat model of type 2 diabetes. *Diabetologia*. 2010; 53:1099-1109.

Guo S T, Jiang C C, Wang G P, Li Y P, Wang C Y, Guo X Y, Yang R H, Feng Y, Wang F H, Tseng H Y, Thorne R F, Jin L, Zhang X D. MicroRNA-497 targets insulin-like growth factor 1 receptor and has a tumour suppressive role in human colorectal cancer. *Oncogene*. 2013; 32:1910-1920.

Long G, Wang F, Duan Q, Yang S, Chen F, Gong W, Yang X, Wang Y, Chen C, Wang D W. Circulating miR-30a, miR-195 and let-7b associated with acute myocardial infarction. *PLoS One*. 2012; 7:e50926.

You X Y, Huang J H, Liu B, Liu S J, Zhong Y, Liu S M. HMGA1 is a new target of miR-195 involving isoprenaline-induced cardiomyocyte hypertrophy. *Biochemistry (Mosc)*. 2014; 79:538-544.

van Rooij E, Sutherland L B, Liu N, Williams A H, McAnally J, Gerard R D, Richardson J A, Olson E N. A signature pattern of stress-responsive microRNAs that can evoke cardiac hypertrophy and heart failure. *Proc Natl Acad Sci USA*. 2006; 103:18255-18260.

Busk P K, Cirera S. MicroRNA profiling in early hypertrophic growth of the left ventricle in rats. *Biochem Biophys Res Commun*. 2010; 396:989-993.

Porrello E R, Johnson B A, Aurora A B, Simpson E, Nam Y J, Matkovich S J, Dorn G W 2nd, van Rooij E, Olson E N. MiR-15 family regulates postnatal mitotic arrest of cardiomyocytes. *Circ Res*. 2011; 109:670-679.

Zampetaki A, Attia R, Mayr U, Gomes R S, Phinikaridou A, Yin X, Langley S R, Willeit P, Lu R, Fanshawe B, Fava M, Barallobre-Barreiro J, Molenaar C, So P W, Abbas A, Jahangiri M, Waltham M, Botnar R, Smith A, Mayr M. Role of miR-195 in Aortic Aneurysmal Disease. *Circ Res*. 2014; 115:857-866.

Qin J, Liang H, Shi D, Dai J, Xu Z, Chen D, Chen X, Jiang Q. A panel of microRNAs as a new biomarkers for the detection of deep vein thrombosis. *J Thromb Thrombolysis*. 2014; Epub ahead of print.

Gu Y, Sun J, Groome L J, Wang Y. Differential miRNA expression profiles between the first and third trimester human placentas. *Am J Physiol Endocrinol Metab*. 2013; 304:E836-843.

Wang R, Zhao N, Li S, Fang J H, Chen M X, Yang J, Jia W H, Yuan Y, Zhuang S M. MicroRNA-195 suppresses angiogenesis and metastasis of hepatocellular carcinoma by inhibiting the expression of VEGF, VAV2, and CDC42. *Hepatology*. 2013; 58:642-653.

Xu P, Zhao Y, Liu M, Wang Y, Wang H, Li Y X, Zhu X, Yao Y, Wang H, Qiao J, Ji L, Wang Y L. Variations of microRNAs in human placentas and plasma from preeclamptic pregnancy. *Hypertension*. 2014; 63:1276-1284.

Zhu X M, Han T, Sargent I L, Yin G W, Yao Y Q. Differential expression profile of microRNAs in human placentas from preeclamptic pregnancies vs normal pregnancies. *Am J Obstet Gynecol*. 2009; 200: 661.e1-7.

Hu Y, Li P, Hao S, Liu L, Zhao J, Hou Y. Differential expression of microRNAs in the placentae of Chinese patients with severe pre-eclampsia. *Clin Chem Lab Med*. 2009; 47:923-929.

Huang P L. Endothelial nitric oxide synthase and endothelial dysfunction. *Curr Hypertens Rep*. 2003; 5:473-480.

Albrecht E W, Stegeman C A, Heeringa P, Henning R H, van Goor H. Protective role of endothelial nitric oxide synthase. *J Pathol*. 2003; 199:8-17.

Förstermann U, Münzel T. Endothelial nitric oxide synthase in vascular disease: from marvel to menace. *Circulation*. 2006; 113:1708-1714.

Duda D G, Fukumura D, Jain R K. Role of eNOS in neovascularization: NO for endothelial progenitor cells. *Trends Mol Med*. 2004; 10:143-145.

Lin M I, Sessa W C. Vascular endothelial growth factor signaling to endothelial nitric oxide synthase: more than a FLeeTing moment. *Circ Res*. 2006, 99: 666-668.

Fatini C, Sticchi E, Gensini F, Genuardi M, Tondi F, Gensini G F, Riviello C, Parretti E, Mello G, Abbate R. Endothelial nitric oxide synthase gene influences the risk of pre-eclampsia, the recurrence of negative pregnancy events, and the maternal-fetal flow. *J Hypertens*. 2006; 24:1823-1929.

Sun H X, Zeng D Y, Li R T, Pang R P, Yang H, Hu Y L, Zhang Q, Jiang Y, Huang L Y, Tang Y B, Yan G J, Zhou J G. Essential role of microRNA-155 in regulating endothelium-dependent vasorelaxation by targeting endothelial nitric oxide synthase. *Hypertension*. 2012; 60:1407-1414.

Ahmad S, Ahmed A. Elevated placental soluble vascular endothelial growth factor receptor-1 inhibits angiogenesis in preeclampsia. *Circ Res*. 2004; 95:884-891.

Cudmore M, Ahmad S, Al-Ani B, Fujisawa T, Coxall H, Chudasama K, Devey L R, Wigmore S J, Abbas A, Hewett P W, Ahmed A. Negative regulation of soluble Flt-1 and soluble endoglin release by heme oxygenase-1. *Circulation*. 2007; 115:1789-1797.

McCarthy F P, Drewlo S, Kingdom J, Johns E J, Walsh S K, Kenny L C. Peroxisome proliferator-activated receptor-γ as a potential therapeutic target in the treatment of preeclampsia. *Hypertension*. 2011; 58:280-286.

Bussolati B, Dunk C, Grohman M, Kontos C D, Mason J, Ahmed A. Vascular endothelial growth factor receptor-1 modulates vascular endothelial growth factor-mediated angiogenesis via nitric oxide. *Am J Pathol* 2001; 159: 993-1008.

Ahmad S, Hewett P W, Wang P, Al-Ani B, Cudmore M, Fujisawa T, Haigh J J, le Noble F, Wang L, Mukhopadhyay D, Ahmed A. Direct evidence for endothelial vascular endothelial growth factor receptor-1 function in nitric oxide-mediated angiogenesis. *Circ Res*. 2006; 99:715-722.

Hunter A l, Aitkenhead M, Caldwell C, McCracken G, Wilson D, McClure N.

Serum levels of vascular endothelial growth factor in preeclamptic and normotensive pregnancy. *Hypertension*. 2000; 36:965-969.

Ozkan S I, Vural B, Filiz S, Coştur P, Dalçik H. Placental expression of insulin-like growth factor-I, fibroblast growth factor-basic, and neural cell adhesion molecule in preeclampsia. *J Matern Fetal Neonatal Med.* 2008; 21:831-838.

REFERENCES

Cudmore M, Ahmad S, Al-Ani B, Fujisawa T, Coxall H, Chudasama K, Devey L R, Wigmore S J, Abbas A, Hewett P W, Ahmed A. Negative regulation of soluble Flt-1 and soluble endoglin release by heme oxygenase-1. *Circulation.* 2007; 115:1789-1797.

Ahmad S, Hewett P W, Al-Ani B, Sissaoui S, Fujisawa T, Cudmore M J, Ahmed A. Autocrine activity of soluble Flt-1 controls endothelial cell function and angiogenesis. *Vasc Cell.* 2011; 3:15.

Levine R J, Maynard S E, Qian C, Lim K H, England L J, Yu K F, Schisterman E F, Thadhani R, Sachs B P, Epstein F H, Sibai B M, Sukhatme V P, Karumanchi S A. Circulating angiogenic factors and the risk of preeclampsia. *N Engl J Med.* 2004; 350:672-683.

Venkatesha S, Toporsian M, Lam C, Hanai J, Mammoto T, Kim Y M, Bdolah Y, Lim K H, Yuan H T, Libermann T A, Stillman I E, Roberts D, D'Amore P A, Epstein F H, Sellke F W, Romero R, Sukhatme V P, Letarte M, Karumanchi S A. Soluble endoglin contributes to the pathogenesis of preeclampsia. *Nat Med.* 2006; 12:642-649.

Ramma W, Ahmed A. Is inflammation the cause of preeclampsia? *Biochem Soc Trans.* 2011; 39:1619-1627.

Kendall R L, Wang G, Thomas K A. Identification of a natural soluble form of the vascular endothelial growth factor receptor, FLT-1, and its heterodimerization with KDR. *Biochem Biophys Res Commun.* 1996; 226:324-328.

Wu F T, Stefanini M O, Mac Gabhann F, Kontos C D, Annex B H, Popel A S. A systems biology perspective on sVEGFR1: its biological function, pathogenic role and therapeutic use. *J Cell Mol Med.* 2010; 14:528-552.

Stepan H, Unversucht A, Wessel N, Faber R. Predictive value of maternal angiogenic factors in second trimester pregnancies with abnormal uterine perfusion. *Hypertension.* 2007; 49:818-824.

Bando H, Weich H A, Brokelmann M, Horiguchi S, Funata N, Ogawa T, Toi M. Association between intratumoral free and total VEGF, soluble VEGFR-1, VEGFR-2 and prognosis in breast cancer. *Br J Cancer.* 2005; 92:553-561.

Ebos J M, Bocci G, Man S, Thorpe P E, Hicklin D J, Zhou D, Jia X, Kerbel R S. A naturally occurring soluble form of vascular endothelial growth factor receptor 2 detected in mouse and human plasma. *Mol Cancer Res.* 2004; 2:315-326.

Lamszus K, Ulbricht U, Matschke J, Brockmann M A, Fillbrandt R, Westphal M. Levels of soluble vascular endothelial growth factor (VEGF) receptor 1 in astrocytic tumors and its relation to malignancy, vascularity, and VEGF-A. *Clin Cancer Res.* 2003; 9:1399-1405.

Jaroszewicz J, Januszkiewicz M, Flisiak R, Rogalska M, Kalinowska A, Wierzbicka I. Circulating vascular endothelial growth factor and its soluble receptors in patients with liver cirrhosis: possible association with hepatic function impairment. *Cytokine.* 2008; 44:14-17.

Blann A D, Belgore F M, McCollum C N, Silverman S, Lip P L, Lip G Y. Vascular endothelial growth factor and its receptor, Flt-1, in the plasma of patients with coronary or peripheral atherosclerosis, or Type II diabetes. *Clin Sci (Lond).* 2002; 102:187-194.

Findley C M, Mitchell R G, Duscha B D, Annex B H, Kontos C D. Plasma levels of soluble Tie2 and vascular endothelial growth factor distinguish critical limb ischemia from intermittent claudication in patients with peripheral arterial disease. *J Am Coll Cardiol.* 2008; 52:387-393.

Sibai B, Dekker G, Kupferminc M. Pre-eclampsia. *Lancet.* 2005; 365: 785-799. Steegers E A, von Dadelszen P, Duvekot J J, Pijnenborg R. Pre-eclampsia. *Lancet.* 2010; 376: 631-644.

Silasi M, Cohen B, Karumanchi S A, Rana S. Abnormal placentation, angiogenic factors, and the pathogenesis of preeclampsia. *Obstet Gynecol Clin North Am.* 2010; 37:239-253.

Maynard S, Epstein F H, Karumanchi S A. Preeclampsia and angiogenic imbalance. *Annu Rev Med.* 2008; 59: 61-78.

Maynard S E, Min J Y, Merchan J, Lim K H, Li J, Mondal S, Libermann T A, Morgan J P, Sellke F W, Stillman I E, Epstein F H, Sukhatme V P, Karumanchi S A. Excess placental soluble fms-like tyrosine kinase 1 (sFlt1) may contribute to endothelial dysfunction, hypertension, and proteinuria in preeclampsia. *J Clin Invest.* 2003; 111:649-658.

Powe C E, Levine R J, Karumanchi S A. Preeclampsia, a disease of the maternal endothelium: the role of antiangiogenic factors and implications for later cardiovascular disease. *Circulation.* 2011; 123: 2856-2869.

Costantine M M, Cleary K; Eunice Kennedy Shriver National Institute of Child Health and Human Development Obstetric—Fetal Pharmacology Research Units Network. Pravastatin for the prevention of preeclampsia in high-risk pregnant women. *Obstet Gynecol.* 2013; 121:349-353.

Bartel D P. MicroRNAs: target recognition and regulatory functions. *Cell.* 2009; 136:215-233.

Lewis B P, Shih I H, Jones-Rhoades M W, Bartel D P, Burge C B. Prediction of mammalian microRNA targets. *Cell.* 2003; 115: 787-798.

Williams A E. Functional aspects of animal microRNAs. *Cell Mol Life Sci.* 2008; 65: 545-562.

He L, Hannon G J. MicroRNAs: small RNAs with a big role in gene regulation. *Nat Rev Genet.* 2004; 5: 522-531.

Zhu X M, Han T, Sargent I L, Yin G W, Yao Y Q. Differential expression profile of microRNAs in human placentas from preeclamptic pregnancies vs normal pregnancies. *Am J Obstet Gynecol.* 2009; 200: 661.e1-7.

Hu Y, Li P, Hao S, Liu L, Zhao J, Hou Y. Differential expression of microRNAs in the placentae of Chinese patients with severe pre-eclampsia. *Clin Chem Lab Med.* 2009; 47: 923-929.

Pineles B L, Romero R, Montenegro D, Tarca A L, Han Y M, Kim Y M, Draghici S, Espinoza J, Kusanovic J P, Mittal P, Hassan S S, Kim C J. Distinct subsets of microRNAs are expressed differentially in the human placentas of patients with preeclampsia. *Am J Obstet Gynecol.* 2007; 196: 261.e1-6.

Mayor-Lynn K, Toloubeydokhti T, Cruz A C, Chegini N. Expression profile of microRNAs and mRNAs in human placentas from pregnancies complicated by preeclampsia and preterm labor. *Reprod Sci.* 2011; 18:46-56.

Enquobahrie D A, Abetew D F, Sorensen T K, Willoughby D, Chidambaram K, Williams M A. Placental microRNA expression in pregnancies complicated by preeclampsia. *Am J Obstet Gynecol.* 2011; 204: 178.e12-21.

Noack F, Ribbat-Idel J, Thorns C, Chiriac A, Axt-Fliedner R, Diedrich K, Feller A C. miRNA expression profiling in formalin-fixed and paraffin-embedded placental tissue samples from pregnancies with severe preeclampsia. *J Perinat Med.* 2011; 39: 267-271.

Kozakowska M, Szade K, Dulak J, Jozkowicz A. Role of heme oxygenase-1 in postnatal differentiation of stem cells: a possible cross-talk with microRNAs. *Antioxid Redox Signal.* 2014; 20:1827-1850.

Skrzypek K, Tertil M, Golda S, Ciesla M, Weglarczyk K, Collet G, Guichard A, Kozakowska M, Boczkowski J, Was H, Gil T, Kuzdzal J, Muchova L, Vitek L, Loboda A, Jozkowicz A, Kieda C, Dulak J. Interplay between heme oxygenase-1 and miR-378 affects non-small cell lung carcinoma growth, vascularization, and metastasis. *Antioxid Redox Signal.* 2013; 19:644-660.

Hou W, Tian Q, Steuerwald N M, Schrum L W, Bonkovsky H L. The let-7 microRNA enhances heme oxygenase-1 by suppressing Bach1 and attenuates oxidant injury in human hepatocytes. *Biochim Biophys Acta.* 2012; 1819: 1113-1122.

The invention claimed is:

1. A method of treating preeclampsia, comprising administering to a subject in need thereof an effective amount of at least one member of the group consisting of a combination of a mimic of microRNA-122 (mi-122) and mimic of microRNA-374b (mi-374b), a combination of one of the mimics and a functional fragment of the other mimic, and a combination of at least one of the mimics and a homologue of the other mimic, wherein each of the mimic, functional fragment, and/or homologue, is a double stranded structure not connected by nucleotides to form a hairpin.

2. The method according to claim 1, wherein the functional fragment or homologue is of mi-122.

3. The method according to claim 1, wherein the functional fragment, or homologue is of mi-374b.

4. A pharmaceutical composition, comprising at least one member of the group consisting of a combination of a mimic of microRNA-122 (mi-122) and a mimic of microRNA-374b (mi-374b), a combination of one of the mimics and a functional fragment of the other mimic, and a combination of at least one of the mimics and a homologue of the other mimic or pharmaceutically acceptable salts thereof, wherein each of the mimic, functional fragment, and/or homologue, is a double stranded structure not connected by nucleotides to form a hairpin.

5. The method of claim 1, wherein the mimic, homologue or functional fragment of microRNA-122 or the mimic, homologue or functional fragment of microRNA-374b decreases sFlt-1.

6. A method according to claim 1, wherein each of the mimic, functional fragment, and/or homologue, is chemically modified.

7. The method according to claim 1, wherein the combination is a combination of mi-122 and mi-374b.

8. The pharmaceutical composition of claim 4, wherein the combination comprises a functional fragment of a mimic of microRNA-122 (mi-122).

9. The pharmaceutical composition of claim 4, wherein the combination comprises a functional fragment of a mimic of microRNA-374b (mi-374b).

10. The pharmaceutical composition of claim 4, wherein the combination comprises a homologue of a mimic of microRNA-122 (mi-122).

11. The pharmaceutical composition of claim 4, wherein the combination comprises a homologue of a mimic of microRNA-374b (mi-374b).

12. The method according to claim 6, wherein the mimic, functional fragment or homologue is pegylated.

13. The pharmaceutical composition of claim 4, wherein the mimic of microRNA-122 (mi-122), mimic of microRNA-374b (mi-374b), functional fragment, and/or homolog is chemically modified.

14. The pharmaceutical composition of claim 13, wherein the chemically modified mimic of microRNA-122 (mi-122), chemically modified mimic of microRNA-374b (mi-374b), chemically modified function fragment and/or chemically modified homolog increases stability or efficiency of the pharmaceutical composition.

15. The pharmaceutical composition according to claim 13, wherein the chemically modified mimic of miR-122, the chemically modified mimic of miR-374b, the chemically modified functional fragments, or the chemically modified homologues thereof, and/or pharmaceutically acceptable salts thereof are pegylated.

* * * * *

SEQUENCE LISTING

```
<160> NUMBER OF SEQ ID NOS: 30

<210> SEQ ID NO 1
<211> LENGTH: 22
<212> TYPE: RNA
<213> ORGANISM: Homo sapiens

<400> SEQUENCE: 1
uggaguguga caagguguu ug                                                 22

<210> SEQ ID NO 2
<211> LENGTH: 22
<212> TYPE: RNA
<213> ORGANISM: Homo sapiens

<400> SEQUENCE: 2
auauaauaca accugcuaag ug                                                22

<210> SEQ ID NO 3
<211> LENGTH: 21
<212> TYPE: RNA
<213> ORGANISM: Homo sapiens

<400> SEQUENCE: 3
ucagugcaug acagaacuug g                                                 21

<210> SEQ ID NO 4
<211> LENGTH: 21
<212> TYPE: RNA
<213> ORGANISM: Homo sapiens

<400> SEQUENCE: 4
uagcagcaca gaaauauugg c                                                 21

<210> SEQ ID NO 5
<211> LENGTH: 22
<212> TYPE: RNA
<213> ORGANISM: Homo sapiens

<400> SEQUENCE: 5
caaacaccau ugucacacuc ca                                                22

<210> SEQ ID NO 6
<211> LENGTH: 22
<212> TYPE: RNA
<213> ORGANISM: Homo sapiens

<400> SEQUENCE: 6
cacuuagcag guuguauuau au                                                22
```

```
<210> SEQ ID NO 7
<211> LENGTH: 21
<212> TYPE: RNA
<213> ORGANISM: Homo sapiens

<400> SEQUENCE: 7
ccaaguucug ucaugcacug a                                              21

<210> SEQ ID NO 8
<211> LENGTH: 21
<212> TYPE: RNA
<213> ORGANISM: Homo sapiens

<400> SEQUENCE: 8
gccaauauuu cugugcugcu a                                              21

<210> SEQ ID NO 9
<211> LENGTH: 23
<212> TYPE: DNA
<213> ORGANISM: Homo sapiens

<400> SEQUENCE: 9
tttgtagcat tgtcatcact cct                                            23

<210> SEQ ID NO 10
<211> LENGTH: 20
<212> TYPE: DNA
<213> ORGANISM: Homo sapiens

<400> SEQUENCE: 10
tttgtcgacg gatagagaat                                                20

<210> SEQ ID NO 11
<211> LENGTH: 20
<212> TYPE: DNA
<213> ORGANISM: Homo sapiens

<400> SEQUENCE: 11
gtcaaaatag attattataa                                                20

<210> SEQ ID NO 12
<211> LENGTH: 17
<212> TYPE: DNA
<213> ORGANISM: Homo sapiens

<400> SEQUENCE: 12
gtcaagagca aggcgca                                                   17

<210> SEQ ID NO 13
<211> LENGTH: 22
<212> TYPE: DNA
<213> ORGANISM: Homo sapiens

<400> SEQUENCE: 13
tacaatattt gtactattat at                                             22

<210> SEQ ID NO 14
<211> LENGTH: 19
<212> TYPE: DNA
<213> ORGANISM: Homo sapiens

<400> SEQUENCE: 14
tacaatattt agacgcgct                                                 19
```

-continued

```
<210> SEQ ID NO 15
<211> LENGTH: 21
<212> TYPE: DNA
<213> ORGANISM: Homo sapiens

<400> SEQUENCE: 15
tccctccccc ccatgctgtg g                                              21

<210> SEQ ID NO 16
<211> LENGTH: 21
<212> TYPE: DNA
<213> ORGANISM: Homo sapiens

<400> SEQUENCE: 16
tgtaaacaag ggtccacagc a                                              21

<210> SEQ ID NO 17
<211> LENGTH: 45
<212> TYPE: DNA
<213> ORGANISM: Homo sapiens

<400> SEQUENCE: 17
ctctcaggag tagagtacct gtaaaggaga atctctaaat caagt                    45

<210> SEQ ID NO 18
<211> LENGTH: 45
<212> TYPE: DNA
<213> ORGANISM: Homo sapiens

<400> SEQUENCE: 18
acttgattta gagattctcc tttacaggta ctctactcct gagag                    45

<210> SEQ ID NO 19
<211> LENGTH: 22
<212> TYPE: RNA
<213> ORGANISM: Homo sapiens

<400> SEQUENCE: 19 guuguggua acagugugag gu                                              22

<210> SEQ ID NO 20
<211> LENGTH: 23
<212> TYPE: RNA
<213> ORGANISM: Homo sapiens

<400> SEQUENCE: 20
uuuguagcau ugucaucacu ccu                                            23

<210> SEQ ID NO 21
<211> LENGTH: 22
<212> TYPE: RNA
<213> ORGANISM: Homo sapiens

<400> SEQUENCE: 21
gugaaucguc caacauaaua ua                                             22

<210> SEQ ID NO 22
<211> LENGTH: 20
<212> TYPE: RNA
<213> ORGANISM: Homo sapiens

<400> SEQUENCE: 22
gucaaaauag auuauuauaa                                                20
```

```
<210> SEQ ID NO 23
<211> LENGTH: 21
<212> TYPE: RNA
<213> ORGANISM: Homo sapiens

<400> SEQUENCE: 23
gguucaagac aguacgugac u                                              21

<210> SEQ ID NO 24
<211> LENGTH: 21
<212> TYPE: RNA
<213> ORGANISM: Homo sapiens

<400> SEQUENCE: 24
ucccuccccc ccaugcacug u                                              21

<210> SEQ ID NO 25
<211> LENGTH: 16
<212> TYPE: DNA
<213> ORGANISM: Mus musculus

<400> SEQUENCE: 25
taaagtctaa tctcta                                                    16

<210> SEQ ID NO 26
<211> LENGTH: 21
<212> TYPE: DNA
<213> ORGANISM: Macaca mulatta

<400> SEQUENCE: 26
acctgtaaag tctaatctct a                                              21

<210> SEQ ID NO 27
<211> LENGTH: 21
<212> TYPE: DNA
<213> ORGANISM: Gorilla gorilla

<400> SEQUENCE: 27
acctgtaaag tctaatctct a                                              21

<210> SEQ ID NO 28
<211> LENGTH: 21
<212> TYPE: DNA
<213> ORGANISM: Pan troglodytes

<400> SEQUENCE: 28
acctgtaaag tctaatctct a                                              21

<210> SEQ ID NO 29
<211> LENGTH: 21
<212> TYPE: DNA
<213> ORGANISM: Homo sapiens

<400> SEQUENCE: 29
acctgtaaag tctaatctct a                                              21

<210> SEQ ID NO 30
<211> LENGTH: 21
<212> TYPE: RNA
<213> ORGANISM: Homo sapiens

<400> SEQUENCE: 30
cgguuauaaa gacacgacga u                                              21
```